US012577291B2

(12) United States Patent
Abdollahi et al.

(10) Patent No.: US 12,577,291 B2
(45) Date of Patent: *Mar. 17, 2026

(54) MEANS AND METHODS FOR TREATING AND DIAGNOSING FIBROSIS OR FIBROSIS-ASSOCIATED DISEASES

(71) Applicant: Deutsches Krebsforschungszentrum, Heidelberg (DE)

(72) Inventors: Amir Abdollahi, Heidelberg (DE); Kashi Javaherian, Lexington, MA (US); Jürgen Debus, Heidelberg (DE); Cheng Zhou, Dossenheim (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/058,131

(22) Filed: Nov. 22, 2022

(65) Prior Publication Data

US 2023/0382975 A1 Nov. 30, 2023

Related U.S. Application Data

(63) Continuation of application No. 15/781,028, filed as application No. PCT/EP2016/079777 on Dec. 5, 2016, now Pat. No. 11,548,934.

(30) Foreign Application Priority Data

Dec. 3, 2015 (EP) .................................... 15197746

(51) Int. Cl.
| | |
|---|---|
| *C07K 14/78* | (2006.01) |
| *A61K 9/00* | (2006.01) |
| *A61K 38/00* | (2006.01) |
| *A61K 45/06* | (2006.01) |
| *A61P 11/00* | (2006.01) |

(52) U.S. Cl.
CPC .............. *C07K 14/78* (2013.01); *A61P 11/00* (2018.01); *A61K 9/0019* (2013.01); *A61K 38/00* (2013.01); *A61K 45/06* (2013.01); *C07K 2317/53* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,524,811 B2 | 4/2009 | Folkman et al. | |
| 8,206,718 B2 | 6/2012 | Lo et al. | |
| 11,548,934 B2 * | 1/2023 | Abdollahi | A61P 17/00 |
| 2014/0220016 A1 * | 8/2014 | Shin | A61K 39/39558 |
| | | | 424/134.1 |
| 2014/0302026 A1 * | 10/2014 | Lee | A61P 37/06 |
| | | | 424/134.1 |

FOREIGN PATENT DOCUMENTS

| | | |
|---|---|---|
| EP | 1107989 B1 | 3/2010 |
| JP | 2007084459 A | 4/2007 |
| JP | 2014529605 A | 11/2014 |
| WO | 2011050311 A1 | 4/2011 |
| WO | 2012049328 A1 | 4/2012 |
| WO | 2013026913 A2 | 2/2013 |

OTHER PUBLICATIONS

Webster and Crowe "Matrix metallproteinases, their production by monocytes and macrophages and their potential role in HIV-related diseases" J. Leukocyte Biology 80:1052-1066. (Year: 2006).*
Brkic et al. "Friends or Foes: Matrix Metalloproteinases and Their Multifaceted Roles in Neurodegenerative Diseases" Mediators of Inflammation 2015: Article ID 620581. (Year: 2015).*
Vartak and Gemeinhart "Matrix metallproteinases: Underutilized targets for drug delivery" J. Drug Target 15:1-20. (Year: 2007).*
Schwarzbauer et al., "Fibronectins, Their Fibrillogenesis, and In Vivo Functions," Cold Spring Harbor Perspectives in Biology, 2011. 3(7).
Selman et al., "Idiopathic Pulmonary Fibrosis: Prevailing and Evolving Hypotheses about Its Pathogenesis and Implications for Therapy," (2001), Ann. Intern. Med. 134, p. 136-151.
Song et al., "Expression of vascular endothelial growth factor C and anti-angiogenesis therapy in endometriosis," International Journal of Clinical and Experimental Pathology 2014, vol. 7, No. 11, pp. 7752-7759.
Sudhakar et al., "Human tumstatin and human endostatin exhibit distinct antiangiogenic activities mediated by $\alpha v \beta 3$ and $\alpha 5 \beta 1$ integrins," Proc Natl Acad Sci U S A, 2003. 100(8): p. 4766-71.
Takahashi et al., "The RGD motif in fibronectin is essential for development but dispensable for fibril assembly," Journal of Cell Biology, 2007. 178(1): p. 167-78.
Tampe et al., "Potential approaches to reverse or repair renal fibrosis," Nature Reviews Nephrology Apr. 2014 226-237.

(Continued)

*Primary Examiner* — Sudhakar Katakam
*Assistant Examiner* — Zachary J Miknis
(74) *Attorney, Agent, or Firm* — Taft Stettinius & Hollister LLP

(57) ABSTRACT

The present invention is concerned with a protein oligomer comprising (i) at least two NC-1 monomers of collagen 18 or (ii) at least two endostatin domains of collagen 18 or (iii) at least two N-terminal peptides of the collagen 18 endostatin domain, for use in treating, ameliorating or preventing fibrosis or a fibrosis-associated disease, a vascular endothelial growth factor (VEGF)-related disease or a matrix metalloproteinase (MMP)-related disease. The invention further relates to the mentioned protein oligomer for use for detecting and/or diagnosing fibrosis or a fibrosis-associated disease, a vascular endothelial growth factor (VEGF)-related disease or a matrix metalloproteinase (MMP)-related disease.

Figure 1:
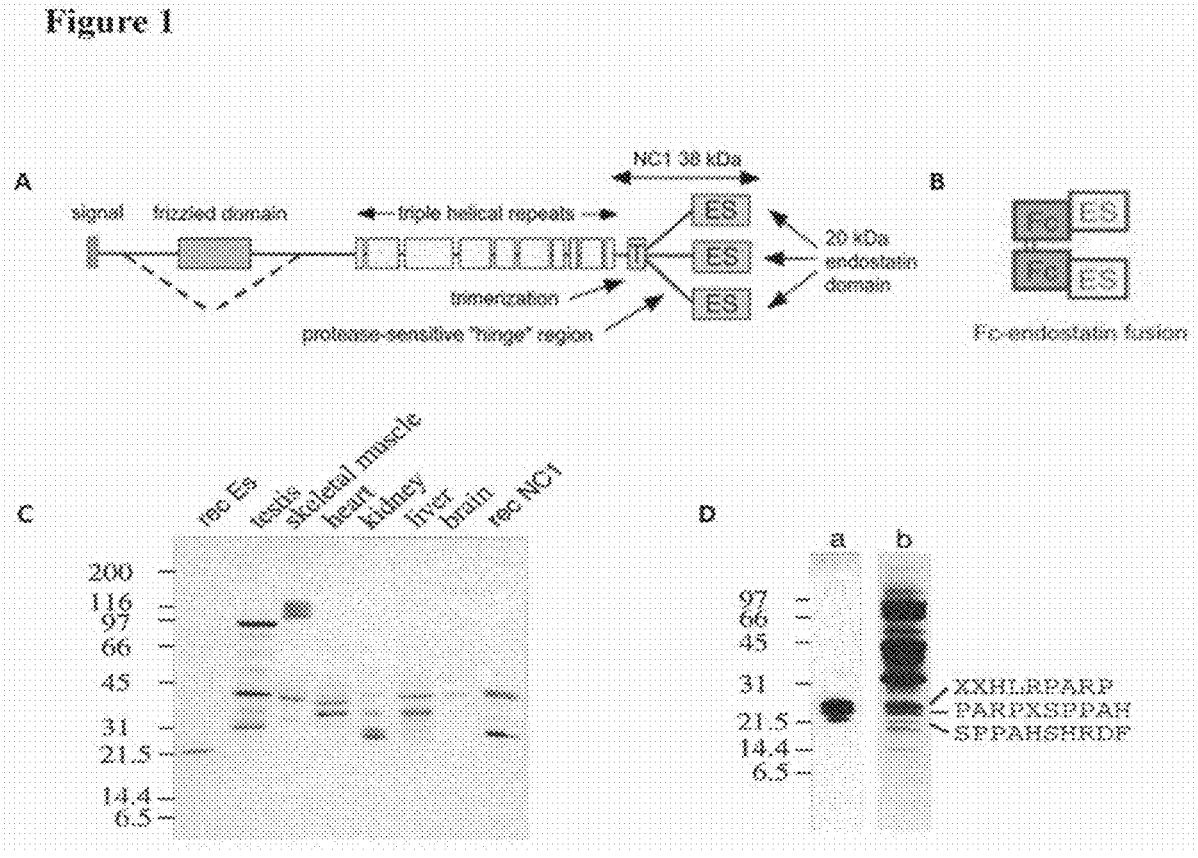

17 Claims, 12 Drawing Sheets
Specification includes a Sequence Listing.

(56) References Cited

OTHER PUBLICATIONS

Tjin et al., "A 27-Amino-Acid Synthetic Peptide Corresponding to the NH2-Terminal Zinc-Binding Domain of Endostatin Is Responsible for Its Antitumor Activity," Cancer Research, vol. 65, No. 9, (May 1, 2005), pp. 3656-3663.

To et al., "Plasma and cellular fibronectin: distinct and independent functions during tissue repair," 2011 Fibrogenesis & Tissue Repair, 4:21.

Torres et al., "Structural analysis of the N-terminal fragment of the antiangiogenic protein endostatin: A molecular dynamics study," Proteins, 2011. 79(9): p. 2684-92.

Vagner et al., "Peptidomimetics, a synthetic tool of drug discovery," Current Opinion in Chemical Biology 12, pp. 292-296.

Vancheri, "Common pathways in idiopathic pulmonary fibrosis and cancer," Eur Respir Rev 2013 22:265-272.

Varga et al., "Transforming growth factor-β as a therapeutic target in systemic sclerosis," (2009), Nature Reviews Rheumatology 5, p. 200-6.

Walters, "Computer-Assisted Modeling of Drugs," in Klegerman & Groves, eds., 1993, Pharmaceutical Biotechnology, Interpharm Press: Buffalo Grove, Ill., pp. 165-174.

Wijelath et al., "Heparin-II Domain of Fibronectin Is a Vascular Endothelial Growth Factor—Binding Domain," 2006, Circulation Research 99, 853-860.

Yamaguchi et al., "A Peptide Derived from Endostatin Ameliorates Organ Fibrosis," Sci Transl Med., 2012. 4(136).

Yamaguchi et al., Database accession No. XP002767168 (NLM24390105).

Yamaguchi et al., "A Peptide Derived from Endostatin Ameliorates Organ Fibrosis," Science Translational Medicine, vol. 4, Issues 132-136, pp. 230-238 (May 30, 2012), XP009183453.

Yoshida et al., "Inhibition of Corneal Neovascularization by Subconjunctival Injection of Fc-Endostatin, a Novel Inhibitor of Angiogenesis," Journal of Ophthalmology 2015, vol. 2015, pp. 1-8.

Zhang et al., "Endostar down-regulates HIF-1 and VEGF expression and enhances the radioresponse to human lung adenocarcinoma cancer cells," Molecular Biology Reports 2011, vol. 39, No. 1, pp. 89-95.

Boehm et al., "Zinc-Binding of Endostatin is Essential for Its Antiangiogenic Activity," 1998, Biochemical and Biophysical Research Communications, 252, 190-194.

Japanese Official Action; Japanese Patent Application No. 2018-548284; Nov. 4, 2020; 7 pages.

Wan et al. "Endostatin, an angiogenesis inhibitor, ameliorates bleomycin-induced pulmonary fibrosis in rats" Respiratory Research 14:56 (Year: 2013).

Zhang et al. "Protection against acute radiation-induced lung injury: A novel role for the anti-angiogenic agent Endostar" Molecular Medicine Reports 6:309-315. (Year: 2012).

Fay et al. "The First Draft of the Endostatin Interaction Network" J. Biol. Chem. 284:22041-22047. (Year: 2009).

Ding et al. "Zinc-dependent dimers observed in crystals of human endostatin" Proc. Natl. Acad. Sci. 95: 10443-10448. (Year: 1998).

Anonymous "Body weight information for NOD.CG-PRKDCSCID IL2RGTMQWJL/SZJ (005557)" Jackson Laboratory. (Year: 2020).

International Search Report of PCT/EP2016/079777 mailed Feb. 28, 2017.

Wing, S. et al. "Plasma and cellular fibronectin: distinct and independent functions during tissue repair" Sep. 16, 2011, Fibrogenesis & Tissue Repair, Beiomed Central Ltd. London, UK. vol. 4, No. 21, p. 17.

Yamaguchi, Y. et al. "Role of endostatin in fibroproliferative disorders.— as a candidate for anti-fibrosis therapy-" 2013 Nihon Rinsho Meneki Gakkai Kaishi. vol. 36. No. 6 p. 452-8. Database accession No. NLM24390105. abstract only.

European Patent Office, International Search Report for PCT/EP2016/079777, Feb. 13, 2017.

European Patent Office, Written Opinion of the International Searching Authority for PCT/EP2016/079777, Feb. 13, 2017.

Abdollahi et al., "Inhibition of platelet-derived growth factor signaling attenuates pulmonary fibrosis," (2005) The Journal of Experimental Medicine, J. Exp. Med. 201, p. 925-35.

Abdollahi et al., "Combined Therapy with Direct and Indirect Angiogenesis Inhibition Results in Enhanced Antiangiogenic and Antitumor Effects," Cancer Research 2003, 63, 8890.

Abdollahi et al., "Transcriptional network governing the angiogenic switch in human pancreatic cancer," Proc Natl Acad Sci U S A, 2007. 104(31): p. 12890-5.

Abdollahi et al., "Endostatin: The logic of antiangiogenic therapy," Drug Resistance Updates 2005, 8, 59-74.

Abdollahi et al., "Endostatin's Antiangiogenic Signaling Network," Molecular Cell 2004, vol. 13, 649-663.

Abe et al., "Identification of a Noval Collagen Chain Represented by Extensive Interruptions in the Triple-Helical Region," 1993, Biochemical and Biophysical Research Communications, vol. 196, No. 2, 576-582.

Ali et al., "Protein oligomerization: How and why," 2005, Bioorganic and Medicinal Chemistry 13, 5013.

Allen et al., "Growth factors in idiopathic pulmonary fibrosis: relative roles," (2002), Respiratory Research vol. 3, No. 1.

"American Thoracic Society/European Respiratory Society International Multidisciplinary Consensus Classification of the Idiopathic Interstitial Pneumonias," Am. J. Respir. Crit Care Med. (2002), 165, p. 277-304.

Bergers et al., "Effects of Angiogenesis Inhibitors on Multistage Carcinogenesis in Mice," Science 284(5415), p. 808-812, 1999.

Boon et al., "Molecular Phenotypes Distinguish Patents with Relatively Stable from Progressive Idiopathic Pulmonary Fibrosis (IPF)," (2009), PLoS One, 4, e5134.

Capon et al., "Designing CD4 immunoadhesins for AIDS therapy," 1989, Nature vol. 337, 525.

Chada et al., "The Synergy Site of Fibronectin Is Required for Strong Interaction with the Platelet Integrin !IIb#3," Annals of Biomedical Engineering, 2006. 34(10): p. 1542-52.

Crestani et al., "Hepatocyte Growth Factor and Lung Fibrosis," Proc Am Thorac Soc, 2012. 9(3): p. 158-63.

Declèves et al., "Novel targets of antifibrotic and anti-inflammatory treatment in CKD," Nature Reviews Nephrology, vol. 10, p. 257-267 (2014).

Ding et al., "Zinc-dependent dimers observed in crystals of human endostatin," 1998, Proc. Natl. Acad. Sci. vol. 95, 10443.

Fee et al., "Protein PEGylation: An overview of chemistry and process considerations," 2010, European Pharmaceutical Review 15, 18.

Folkman, J., "Antiangiogenesis in cancer therapy—endostatin and its mechanisms of action," Experimental Cell Research, 2006. 312(5): p. 594-607.

Gordon et al., "Phase I Safety and Pharmacokinetic Study of Recombinant Human Anti-Vascular Endothelial Growth Factor in Patients With Advanced Cancer," 2001, Journal of Clinical Oncology, vol. 19, 843.

Gross et al., "Idiopathic Pulmonary Fibrosis," (2001), N. Engl. J. Med. 345, p. 517-525.

Gurujeyalakshmi et al., "Procollagen Gene Expression is Down-Regulated by Taurine and Niacin at the Trnascriptional Level in the Bleomycin Hamster Model of Lung Fibrosis," Journal of Pharmacology and Experimental Therapeutics, 1996, 277(2):1152-115.

Gurujeyalakshmi et al., "Pirfenidone inhibits PDGF isoforms in bleomycin hamster model of lung fibrosis at the translational level," (1999), Am. J. Physiol. 276, p. L311-L318.

Hallahan et al., "Effects of Intercellular Adhesion Molecule 1 (ICAM-1) Null Mutation on Radiation-Induced Pulmonary Fibrosis and Respiratory Insufficiency in Mice," (2002), Journal of the National Cancer Institute 94, p. 733-741.

Heljasvaara et al., "Generation of biologically active endostatin fragments from human collagen XVIII by distinct matrix metalloproteases," Experimental Cell Research 2005, 307, 292.

Holash et al., "VEGF-Trap: A VEGF blocker with potent antitumor effects," 2002, Proc. Natl. Acad. Sci. USA 99, 11393.

Javaherian et al., "Laminin Modulates Morphogenic Properties of the Collagen XVIII Endostatin Domain," Journal of Biological Chemistry 2002, 277, 45211.

(56)        References Cited

OTHER PUBLICATIONS

Jia et al., "Modulation of collagen XVIII/endostatin expression in lobular and bilary rat liver fibrogenesis," Journal of Hepatology (2001)386-391.

Kamp, "Idiopathic Pulmonary Fibrosis—The Inflammation Hypothesis Revisited," (2003), Chest 124, p. 1187-1190.

Klein et al., "Progress in overcoming the chain association issue in bispecific heterodimeric IgG antibodies," MAbs. Nov. 1, 2012; 4(6): 653-663.

Kuo et al., "Oligomerization-dependent Regulation of Motility and Morphogenesis by the Collagen XVIII NC1/Endostatin Domain," Journal of Cell Biology, 2001. 152(6): p. 1233-46.

Lee et al., "Linking Antibody Fc Domain to Endostatin Significantly Improves Endostatin Half-life and Efficacy," Clinical Cancer Research, 2008. 14(5): p. 1487-1493.

Leiss et al., "The role of integrin binding sites in fibronectin matrix assembly in vivo," Current Opinion in Cell Biology, 2008. 20(5): p. 502-7.

Lo et al., "High level expression and secretion of Fc-X fusion proteins in mammalian cells," 1998, Protein Engineering, vol. 11, 495.

Mason et al., "Pharmacological Therapy for Idiopathic Pulmonary Fibrosis—Past, Present, and Future," (1999), Am. J. Respir. Crit. Care Med. 160, p. 1771-1777.

Movsas et al., "Pulmonary Radiation Injury," (1997) Chest 111, p. 1061-1076.

Oh et al., "Cloning of cDNA and Genomic DNA Encoding Human Type XVIII Collagen and Localization of the alpha1 (XVIII) Collagen Gene to Mouse Chromosome 10 and Human Chromosome 21," Genomics 1994, 19, 494.

Oh et al., "Isolation and sequencing of cDNAs for proteins with multiple domains of Gly-Xaa-Yaa repeats identify a distinct family of collagenous proteins," Proc. Natl. Acad. Sci. 994, 91, 4229.

O'Reilly et al., "Endostatin: An Endogenous Inhibitor of Angiogenesis and Tumor Growth," Cell, 1997. 88(2): p. 277-85.

Peng et al., "Recombinant Human Endostatin Normalizes Tumor Vasculature and Enhances Radiation Response in Xenogranted Human Nasopharyngeal Carcinoma Models," PLoS One 2012, vol. 7, No. 4, p. e34646.

Phin et al., "Imbalance in the Pro-Hepatocyte Growth Factor Activation System in Bleomycin-Induced Lung Fibrosis in Mice," Am J Respir Cell Mol Biol, 2010. 42(3): p. 286-93.

Rafii et al., "A review of current and novel therapies for idiopathic pulmonary fibrosis," J. Thorac Dis. (2013), 5, p. 48-73.

Raghu et al., "Incidence and Prevalence of Idiopathic Pulmonary Fibrosis," (2006), Am. J. Respir. Crit. Care Med. 174, p. 810-6.

Raghu et al., "An Official ATS/ERS/JRS/ALAT Statement: Idiopathic Pulmonary Fibrosis: Evidence-based Guidelines for Diagnosis and Management," (2011), Am. J. Respir. Crit. Care Med. 183, p. 788-824.

Ray, "Key role for !v integrins in myofibroblasts in liver fibrosis," Nature Reviews Gastroenterology & Hepatology, Jan. 2014, vol. 11, 4.

Ren et al., "Endostatin inhibits hypertrophic scarring in a rabbit ear model," Biomed & Biotechnology 2013 14(3) 224-230.

Ridgeway et al., "Knobs-into-holes' engineering of antibody CH3 domains for heavy chain heterodimierization," Protein Engineering Jul. 1996;9(7):617-21.

Rubin et al., "A Perpetual Cascade of Cytokines Postirradiation Leads to Pulmonary Fibrosis," (1995), Int. J. Radiation Oncology Biol. Phys., vol. 33, p. 99-109.

Sasaki et al., "Structure, function and tissue forms of the C-terminal globular domain of collagen XVIII containing the angiogenesis inhibitor endostatin," EMBO Journal, 1998. 17(15): p. 4249-56.

* cited by examiner

Figure 2

The sequences of endostatin and related peptides mEndostatin (184 aa)

$H_2N$-HTHQDFQPVLHLVALNTPLSGGMRGIRGADFQCFQQARAVGLSGTFRAFLSS
RLQDLYSIVRRADRGSVPIVNLKDEVLSPSWDSLFSGSQGQLQPGARIFSFDGRDV
LRHPAWPQKSVWHGSDPSGRRLMESYCETWRTETTGATGQASSLLSGRLLEQKA
ASCHNSYIVLCIENSFMTSFSK-COOH (SEQ ID NO: 18)

hEndostatin (180 aa)

$H_2N$-HSHRDFQPVLHLVALNAPLSGGMRGIRGADFQCFQQARAVGLAGTFRAFLSS
RLQDLYSIVRRADRAAVPIVNLKDELLFPSWEALFSGSEGPLKPGARIFSFDGKDVLR
HPTWPQKSVWHGSDPNGRRLTESYCETWRTEAPSATGQASSLLGGRLLGQSAA
SCHHAYIVLCIENSFMT-COOH (SEQ ID NO: 19)

mP1 peptide (27 aa)

HTHQDFQPVLHLVALNTPLSGGMRGIR (SEQ ID NO: 20)

hP1 peptide (27 aa)

HSHRDFQPVLHLVALNAPLSGGMRGIR (SEQ ID NO: 22)

E4 (C-terminal) peptide (48 aa)

H-133SYCETWRTEAPSATGQASSLLGGRLLGQSAASCHHAYIVLCIENSFMT180-
CONH2 (SEQ ID NO: 21)

Figure 6
A
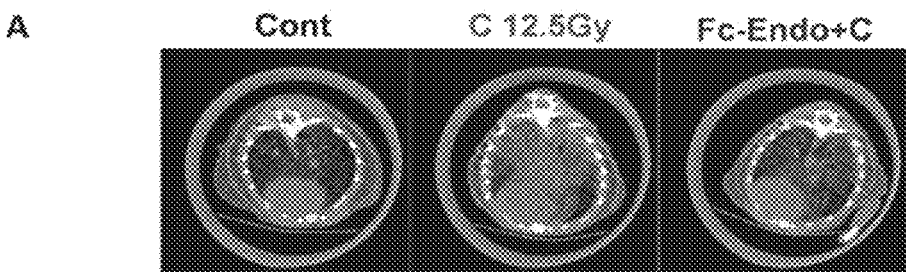
B
C
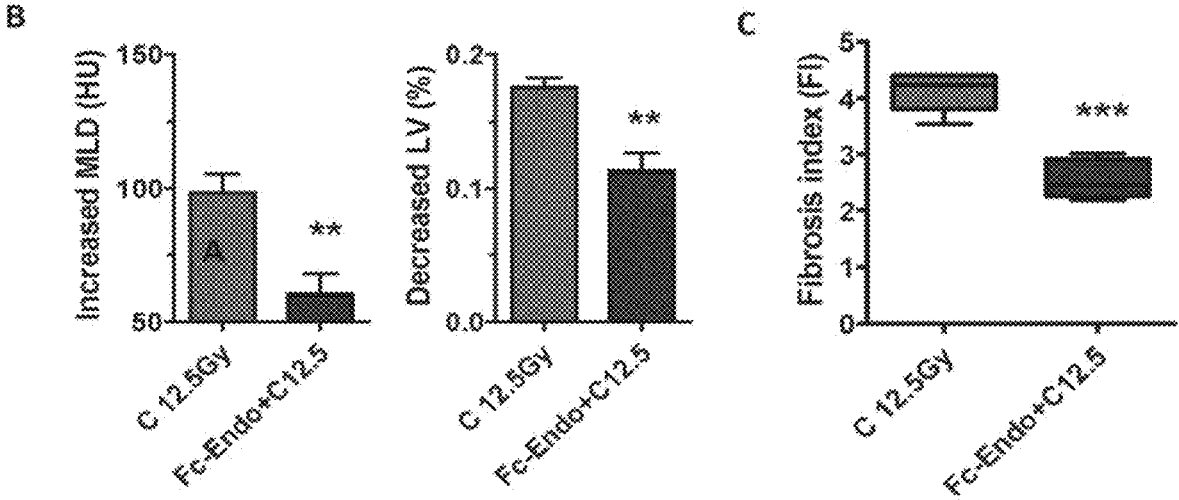
D
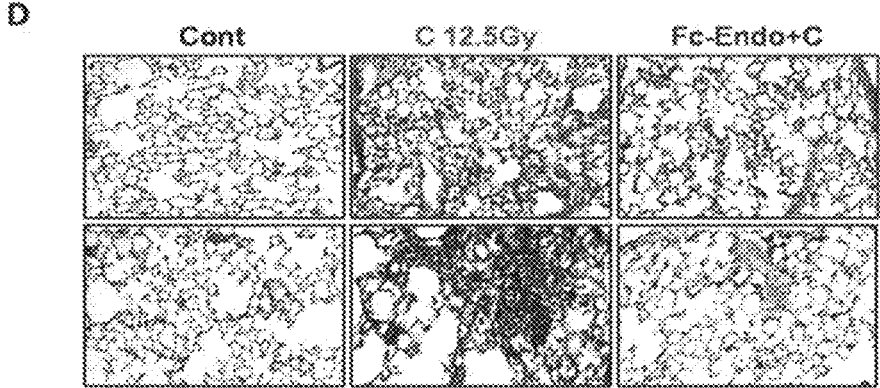

Figure 12
A
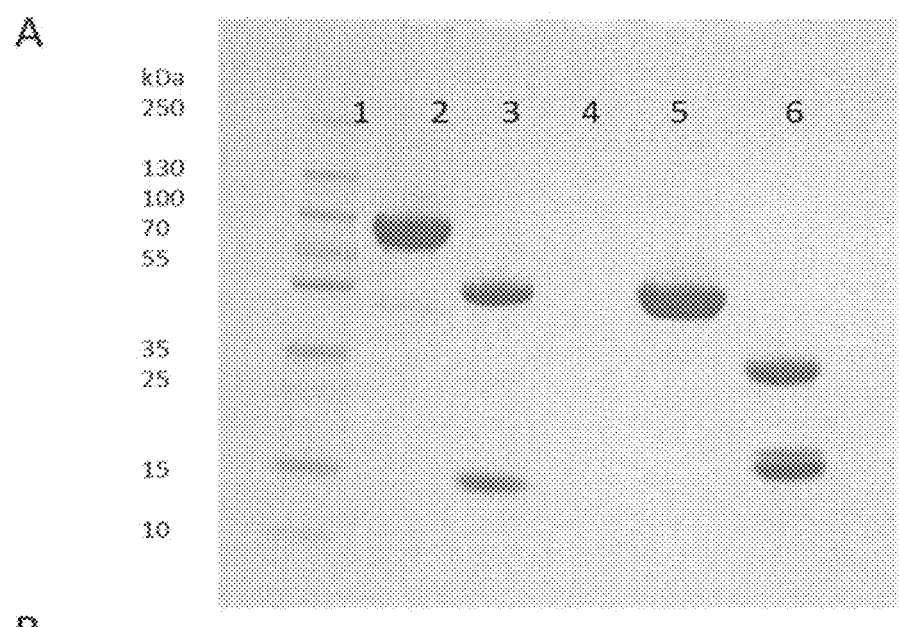
B
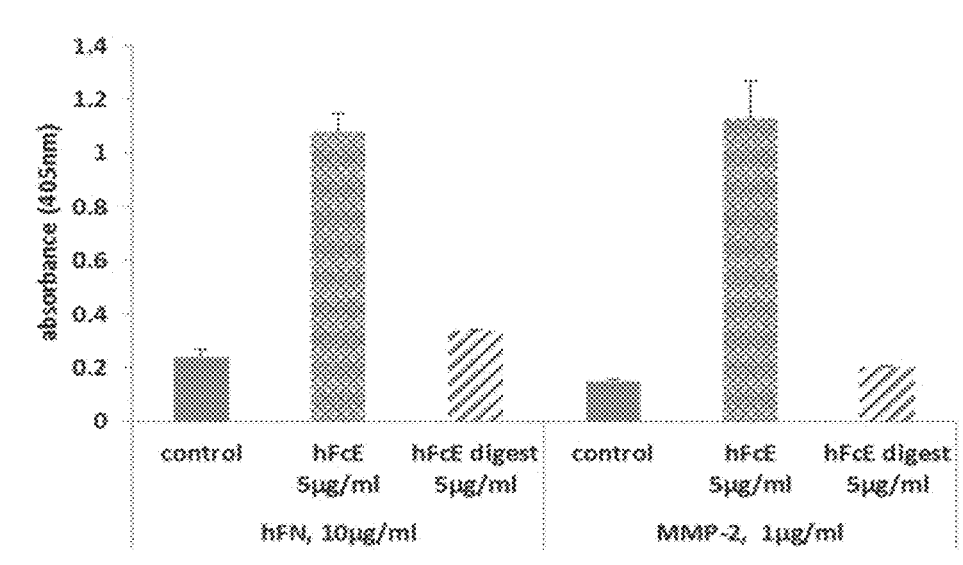

Figure 13
A
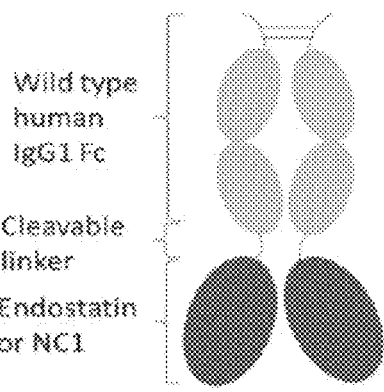
B
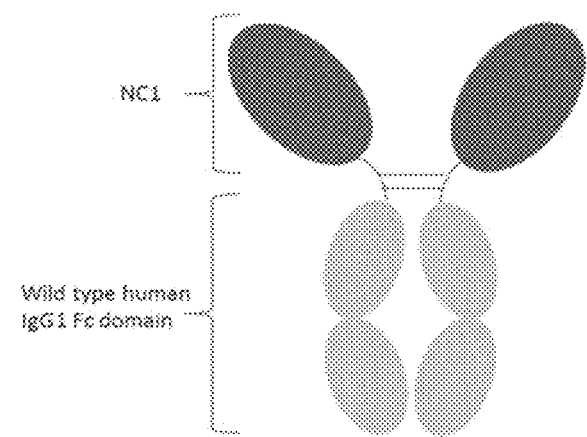

Figure 14
A
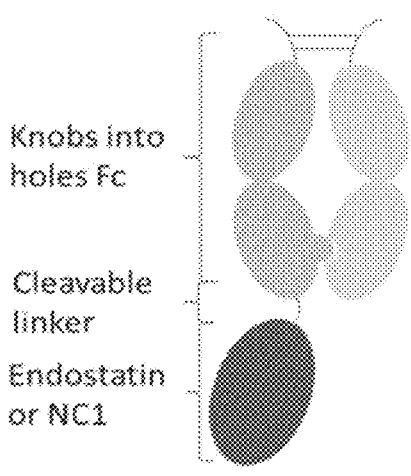
Knobs into
holes Fc
Cleavable
linker
Endostatin
or NC1
B
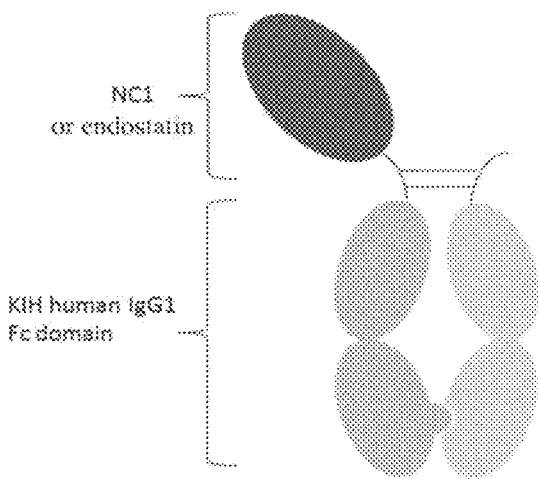
NC1
or endostatin
KIH human IgG1
Fc domain

MEANS AND METHODS FOR TREATING AND DIAGNOSING FIBROSIS OR FIBROSIS-ASSOCIATED DISEASES

CROSS-REFERENCE TO RELATED APPLICATIONS

This application is a continuation of and claims priority to U.S. patent application Ser. No. 15/781,028 filed on Jun. 1, 2018, which is a U.S. National Phase of International PCT Application No. PCT/EP2016/079777 filed on Dec. 5, 2016, which claims priority to European Patent Application No. 15197746.9 filed on Dec. 3, 2015. The contents of each application are incorporated herein by reference in their entireties.

STATEMENT REGARDING SEQUENCE LISTING

This application incorporates by reference the material in the ST.26 XML file titled ASD05-62_Replacement_Sequence_Listing, which was created on Aug. 15, 2023 and is 40 KB.

The present invention is concerned with a protein oligomer comprising (i) at least two NC-1 monomers of collagen 18 or (ii) at least two endostatin domains of collagen 18 or (iii) at least two N-terminal peptides of the collagen 18 endostatin domain, for use in treating, ameliorating or preventing fibrosis or a fibrosis-associated disease, a vascular endothelial growth factor (VEGF)-related disease or a matrix metalloproteinase (MMP)-related disease. The invention further relates to the mentioned protein oligomer for use for detecting and/or diagnosing fibrosis or a fibrosis-associated disease, a vascular endothelial growth factor (VEGF)-related disease or a matrix metalloproteinase (MMP)-related disease.

Excessive deposition of extracellular matrix (ECM) components such as Fibronectin (FN) and type I collagen (Col1α1) by organ fibroblasts is defined as fibrosis. Organ fibrosis is the final common pathway for many diseases that result in end-stage organ failure. Uncontrollable wound-healing responses, including acute and chronic inflammation, angiogenesis, activation of resident cells and extracellular matrix remodeling are thought to be involved in the pathogenesis of fibrosis.

Pulmonary fibrosis comprises a group of interstitial disorders of the lung parenchyma that develop as a consequence of multiple causes, including radiotherapy and chemotherapy for lung neoplasms (Am. J. Respir. Crit Care Med. (2002) 165, p. 277-304; Movsas et al. (1997) Chest 111, p. 1061-1076). The pathophysiologic events induced by radiation have striking similarities to those that occur after other types of lung injury, such as surgery, chemotherapy, and idiopathic pulmonary fibrosis (IPF) (Rubin et al. (1995), Int. J. Radiat. Oncol. Biol. Phys. 33, p. 99-109).

In a study published in 2006 based on a United States healthcare claims database, the prevalence of IPF was between 14-42.7 per 100,000, depending on whether narrow or broad case-finding criteria was used (Raghu et al. (2006), Am. J. Respir. Crit. Care Med. 174, p. 810-6). More recently, in May 2012, a systematic survey of literature estimated the prevalence of idiopathic pulmonary fibrosis (IPF) in the European Union to be 26 per 100,000. The findings of various studies on the incidence of IPF are summarized in a review by Rafii et al. (J. Thorac Dis. (2013), 5, p. 48-73). IPF represents the most common cause of death from progressive lung disease. Retrospective studies suggest that the median survival after diagnosis of IPF is 2-3 years, however, the course of IPF is variable, with some patients experiencing long periods of stability while others have frequent exacerbations or a rapid decline (Raghu et al. (2011), Am. J. Respir. Crit. Care Med. 183, p. 788-824; Selman et al. (2001), Ann. Intern. Med. 134, p. 136-51; Boon et al. (2009), PLOS One, 4, e5134).

Clinically, IPF is characterized by interstitial infiltrates, progressive dyspnea, and worsening of pulmonary function that may lead to death from respiratory failure (Am. J. Respir. Crit Care Med. (2002), 165, p. 277-304; Allen and Spiteri (2002), Respir. Res. 3, p. 13; Gross and Hunninghake (2001), N. Engl. J. Med. 345, p. 517-525).

An ideal animal model for IPF does not yet exist, but bleomycin- and radiation-induced lung fibrosis models have been used to study lung fibrosis so far (Rubin, loc. cit.).

From a molecular point of view, TGF-beta (TGF-β) is the prototype fibrotic cytokine which is increased in fibrotic organs and contributes to the development of fibrosis by stimulating the synthesis of extracellular matrix molecules, activating fibroblasts to α-smooth muscle actin-expressing myofibroblasts, and down-regulating matrix metalloproteinases (MMPs). Though aberrant TGF-beta expression is implicated in the pathogenesis of fibrosis in systemic sclerosis, an anti-TGF-beta monoclonal antibody evaluated in a small trial of early systemic sclerosis failed to show any efficacy (Varga et al. (2009), Nature Reviews Rheumatology 5, p. 200-6).

The findings of another study suggested a pivotal role of PDGF signaling in the pathogenesis of pulmonary fibrosis and indicated that inhibition of fibrogenesis, rather than inflammation, is critical to anti-fibrotic treatment (Abdollahi et al. (2005), J. Exp. Med. 201, p. 925-35).

Recently, anti-fibrotic activity has been reported for C-terminal endostatin polypeptides but not for N-terminal endostatin polypeptides, in TGF-beta- and bleomycin-induced fibrosis (WO 2011/050311; Yamaguchi et al. (2012), Sci. Transl. Med., 4, p. 136ra71). Endostatin is a naturally occurring 183-amino acid proteolytic fragment of collagen XVIII that localizes in the basement membrane around blood vessels. The anti-tumor properties of this protein have been extensively described, demarcating endostatin as an endogenous inhibitor of angiogenesis [Bergers, G., et al., *Effects of angiogenesis inhibitors on multistage carcinogenesis in mice*. Science, 1999. 284 (5415): p. 808-12; O'Reilly, M. S., et al., *Endostatin: an endogenous inhibitor of angiogenesis and tumor growth*. Cell, 1997. 88 (2): p. 277-85, Folkman, J., *Antiangiogenesis in cancer therapy—endostatin and its mechanisms of action*. Exp Cell Res, 2006. 312 (5): p. 594-607]. Further, it supresses many signaling cascades such as pro-inflammatory NF-κB, coagulation and adhesion cascades [Abdollahi, A., et al., *Transcriptional network governing the angiogenic switch in human pancreatic cancer*. Proc Natl Acad Sci USA, 2007. 104 (31): p. 12890-5].

Despite the medical need, there has been remarkably little progress in the development of effective therapeutic strategies for fibrosis thus far (see, e.g., Am. J. Respir. Crit Care Med. (2002), 165, p. 277-304; Allen and Spiteri, loc. cit.; Gross and Hunninghake, loc. cit.; Kamp (2003), Chest 124, p. 1187-11909; Mason et al. (1999), Am. J. Respir. Crit. Care Med. 160, p. 1771-1777; Rafii et al. (2013), J. Thorac Dis. 5, p. 48-73).

There is, thus, a need in the art for the development of effective treatment modalities for fibrosis.

The technical problem underlying the present invention could be seen as the provision of means and methods which comply with the afore-mentioned needs. This technical problem has been solved by the embodiments characterized in the claims and herein below.

Accordingly, the present invention relates to a protein oligomer comprising (i) at least two NC-1 monomers of collagen 18 or (ii) at least two endostatin domains of collagen 18 or (iii) at least two N-terminal peptides of the collagen 18 endostatin domain, for use in treating, ameliorating or preventing fibrosis or a fibrosis-associated disease.

The invention further pertains to a protein oligomer comprising (i) at least two NC-1 monomers of collagen 18 or (ii) at least two endostatin domains of collagen 18 or (iii) at least two N-terminal peptides of the collagen 18 endostatin domain, for use in treating, ameliorating or preventing a vascular endothelial growth factor (VEGF)-related disease or a matrix metalloproteinase (MMP)-related disease.

The term "protein" or "polypeptide" or "peptide" (all terms are used interchangeably, if not indicated otherwise) as used herein encompasses isolated and/or purified (poly) peptides being essentially free of other host cell polypeptides. The term "peptide" as referred to herein comprises at least two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60, 70, 80, 90, 100, 150, 200, 250, 300 or even more amino acid residues where the alpha carboxyl group of one is bound to the alpha amino group of another. A post-translational modification of the protein or peptide as used herein is the modification of a newly formed protein or peptide and may involve deletion of amino acids, chemical modification of certain amino acids, for example, amidation, acetylation, phosphorylation, glycosylation, formation of pyroglutamate, oxidation/reduction of sulfa group on a methionine, or addition of similar small molecules, to certain amino acids.

The term "protein" or "peptide" as used herein encompasses peptidomimetics. As known in the art, peptidomimetics are compounds whose essential elements (pharmacophore) mimic a natural peptide or protein in 3D space and which retain the ability to interact with the biological target (such as Fibronectin) and produce the same biological effect (for example, anti-fibrotic activity as defined herein); see, e.g., the review by Vagner et al. 2008, Current Opinion in Chemical Biology 12, Pages 292-296. Peptidomimetics are designed to circumvent some of the problems associated with a natural peptide, e.g., stability against proteolysis (duration of activity) and poor bioavailability. Certain other properties, such as selectivity for the biological target, such as Fibronectin, or potency of the biological activity, such as anti-fibrotic activity, often can be substantially improved.

Protein or peptide modifications as used herein include synthetic embodiments of (poly) peptides described herein. In addition, analogs (non-peptide organic molecules), derivatives (chemically functionalized (poly) peptide molecules obtained starting with the disclosed (poly) peptide sequences) and variants (homologs) of these proteins can be utilized in the methods and medical and diagnostic uses described herein. Each (poly) peptide of this disclosure is comprised of a sequence of amino acids, which may be either L- and/or D-amino acids, naturally occurring and otherwise. Peptides can be modified by a variety of chemical techniques to produce derivatives having essentially the same activity, e.g. anti-fibrotic activity, as the unmodified (poly) peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide. Hydroxyl groups of the polypeptide side chains may be converted to $C_1$-$C_{16}$ alkoxy or to a $C_1$-$C_{16}$ ester using well-recognized techniques. Phenyl and phenolic rings of the polypeptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the (poly) peptides of this invention to select and provide conformational constraints to the structure that result in enhanced stability.

The protein or (poly) peptide as referred to herein can also be a fusion protein. The term "fusion protein" as used herein denotes a chimeric protein (literally, made of parts from different sources) which is created through the joining of two or more genes that originally coded for separate proteins. Translation of this fusion gene results in a single or multiple polypeptides with functional properties derived from each of the original proteins. For example, the fusion protein as used herein comprises, e.g., a NC-1 monomer of collagen 18 and a Fc region of an immunoglobulin, a NC-1 monomer of collagen 18 and a Fc dimer, an endostatin domain of collagen 18 and a Fc region of an immunoglobulin, an endostatin domain of collagen 18 and a Fc dimer, an endostatin domain of collagen 18 with a single mutation at position 7 in which glutamine is replaced by cysteine and a Fc region of an immunoglobulin, an endostatin domain of collagen 18 with a single mutation at position 7 in which glutamine is replaced by cysteine and a Fc dimer, a N-terminal peptide of the collagen 18 endostatin domain and a Fc region of an immunoglobulin or a N-terminal peptide of the collagen 18 endostatin domain and a Fc dimer. For example, it can be advantageous to express a NC-1 monomer of collagen 18 and a Fc region of an immunoglobulin together with a Fc region of an immunoglobulin in a cell to avoid uncontrolled aggregation of the NC-1. Or it can be appropriate to omit or mutate the native association region in NC-1 so that NC-1 cannot oligomerize any longer via this association region. If such a NC-1 without functional association region is fused to a Fc region, this results in the formation of a NC-1 dimer. The fusion protein can additionally encompass, e.g., a RGD motif and/or a PHSRN (SEQ ID NO: 31) motif of Fibronectin. The terms "NC-1 monomer of collagen 18", "endostatin domain of collagen 18", "N-terminal peptide of the collagen 18 endostatin domain", "Fc region", "RGD motif" and "PHSRN (SEQ ID NO: 31) motif of Fibronectin" are defined elsewhere herein. Further fusion proteins encompassed by the present invention are indicated elsewhere in the specification and the following Examples. Recombinant fusion proteins are created, e.g., by recombinant DNA technology well described in the art see, e.g., Sambrook et al., Molecular cloning: a laboratory manual/Sambrook, Joseph; Russell, David W.—3rd ed.—New York: Cold Spring Harbor Laboratory, 2001.

The term "oligomer" usually refers to a macromolecular complex formed by non-covalent bonding of a few macromolecules like proteins or nucleic acids, in biochemistry. A dimer is per definition a macromolecular complex formed by two, usually non-covalently bound, molecules like proteins or peptides. Such a complex can also be formed by protein domains which are parts of protein sequences and structures that can evolve, function, and exist independently of the rest of the protein chain(s). A homo-dimer is formed by two identical molecules. The underlying process is called homo-dimerization. A hetero-dimer is built by two different molecules which are formed by hetero-dimerization. As known in the art, most dimers or trimers in biochemistry are not connected by covalent bonds, with the exception of disulfide bridges. Some proteins contain specialized domains to ensure dimerization, trimerization or oligomerization, so called dimerization, trimerization or oligomerization domains, as further defined herein below, and well known in the art. To provide an example, dimerization can be mediated by an Fc domain of an immunoglobulin or by disulfide bridges or, both or, other means as described elsewhere herein. For instance, Fc-endostatin (FcE) as used in Example 11 consists of two Fc chains (connected by disulfide bonds), extended to two molecules of endostatin each linked to a single Fc chain. Therefore, the two adjacent endostatin molecules become a dimer as a result of the Fc dimer. Another dimeric construct used in Example 11 comprised two endostatin domains of collagen 18. Each endostatin domain contained a single mutation at position 7 in which glutamine was replaced by cysteine. Each endostatin domain was linked to an Fc region of an immunoglobulin, with an intervening enterokinase cleavage site. In this construct, both Fc and endostatin molecules were dimerized by their corresponding disulfide bonds. Enterokinase digestion of this recombinant protein resulted in an Fc dimer and an endostatin dimer. A trimer is a macromolecular complex formed by three, usually non-covalently bound peptides, proteins or protein domains. For instance, for trimerization, the native association region within the NC-1 domain can be used which mediates the trimerization of NC-1 of collagen 18 because the native association region within the NC-1 domain of collagen 18 functions as a trimerization domain. A homo-trimer is formed by three identical molecules, whereas a hetero-trimer is built by three different molecules. For instance, collagen 18 is a homo-trimeric protein. A tetramer consists of four molecules, a pentamer of five molecules, and so on. In these cases, complex formation is often mediated by oligomerization domains, as set forth above.

In the context of the present invention, an "oligomer" is to be understood as a "protein oligomer" or "peptide oligomer" that comprises a few monomer units, e.g., two, three, four, five or even more monomer units. Accordingly, the oligomer can be, e.g., a dimer, trimer, tetramer, pentamer, and so on. Preferably, the oligomer is a homo-dimer, homo-trimer etc. The monomer unit (or briefly monomer) can be, e.g., an NC-1 monomer of human or murine collagen 18, an endostatin domain of human or murine collagen 18, or an N-terminal peptide of the human or murine collagen 18 endostatin domain, as specified elsewhere herein. The monomer can also be an NC-1 monomer of rhesus, macaque or primate collagen 18, an endostatin domain of rhesus, macaque or primate collagen 18, or an N-terminal peptide of the rhesus, macaque or primate collagen 18 endostatin domain.

The monomer can also be a fusion protein comprising an NC-1 monomer of human, rhesus, macaque, primate or murine collagen 18, an endostatin domain of human, rhesus, macaque, primate or murine collagen 18, or an N-terminal peptide of the human, rhesus, macaque, primate or murine collagen 18 endostatin domain. The term "fusion protein" as used herein comprises at least one NC-1 monomer, at least one endostatin domain, or at least one N-terminal endostatin peptide or peptide derived from the N-terminus of the endostatin domain, as defined herein. Encompassed are also fusion proteins comprising two, three of even more NC-1 monomers, two, three or even more endostatin domains, or two, three of even more N-terminal endostatin peptides or peptides derived from the N-terminus of the endostatin domain, as defined herein For example, said at least one NC-1 monomer, endostatin domain or N-terminal endostatin peptide or peptide derived from the N-terminus of the endostatin domain can be linked to a Fc domain from an immunoglobulin, a purification tag, a label, another therapeutic agent, such as an anti-fibrotic agent, an anti-angiogenic agent and/or anti-tumorigenic agent, or the like. A "label" as referred to herein is a detectable compound or composition that is conjugated directly or indirectly to another molecule, such as a NC-1 monomer of human, rhesus, macaque, primate or murine collagen 18, an endostatin domain of human, rhesus, macaque, primate or murine collagen 18, or an N-terminal peptide of the human, rhesus, macaque, primate or murine collagen 18 endostatin domain, to facilitate detection of that molecule. Specific, non-limiting examples of labels include fluorescent tags, enzymatic linkages, and radioactive isotopes. Preferably, the fusion protein is human, rhesus, macaque or primate, more preferably human. The Fc domain from the immunoglobulin can be fused either to the N-terminus or the C-terminus of the monomer as defined herein, preferably to the N-terminus.

The term "protein oligomer" (or "peptide oligomer") as used herein includes also protein preparations comprising the protein oligomer or peptide oligomer and other proteins, agents or compounds, in addition. For example, said oligomer as defined herein can be administered to a subject in the need thereof, in a combination regimen, using one or more further anti-fibrotic, anti-angiogenic and/or anti-tumorigenic protein(s), compound(s) or agent(s). Combinations of medications are often more effective against fibrosis or fibrosis-associated diseases than a single medication used alone. To provide an example, the protein oligomer or peptide oligomer as defined herein can be used in combination with angiostatin or an angiostatin fusion protein, such as angiostatin linked to an Fc domain of an immunoglobulin, or together with inhibitors of other pathways associated with the fibrosis process, including, for example, inhibitors of TGF-beta, PDGF, VEGF, mTOR, CTGF, integrins, matrix-metalloproteinases, anti-inflammatory agents such as steroids inhibitors of cyclooxygenase, IKK/NFkB. JAK/STAT, and/or Pi3K signaling.

The term "collagen 18" and "collagen XVIII" are used interchangeably herein and refer to the same protein. Collagen 18 consists of a central, interrupted triple-helical domain, flanked at the N-terminus (NC-11 domain) and C-terminus (NC-1 domain), by larger non-triple helical, globular structures (Oh et al., *PNAS* 1994, 91, 4229; Oh et al., *Genomics* 1994, 19, 494; Abe et al. 1993, *Biochem. Biophys. Res. Commun.* 196, 576). The Type XVIII collagen belongs to a unique and novel subclass of the collagen superfamily for which the name "MULTIPLEXIN family" has been proposed.

The cloning of the mouse and human collagen 18 proteins has been described by Oh et al. (loc. cit.). The nucleotide and amino acid sequences of mouse collagen 18 are shown in accession number NM_001109991.1, whereas the corresponding human sequences are shown in NM_030582.3. Further, the amino acid sequences of mouse and human collagen 18 are shown in SEQ ID NOs: 1 and 2, respectively. The nucleotide and amino acid sequences of *Macaca mulatta* collagen 18 are shown in UniProt accession number I0FVB6. Preferably, collagen 18 as referred to herein is human collagen 18.

The "NC-1 domain" (or briefly NC-1 or NC1) as used herein is derived from or is from the C-terminus of collagen 18 and includes (i) an N-terminal association region (of about 50 amino acid residues), (ii) a central protease-sensitive hinge region (of about 70 amino acid residues) and/or (iii) a C-terminal stable endostatin domain (of about 180 amino acid residues) (Sasaki et al., 1998, *EMBO J.* 17, 4249).

A (poly) peptide "derived from" the NC-1 domain as used herein means that such a (poly) peptide is identical to or can differ from the corresponding amino acid sequence of the native (poly) peptide in the NC-1 domain, in one, two, three, four, five, six, seven, eight, nine, ten, 15, 20, 25, 30, 35, 40, 50 or even more amino acid residues, while at least maintaining (or even exceeding) the biological activity (as described elsewhere herein) of the corresponding NC-1 domain, such as the oligomerization properties, anti-angiogenic, anti-tumorigenic and/or anti-fibrotic activity. The mentioned term (poly) peptide "derived from" the NC-1 domain comprises variants of the NC-1 domain, as defined elsewhere herein.

The amino acid sequence of the NC-1 domain of the mouse collagen 18 is depicted in SEQ ID NO: 3, whereas the corresponding sequence of the NC-1 domain of human collagen 18 sequence is shown in SEQ ID NO: 4.

The "association domain" or "association region" (both terms are interchangeably) of the human NC-1 domain comprising amino acid residues from about 10 to about 60 of the amino acid sequence shown in SEQ ID NO: 4 is responsible for non-covalent trimerization of the NC-1 monomer to form a globular trimer. Accordingly, this association domain functions as a trimerization domain. The proteolytic cleavage-sensitive "hinge region" comprises amino acid residues from about 61 to about 129 of the amino acid sequence shown in SEQ ID NO: 4. The compact "endostatin domain" comprises amino acid residues from about 130 to about 308 of the amino acid sequence shown in SEQ ID NO: 4; see, e.g., Sasaki, loc. cit.; Kuo 2001, JCB 152, 1233; Tjin et al. 2005, *Cancer Res* 65, 3656. The endostatin domain comprises a zinc binding site which mediates binding to zinc and is located at the N-terminus of endostatin (Ding et al., 1998, *PNAS* 95, 10443; U.S. Pat. No. 7,524,811). Interestingly, this zinc binding site has been shown to be responsible for the anti-tumor/anti-angiogenic activity of endostatin (Boehm et al., 1998, *Biochem. Biophys. Res. Commun.* 252, 190). The association region and the endostatin domain in the NC-1 domain are connected by the hinge region (see Sasaki et al., loc. cit.). The hinge region has been found to be cleaved, for instance, by matrix metalloproteinases (MMPs), such as MMP-3, -7, -9, -13 and -20 (Heliasvaara et al., *Exp Cell Res* 2005, 307, 192).

The above-indicated domain structure of NC-1 is based on structural data. The term "about" as used for the positioning of the domains within NC-1 reflects the fact that the exact boundaries between the mentioned domains may differ from the indicated positions by one, two, three, four, five or even more amino acid residues. However, the exact boundary between, for example, the association domain and the hinge region can be determined by generating an association domain comprising amino acid residues from about 10 to about 60 of SEQ ID NO: 4 as a starting point, and producing shorter fragments thereof, e.g., with a length of 49, 48, 47, 46, 45 and so on, amino acid residues. Said shorter fragments can then be analyzed for their oligomerization properties, i.e. whether they are still able to form oligomers, such as trimers, as the complete association domain does.

Alternatively, the endostatin domain may serve as a starting point to address the oligomerization properties of the domains of NC-1. For example, a method for identifying the exact boundaries of the monomer, dimer and/or trimer transitions in the NC-1 domain as defined herein, can comprise: a) generating a series of recombinant peptides from or derived from the NC-1 domain, starting with a peptide consisting of the endostatin domain, followed by increasing the size of said peptide consisting of the endostatin domain in steps of about 10 to 20 amino acid residues, and b) testing the recombinant peptides of step a) for their oligomerization properties, i.e. whether said peptides are able to form dimers or trimers and identifying peptides which are able to form such oligomers, and c) determining the exact boundaries of the monomer, dimer and/or trimer transitions in the NC-1 domain. The method could comprise a further step d) of constructing an oligomer using the recombinant peptides identified in step b) which are able to form dimers or trimers. For generating a series of recombinant peptides from or derived from the NC-1 domain, peptide or protein synthesis known in the art can be used. For testing the oligomerization properties of protein oligomers or peptide oligomers as defined herein, for example, Western blot analysis, immunoprecipitation, SDS-PAGE, chromatographic methods or other methods well known in the art can be utilized; see, e.g., Sambrook et al., Molecular cloning: a laboratory manual/Sambrook, Joseph; Russell, David W.—3rd ed.—New York: Cold Spring Harbor Laboratory, 2001. Accordingly, the person skilled in the art is able to identify the exact boundaries of the monomer, dimer and/or trimer transitions in the NC-1 domain as defined herein, without undue burden. In addition, the above-mentioned domain model fits the gene structure remarkably well, with exons 38 and 39 encoding the association domain, exon 40 the hinge region, and three more exons the endostatin domain (Sasaki et al., loc. cit.).

The recombinant (poly) peptides generated by the above-indicated methods can be used to produce oligomers or fusion proteins, such as Fc fusion proteins, which form such oligomers and which can then further be tested for their anti-fibrotic activity, anti-angiogenic activity, anti-invasive/anti-metastatic activity, reducing vascular permeability activity, anti-inflammatory and/or anti-tumorigenic activity. An oligomer comprising such recombinant (poly) peptides or fusion proteins is particularly useful as a pharmaceutical composition for treating, ameliorating or preventing fibrosis or fibrosis-associated diseases, vascular endothelial growth factor (VEGF)-related diseases or matrix metalloproteinase (MMP)-related diseases, as defined elsewhere herein.

The term "NC-1 monomer of collagen 18" as referred to herein, comprises an oligomerization domain, a hinge region and/or an endostatin domain.

The term "oligomerization domain" as used herein refers generally to a protein domain which mediates the sub-unit assembly of the two or more NC-1 monomers, as defined herein. As indicated above, the oligomerization domain mediates dimerization, trimerization, or tetramerization and so on, of the NC-1 monomers. Such oligomerization leads, e.g., to functional advantages of multivalency and high binding strength, increased structure stabilization and combined functions of different domains, resulting in enhanced biological activity, such as improved or increased anti-fibrotic activity, anti-angiogenic activity, anti-invasive/anti-metastatic activity, reducing vascular permeability activity, anti-inflammatory and/or anti-tumorigenic activity, in comparison to the NC-1 monomer. The oligomerization domain can comprise, e.g., the association domain of the NC-1 domain mentioned above, i.e. the non-triple helical trimerization domain of collagen 18 which is responsible for non-covalent oligomerization of the NC-1 monomers or the collagen 18 helices. To give an example, the association domain of the human NC-1 domain can comprise amino acid residues from about 10 to about 60, preferably from amino acid residues 10 to 60, of the amino acid sequence shown in SEQ ID NO: 4, or peptides thereof. The association domain or peptides thereof are capable of mediating the non-covalent trimerization of the NC-1 monomer. The trimerization properties of the association domain or peptides thereof can be tested by methods mentioned elsewhere herein which are also known in the art (Sambrook, loc. cit.). In further aspects, the oligomerization domain can comprise other scaffold constructs/domains providing oligomerization and longer half life, well described in the literature; see, e.g. the review by Ali and Imperiali 2005, *Bioorganic and Medicinal Chemistry* 13, 5013. Such an oligomerization domain replaces structurally and functionally the association domain as found in the natural human NC-1 domain referred to above, or is used, in addition, to said association domain, in the protein or peptide oligomer. The oligomerization can alternatively be mediated by an Fc domain of an immunoglobulin, i.e. the oligomerization domain of the NC-1 monomer as defined herein comprises or is an Fc domain of an immunoglobulin. It is known in the art that fusion of an Fc domain to, e.g., a peptide or protein mediates a longer half life in circulation. It is to be understood that the Fc domain may be used in said NC-1 monomer, in addition to the association domain of the NC-1 domain mentioned above or may replace the association domain. The Fc domain confers a dimeric structure on the NC-1 monomer as defined herein since Fc is a dimer itself. In another aspect, the oligomerization can be mediated by the introduction of a structural modification, e.g., a mutation into the NC-1 monomer which results in the formation of disulfide bonds, as set forth in more detail below. It is further envisaged that the protein oligomers or peptide oligomers can be formed covalently.

The "hinge region" as referred to herein comprises amino acid residues from about 61 to about 129, preferably from amino acid residue 61 to 129, of the amino acid sequence shown in SEQ ID NO: 4, or peptides thereof. The hinge region or peptides thereof can comprise at least one endogenous proteolytic cleavage site such as an MMP-3, -7, -9, -13 or -20 cleavage site. Optionally, the hinge region within the NC-1 monomer of collagen 18 can comprise one or more recombinant protease cleavage sites, in addition to the endogenous protease cleavage sites of the hinge region. Such a recombinant protease cleavage site can be, for instance, an enterokinase, factor Xa or thrombin cleavage (Bergers and Javaherian; Lee et al.; loc. cit.). For example, cleavage by the respective protease allows for the release of the endostatin domain or fragments thereof such as (an) N-terminal endostatin peptide(s) from the protein oligomer or peptide oligomer. The hinge region or peptides thereof can comprise also more than one proteolytic cleavage site, such as two, three, four or even more proteolytic cleavage sites.

The hinge region can be interposed between the oligomerization domain and the endostatin domain or fragment(s) of said endostatin domain such as N-terminal endostatin peptides. Preferably, the hinge region is located between the oligomerization domain and the endostatin domain or fragment(s) thereof, in the NC-1 monomer as referred to herein. The domain arrangement within the NC-1 monomer of collagen 18 can be oligomerization domain-hinge region-endostatin domain or fragment(s) of said endostatin domain, or endostatin domain or fragment(s) of said endostatin domain-hinge region-oligomerization domain.

The mentioned NC-1 monomer can also comprise the oligomerization domain and an endostatin domain. In this case, the hinge region is missing.

The "endostatin domain of collagen 18" as used herein comprises amino acid residues from about 130 to about 308, preferably from 130 to 308, of the amino acid sequence shown in SEQ ID NO: 4. The corresponding amino acid sequence of said endostatin domain can be derived, for instance, from UniProtKB accession number P39060 (human) and P39061 (murine). Moreover, the endostatin domain of collagen 18 as used herein comprises SEQ ID NO: 18 in FIG. 2 which shows the amino acid sequence of murine endostatin; and SEQ ID NO: 19 in FIG. 2 which shows the amino acid sequence of human endostatin. Encompassed by the scope of the invention is also an endostatin domain of collagen 18 in which the glutamine at position 7 of SEQ ID NO: 18 or 19 is replaced by cysteine, resulting in an endostatin dimer covalently attached by a disulfide bond. If not otherwise specified, the term "endostatin" used herein refers to the endostatin domain of collagen 18.

The NC-1 monomer can also comprise a fragment of said endostatin domain, instead of the complete endostatin domain. For example, the fragment can be an N-terminal peptide of the endostatin domain of collagen 18, as defined herein. The NC-1 monomer comprises at least one N-terminal peptide of the endostatin domain of collagen 18 but can also comprise two, three, four or even more N-terminal endostatin peptides. The N-terminal endostatin peptides can be identical or different. Encompassed are linear, branched or cycled N-terminal endostatin peptides. For example, it is envisaged that two, three or more N-terminal endostatin peptides can be arranged in linear form. The endostatin domain or N-terminal peptide thereof has (at least) anti-fibrotic activity. In addition, the endostatin domain or N-terminal peptide thereof can have anti-angiogenic activity, anti-invasive/anti-metastatic activity, reducing vascular permeability activity, anti-inflammatory and/or anti-tumorigenic activity.

The term "N-terminal peptide of the collagen 18 endostatin domain" as used herein means a peptide from or derived from the amino (N or NH2)-terminus of the endostatin domain of collagen 18. The N-terminus of the endostatin domain of collagen 18 comprises amino acid residues from about amino acid residue 1 to about amino acid residue 132, preferably from amino acid residue 1 to amino acid residue 132, of SEQ ID NO: 18 (corresponding to the murine endostatin domain of collagen 18) or preferably SEQ ID NO: 19 (corresponding to the human endostatin domain of collagen 18). Further encompassed are shorter fragments thereof, i.e. at least two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120 or 130 amino acid residues. For example, polypeptide comprising amino acid residue 1 to amino acid residue 132, of SEQ ID NO: 19 (corresponding to the human endostatin domain of collagen 18) may serve as a starting point to address the anti-fibrotic activity, anti-angiogenic activity, anti-invasive/anti-metastatic activity, reducing vascular permeability activity, anti-inflammatory and/or anti-tumorigenic activity of such shorter fragments. Subsequently, a series of recombinant peptides from or derived from the human endostatin domain is generated, starting with a peptide consisting of the human endostatin domain, followed by reducing the size of said peptide consisting of the human endostatin domain in steps of about 5 to 20 amino acid residues, and analyzing these recombinant peptides for the mentioned activities. Tests for analyzing said biological activities are described elsewhere herein and known in the art. Preferably, the N-terminal peptide of the collagen 18 endostatin domain comprises or consists of the amino acid sequence shown in SEQ ID NO: 20 (murine) or SEQ ID NO: 22 (human); see also FIG. 2. In one aspect, the N-terminal peptide of the collagen 18 endostatin domain comprises an N-terminal endostatin peptide without change of the amino acid sequence, in comparison to the wild-type N-terminal endostatin peptide. Put it differently: The amino acid sequence of such peptide can be found in the native endostatin domain of NC-1. A "peptide derived from the N-terminus of the endostatin domain of collagen 18" comprises a peptide or peptide variant which can differ from the corresponding native endostatin peptide in the endostatin domain of NC-1, in one, two, three, four, five or even more amino acid residues, while at least maintaining (or even exceeding) the biological activity (e.g., anti-fibrotic activity, anti-angiogenic activity, anti-invasive/anti-metastatic activity, reducing vascular permeability activity, anti-inflammatory and/or anti-tumorigenic activity) of the corresponding endostatin peptide, in the endostatin domain of NC-1. Such a peptide is also referred to herein as an "N-terminal endostatin-derived peptide" or "variant of a N-terminal peptide of the collagen 18 endostatin domain" and is encompassed by the term "N-terminal peptide of the collagen 18 endostatin domain" as used herein. The peptide from or derived from the amino-terminus of the endostatin domain of collagen 18 can exhibit further modifications, as described elsewhere herein. For example, it can be fused to an Fc domain of an immunoglobulin or can contain another oligomerization domain as defined herein in order to mediate dimerization or oligomerization of the fusion protein. The fusion protein can include further therapeutic agents as mentioned elsewhere in this specification.

The term "treatment" as used herein denotes the improvement or even elimination of one or more symptoms associated with the disease as referred to herein, by the administration of a protein oligomer or peptide oligomer or fusion protein as defined herein to a subject in the need thereof.

The term "amelioration" as referred to herein means the act of making better or improving the disease as referred to herein in the subject, by administering the protein oligomer or peptide oligomer or fusion protein as specified herein. An improvement may also be seen as a slowing or stopping of the progression of the disease.

The term "prevention" as utilized herein means the avoidance of the occurrence or re-occurrence of the disease referred to herein, by the administration of a protein oligomer or peptide oligomer or fusion protein as defined herein.

The term "fibrosis-associated disease" as used herein denotes any disorder associated with fibrosis. The fibrosis-associated disease is preferably selected from the group consisting of: fibrosis of the skin, preferably scleroderma; keloid or keloid scar; hypertrophic scar; morphea; fibrosis as a result of graft-versus-host disease; subepithelial fibrosis;

endomyocardial fibrosis; uterine fibrosis; myelofibrosis; retroperitoneal fibrosis; nephrogenic systemic fibrosis; scarring after surgery; asthma; cirrhosis/liver fibrosis; fibrosis as a result of aberrant wound healing; glomerulonephritis; endometriosis, multifocal fibrosclerosis; radiation-induced fibrosis (as an example for stimulation-induced fibrosis), preferably radiation-induced pneumonitis or radiation-induced lung fibrosis; chemotherapy-induced or drug-induced fibrosis, e.g., as a result of mTOR or EGFR kinase inhibition; usual or idiopathic pulmonary fibrosis (as an example for idiopathic fibrosis); fibrosis as the result of autoimmune diseases, e.g., Lupus, intra-tumoral- and cancer-associated fibrosis/fibrogenesis, organ fibrosis-followed chronic inflammation (e.g., via viral stimulus or transplantation); organ fibrosis as the endstage of chronic kidney diseases, long term dialysis, or diabetes mellitus (PMID: 15939343, Common pathways in idiopathic pulmonary fibrosis and cancer, Eur Respir Rev 2013 22:265-272, Nat Rev Nephrol. 2014 Mar. 25. doi: 10.1038/nrneph.2014.31. PMID: 24662433 and PMID: 23938596, Nat Rev Nephrol. 2014 April; 10 (4): 226-37. doi: 10.1038/nrneph.2014.14. Epub 2014 Feb. 11. PMID: 24514753, Nat Rev Gastroenterol Hepatol. 2014 January; 11 (1): 4. doi: 10.1038/nrgastro.2013.227. Epub 2013 Nov. 26. PMID: 24275791).

Idiopathic pulmonary fibrosis (IPF) is a condition also known as cryptogenic fibrosing alveolitis (CFA) that is a chronic, progressive form of lung disease characterized by fibrosis of the supporting framework (interstitium) of the lungs. By definition, the term is used only when the cause of the pulmonary fibrosis is unknown ("idiopathic"). When lung tissue from patients with IPF is examined under a microscope by a pathologist, it shows a characteristic set of histologic/pathologic features known as usual interstitial pneumonia (UIP). UIP is characterized by progressive scarring of both lungs that involves the supporting framework (interstitium) of the lung.

The protein oligomer or peptide oligomer or fusion protein as referred to herein has at least anti-fibrotic activity. An "anti-fibrotic activity" as used herein means a biological activity which causes slowing down, stopping or even regression of fibrosis or a fibrosis-associated disease. Preferably, the fibrosis or fibrosis-associated disease is cured by the anti-fibrotic activity of the protein or peptide oligomer or fusion protein as defined herein. "Fibrosis" is the formation or development of excess fibrous connective tissue in an organ or tissue as a reparative or reactive process (e.g., in reaction to radiation and/or chemotherapy), contrary to a formation of fibrous tissue as a normal constituent of an organ or tissue. For example, treatment-related reductions in fibrosis can be associated with modulation of cytokines and growth factors.

The anti-fibrotic activity of a protein oligomer or peptide oligomer or fusion protein as defined herein can be tested, e.g., by animal models known in the art and shown in the following examples. For instance, bleomycin- and radiation-induced lung fibrosis models have been used to study lung fibrosis (Rubin, loc. cit.; Kamp, loc. cit. Gurujeyalakshmi et al. (1996), Res. Commun. Pharmacol. Toxicol. 1, p. 1-15; Gurujeyalakshmi et al. (1999), Am. J. Physiol. 276, p. L311-L318; Hallahan et al. (2002), J. Natl. Cancer Inst. 94, p. 733-741). Anti-fibrotic activity of a protein oligomer or peptide oligomer or fusion protein as specified herein can also be analyzed histologically (reduction or diminishing inflammation, granuloma formation and/or fibrosis), by analysis of expression of growth factors and/or cytokines (e.g., inhibition of PDGF-receptor activation, reduction of transforming growth factor-β, inhibition of receptor tyrosine kinase activation, reduction of IL-1β, KC, or TIMP-1), reduction of collagen, inhibition of fibroblast proliferation and fibroblast to myofibroblast transformation, and/or reduction of BAL lymphocytes, reduction of qualitative and quantitative surrogates of fibrosis (e.g. increase of lung density [Hounsfield units] and decrease of lung volume) using high resolution computer tomography, improved oxygen saturation (analysis of blood-gases, pulse-oximetry), Pulmonary Function Testing (PFT) and clinical symptoms (breath rate, heart rate, signs of right heart failure, diffusion capacity, Spirometry).

The term "vascular endothelial growth factor (VEGF)-related disease" as used herein denotes benign pathophysiological conditions depending on deregulation of the VEGF levels such as wet macular degeneration, endometriosis, bronchial asthma and diabetes mellitus, enhanced VEGF induced vascular permeability (e.g. enhanced permeability after irradiation of brain tissue, "radionecrosis"), alterations of vaso-tonus (e.g. hypertension), rheumatoid arthritis etc., as well as malignant VEGF dependent diseases such as renal cell cancer and other VEGF addicted tumors, VEGF dependent development of ascites, VEGF dependent suppression of immune system, e.g. recruitment and microenvironmental education of bone marrow-derived cells (BMDC), myeloid derived suppressor cells (MdSC), immature dendritic cells, etc. Preferably, the vascular endothelial growth factor (VEGF)-related disease is a VEGF-A-related disease.

The term "matrix metalloproteinase (MMP)-related disease" as referred to herein means benign and malignant diseases where MMP activation contributes to the pathophysiology, e.g., activation of MMPs during the process of local tumor invasion and cancer metastasis inherently evident in tumors with high local therapy failure rates such as glioblastoma, pancreatic cancer, lung cancer, as well as acquired enhanced MMP activation as the function of therapy induced selection pressures (e.g. tumor hypoxia and fibrosis post radiotherapy), overt immune reaction in auto-immune diseases and chronic inflammatory diseases etc. Preferably, the matrix metalloproteinase (MMP)-related disease is a MMP-2/MMP-9-related disease.

In a preferred embodiment, the protein oligomer or peptide oligomer or fusion protein as referred to herein has one, two or even more biological activities, in addition to the anti-fibrotic activity, wherein the additional biological activity is selected from the group consisting of: anti-angiogenic activity, anti-invasive/anti-metastatic activity, reducing vascular permeability activity, anti-inflammatory and anti-tumorigenic activity.

In addition to the anti-fibrotic activity, the protein oligomer or peptide oligomer or fusion protein as defined herein can have anti-angiogenic activity, anti-invasive/anti-metastatic activity, reducing vascular permeability activity, anti-inflammatory and/or anti-tumorigenic activity. Such activities include, for example, any biological activity inhibiting the growth or migration of endothelial cells and/or pericytes, formation of tubes or endothelium, growth of new capillary blood vessels in the body, slowing or inhibiting of the growth of benign or malignant tumors by cutting off their blood supply, reduce side-effects/toxicity of other anti-tumor or anti-angiogenic agents, e.g., VEGF-inhibitors, by interference with their mechanism of action, i.e. reduce blood pressure, modulation of inflammatory response in malignant and benign diseases, or improving the pathophysiological parameters, such as perfusion or hypoxia within a therapeutic time window after treatment that, in turn, may facilitate the efficacy of additional therapies (e.g., radiotherapy, chemotherapy or anti-apoptotic therapy). The anti-angiogenic activity can be tested by in vitro assays or in vivo by animal models known in the art (Abdollahi et al., *Cancer Res.* 2003, 63, 8890; *Mol. Cell* 2004, 13, 649; *PNAS* 2007, 104, 12890; *Drug Resist. Update* 2005, 8, 59; Bergers et al., *Science* 1999, 284, 808; Javaherian et al., *J. Biol. Chem.* 2002, 277, 45211; Lee et al., ('lin. *Cancer Res.* 2008). For instance, the anti-angiogenic activity can be tested in vitro by inhibition of the proliferation and/or migration of endothelial cells stimulated by a growth factor, e.g., by VEGF. In vivo anti-angiogenic activity can be analyzed, for example, by a chicken chorioallantoic membrane (CAM) assay, whereas an anti-tumor activity can be tested in animal tumor models including, e.g., A549, LLC or H460 non-small cell lung carcinoma, HT29 colon carcinoma, BxPC3 Pancreatic Carcinoma, Karpas 299 lymphoma, MOLM-13 AML (acute myeloid leukemia), 786-O, A2058 cell line (melanoma) or RENCA renal cell carcinoma (RCC) and many others (Abdollahi et al., *Drug Resist. Update* 2005, loc. cit.).

Medicaments for the therapy of a vascular endothelial growth factor (VEGF)-related disease which can be used in addition to the protein oligomer or peptide oligomer of fusion protein of the invention include, for example, other modulators of vascular permeability (e.g. enhanced permeability after irradiation of brain tissue. "radionecrosis") and vaso-tonus (e.g. endothelin antagonists macitentan, AT1/ACE inhibitors). ß2-sympathomimetics and corticoids in asthma, immune-suppressants in chronic inflammatory/auto-immune diseases, chemotherapy and radiotherapy for different VEGF-dependent tumors and ascites, kinase inhibitors used. e.g. in renal cell cancer (mTORi e.g., RAD001, multikinase inhibitors pazopanib/suitinib/axitinib, immune modulators. e.g. checkpoint inhibitors anti-PD-1/PD-L1 antibodies).

Medicaments for the therapy of a matrix metalloproteinase (MMP)-related disease which can be used in addition to the protein oligomer or peptide oligomer or fusion protein of the invention include. for example, locally invasive tumors with high loco-regional therapy failure rates treated with radio-(chemo)-therapy such as glioblastoma, pancreatic cancer, anti-inflammatory and immunosuppressive therapy (anti-TNF alpha antibodies/infliximab. mycophenolic acid. cyclophosphamide etc.), tumor invasion or pseudoprogression after cancer treatment, e.g. anti-angiogenic therapy in recurrent glioma. treatments of metastatic diseases with high MMP-2/-9 activity such as breast cancer (i.e. hormonal therapy tamoxifen. Trastuzumab in HER2+disease, chemotherapies).

The term "subject" as referred to in the present application pertains to a farm animal, a pet, a Macaque (such as *Macaca mulatta*) or a human. Preferably, the farm animal or pet is a mammal. More preferably, the subject is a human suffering from fibrosis or a fibrosis-associated disease, a vascular endothelial growth factor (VEGF)-related disease, or a matrix metalloproteinase (MMP)-related disease as defined herein, and, thus, is in the need for the treatment of the mentioned disease.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. As regards amino acid sequences, the term "about" means plus or minus 5 amino acid residues, 4 amino acid residues, 3 amino acid residues, 2 amino acid residues or 1 amino acid residue. Preferred is a range of plus or minus 10 percent; or plus or minus 3 or 1 amino acid residue(s).

The terms "comprising", "comprises" and "comprised of" as used herein are synonyms with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

The term "at least one" means one, two, three, four, five or even more.

It has been found by the present inventors in a previous study that trimeric NC-1 (with NC-1 comprising the association domain, the hinge region and the endostatin domain) derived from human collagen 18 binds Fibronectin, whereas endostatin monomer lacks binding to Fibronectin; see WO 2013/026913. Fibronectin is recognized as a major extracellular matrix protein, binding angiogenic and anti-angiogenic reagents. Endostatin is a monomer under physiological conditions. The major precursor to endostatin is NC-1, a trimeric molecule consisting of three interlinked chains, each with approximately 330 amino acids. This shows that NC-1 trimer has distinct properties, in comparison to endostatin. Furthermore, an Fc-endostatin which forms dimers as well as an artificial endostatin dimer bearing a single mutation in amino acid position 7 (glutamine to cysteine) of endostatin retains binding to Fibronectin indicating the importance of oligomerization for binding to Fibronectin. Following a search for endostatin-size molecules in human sera, the inventors failed to identify the conventional size endostatin (of about 20 kDa). The appearance of endostatin size molecules in human blood circulation might be due to the degradation of NC-1 trimer by proteases following collection of human sera. NC-1 trimer appeared to be the major physiological product of collagen 18 degradation, present in tissues and circulation showing distinct biological properties not shared by (monomeric) endostatin. The inventors further demonstrated high affinity binding of Fibronectin to VEGF, NC-1 trimer as well as co-immunoprecipitated these three candidate interaction partners from peripheral blood platelets protein lysates. Furthermore, in-vivo co-localization of NC-1 trimer, Fibronectin, VEGF and alpha 5 beta 1 ($\alpha 5\beta 1$) integrin could be demonstrated, suggesting a model in which an ensemble of VEGF, NC-1 trimer, integrin $\alpha 5\beta 1$ with Fibronectin prelude the initiation of the anti-angiogenic process. Most importantly, anti-tumor studies of NC-1 trimer versus endostatin showed that NC-1 trimer is a more potent anti-angiogenic protein than endostatin.

Unexpectedly, the inventors have found in a recent study, that fibrosis can be successfully treated by a protein oligomer exemplified by an Fc-endostatin fusion protein comprising an N-terminal endostatin peptide, as shown in the following examples. This result was surprising, in light of the teaching of WO 2011/050311 (loc. cit.) and the corresponding scientific publication by Yamaguchi et al. (Sci. Transl. Med. 2012, 4, p. 136ra71) in which anti-fibrotic activity has been reported only for C-terminal endostatin peptides from amino acid residues 133 to 180 (see E4 peptide). In contrast, no such activity could be shown for N-terminal endostatin peptides.

The finding by the present inventors that the N-terminal zinc binding region of endostatin known to be chiefly involved in its anti-angiogenic effects [Tjin, R. M., et al., *A 27-amino-acid synthetic peptide corresponding to the NH2-terminal zinc-binding domain of endostatin is responsible for its antitumor activity*. Cancer Research, 2005. 65 (9): p. 3656-3663] is also relevant for the anti-fibrotic effect elicited by this endogenous protein is in clear contrast to recently published data by Yamaguchi et al. (loc. cit.) postulating an anti-fibrotic effect of the C-terminal domain of endostatin. In the radiation induced lung fibrosis (RILF) model used by the present inventors, the C-terminal peptide was not effective to improve most investigated parameter of fibrosis development. Together, the data of the present inventors indicate an important role for the N-terminus sequence as well as dimerization of endostatin underlying its anti-fibrotic effect in the RILF model.

A closer look at the endostatin C-terminus, the E4 peptide containing area, shows no obvious structural feature linking this fragment with potential protein interaction partners that could provide a mechanistic explanation for the postulated anti-fibrotic effect of the molecule. Another explanation for the lack of E4 peptide activity might be that in contrast to the acute murine fibrosis models used by Yamaguchi et al., the present inventors utilized a radiation induced lung fibrosis model, where fibrosis development follows a slow (over 24 weeks after irradiation) and chronic kinetic more closely resembling the pathophysiology in humans.

In the further course of the study, the most efficient attenuation of lung fibrosis, however, was found by the present inventors when a synthetic endostatin dimer (Fc-endostatin) was utilized. Fc-endostatin (FcE) consists of two Fc chains (connected by disulfide bonds), extended to two molecules of endostatin each linked to a single Fc chain. Therefore, the two adjacent endostatin molecules become a dimer as a result of the Fc dimer.

Based on the data shown in the following Examples, the hypothesis by the present inventors is that the beneficial anti-fibrotic effect of the oligomeric endostatin is at least in part mediated by its property to bind Fibronectin, and this distinguishes the NC-1 oligomers or endostatin oligomers or oligomers comprising at least two N-terminal peptides of endostatin from monomers or monomeric fragments of NC-1 or endostatin.

In the present inventors' view, endostatin is an end-degradation product of NC-1. They present in the following Examples new data further demonstrating that the binding properties of endostatin dimer and NC1 trimer are quite distinct from endostatin monomer in terms of relevant protein interaction partners.

For example, it has been found that only oligomeric endostatin and NCI is able to bind fibronectin, VEGF, MMP-2 and MMP-9, but not monomeric endostatin; see also FIGS. 9 to 12.

In other words, it is the oligomerization properties of endostatin, endostatin peptides and NC1 which plays the key role in their binding to key players of tissue remodeling with high impact for exploration of its anti-fibrotic and anti-cancer effects.

It will be acknowledged by those skilled in the art that this important finding opens a new avenue for pursuing biological properties of oligomeric endostatin, oligomeric endostatin peptides or endostatin-derived peptides, either by synthetic design, e.g., dimerization via Fc or other alternatives to generate and improve a drug mimicking the endostatin precursor molecule NC1.

In one embodiment of the protein oligomer or peptide oligomer, the "NC-1 monomer" or "NC-1 monomer of collagen 18" as used herein comprises either the complete or at least one part of the non-collagenous NC-1 domain of collagen 18. Preferably, the NC-1 monomer is human.

As set forth elsewhere herein, the complete C-terminal NC-1 domain of collagen 18 includes an N-terminal association region, a central protease-sensitive hinge region and a C-terminal stable endostatin domain (Sasaki et al., 1998, *EMBO J.* 17, 4249). The at least one part of said NC-1 domain comprises at least one domain, region or fragment, of the non-collagenous NC-1 domain of collagen 18, preferably human collagen 18 as depicted in SEQ ID NO: 2. Preferably, the human NC-1 domain comprises or consists of SEQ ID NO: 4.

The NC-1 monomer as used herein comprises, in one aspect of the protein oligomer or peptide oligomer, at least one N-terminal peptide of the collagen 18 endostatin domain (briefly N-terminal endostatin peptide or N-terminal peptide) or at least one N-terminal endostatin-derived peptide of the collagen 18 endostatin domain.

Protein oligomer or peptide oligomer, collagen 18, the endostatin domain of collagen 18, N-terminal peptide of the collagen 18 endostatin domain, and N-terminal endostatin-derived peptide have already been defined elsewhere herein. Preferably, said oligomer, collagen 18, endostatin domain, N-terminal peptide or N-terminal endostatin-derived peptide is human.

Peptidomimetic and organomimetic embodiments are also envisioned, whereby the three-dimensional arrangement of the chemical constituents of such peptido- and organomimetics mimic the three-dimensional arrangement of the polypeptide backbone and component amino acid side chains, resulting in such peptido- and organomimetics of the endostatin domain, N-terminal endostatin peptide or N-terminal endostatin-derived peptide having measurable or enhanced anti-fibrotic activity. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, Pharmaceutical Biotechnology, Interpharm Press: Buffalo Grove, Ill., pp. 165-174 and Principles of Pharmacology, Munson (ed.) 1995, Ch. 102, for descriptions of techniques used in CADD. Also included are mimetics prepared using such techniques.

In one aspect, the N-terminal peptide or N-terminal endostatin-derived peptide comprises the complete zinc binding site/domain of the endostatin domain, i.e. comprises histidines 1, 3 and 11 and aspartic acid 76, of SEQ ID NO: 19. Preferably, the mentioned peptide comprises at least histidines 1, 3 and 11 of SEQ ID NO: 19.

In another aspect, the N-terminal peptide or N-terminal endostatin-derived peptide comprises the 27 amino acid-peptide described in Tjin, loc. cit., or fragments thereof. Preferably, the fragments of said 27 amino acid-peptide comprise at least histidines 1, 3 and 11.

Further examples of N-terminal peptides or N-terminal endostatin-derived peptides which can be used in the protein oligomer or peptide oligomer as used herein are shown in FIG. 2 and the following examples and comprise SEQ ID NO: 7, 9, 10, 13, 15, 18, 19, 20, or 22, or have been described in the literature, e.g., in Tjin et al., loc. cit., or in EP 1107989 B1 or U.S. Pat. No. 7,524,811.

Preferably, the endostatin-derived peptide or endostatin peptide is about 10 to about 40 amino acid residues in length, preferably 15 to 35, preferably 20 to 32, more preferably 24, 25, 26, 27, 28, 29 or 30 amino acid residues. For example, SEQ ID NO: 9 shows the corresponding murine sequence of the active motif of NC-1-endostatin domain (ED) (i.e., the amino-terminal zinc binding domain mediating anti-angiogenic and/or anti-tumor activity) with a length of 26 amino acid residues, whereas SEQ ID NO: 10 shows the corresponding human sequence with a length of 25 amino acid residues. The Histidine residues in these sequences are particularly important since it has been found by the present inventors in a previous study, that substitution of said Histidine residues by Alanine residues abolished anti-tumor and anti-angiogenic activity.

In preferred embodiments of the protein oligomer or peptide oligomer, the NC-1 monomer comprises or consists of the endostatin domain, as defined elsewhere herein. Preferably, the mentioned endostatin-derived peptide, endostatin peptide or endostatin domain comprises a single mutation of glutamine to cysteine at position 7 of the endostatin domain. Such mutants are able to form disulfide bridges and are, thus, able to form dimers; see, e.g., Kuo 2001, JCB 152, 1233; Tjin et al. 2005, *Cancer Res* 65, 3656. Accordingly, said mutation can be used in the protein or peptide oligomer described herein as a means for dimerization.

In a further embodiment, the NC-1 monomer comprises a hinge region, in addition to the endostatin domain, the endostatin-derived peptide, or the endostatin peptide. Such a construct will probably form a monomer, possibly a dimer. The formation of a dimer cannot be excluded since it appears that the hinge region may also contribute to the dimer association of such constructs. Optionally, such an NC-1 monomer comprises, in addition to the mentioned constituents, an association domain, i.e. the non-triple helical trimerization domain of human collagen 18, or another oligomerization domain as referred to herein. It is evident to those skilled in the art that the presence of the mentioned association domain results in the formation of a trimer. In another aspect, the NC-1 monomer comprises an endostatin domain and an association domain of the above-defined NC-1 domain and, in a still further aspect, an association domain, a hinge region and an endostatin domain, each of said NC-1 domain. In the latter aspect, the NC-1 monomer comprises the complete NC-1 domain of human collagen 18 or is, i.e. consists of, the NC-1 domain of human collagen 18 (of about 38 kDa). The NC-1 domain of human collagen 18 and the structure of said NC-1 domain has been defined, e.g., by Sasaki et al. (loc. cit.). The NC-1 domain of collagen 18 consists of a non-triple-helical sequence of 315 (mouse) or 312 (human) amino acid residues. As set forth above, the NC-1 domain has been found to associate non-covalently to form a trimer, via the above-mentioned association domain.

It is preferred that the NC-1 monomer as used herein is human.

Oligomerization of NC-1 is mediated by at least two domains of this protein: one consisting of approximately 50 amino acids at the N-terminal of the protein defining a triple-helix structure, i.e. the association domain. The second domain which participates in oligomerization is located at the N-terminus of endostatin and is able to bind to zinc. The human endostatin zinc site is formed by histidines 1, 3 and 11 and aspartic acid 76 of SEQ ID NO: 19. Said domain has been shown to form a dimer at high concentration of endostatin (Ding et al., loc. cit.). Thus, in certain aspects, the NC-1 monomer comprises the association domain and the N-terminus of the endostatin domain. It is also possible that the protease sensitive hinge region plays a role in oligomerization of NC-1, as already indicated above. Accordingly, in some aspects of the invention, the NC-1 monomer can further comprise a hinge region of the NC-1 domain.

The NC-1 monomer of the invention is preferably longer than 20, 30, 40, 50, 60, 70, 80, 90, 100, 110, 120, 130, 140, 150, 160, 170, 180, 190, 200, 210, 220, 230, 240, 250, 260, 270, 280, 290, 300, or 310 amino acid residues and is able to dimerize or oligomerize. Further, it has at least anti-fibrotic activity. In case the NC-1 monomer comprises the association domain, the hinge region and the zinc binding site/domain of endostatin domain or the complete endostatin domain, it is preferred that the NC-1 monomer is longer than 312 amino acid residues and comprises even more preferred at least 315, 320, 330, 340, 350, 400, 500 or even more amino acid residues.

In a further embodiment, the protein oligomer comprises at least two endostatin domains of collagen 18 but can include also three, four, five or even more endostatin domains.

For instance, Fc-endostatin (FcE) as used in Example 11 consists of two Fc chains (connected by disulfide bonds), extended to two molecules of endostatin each linked to a single Fc chain. Therefore, the two adjacent endostatin molecules become a dimer as a result of the Fc dimer. Another dimeric construct used in Example 11 comprised two endostatin domains of collagen 18. Each endostatin domain contained a single mutation at position 7 in which glutamine was replaced by cysteine. Each endostatin domain was linked to a Fc region of an immunoglobulin, with an intervening enterokinase cleavage site. In this construct, both Fc and endostatin were separately dimerized by their corresponding disulfide bonds. Enterokinase digestion of this recombinant protein resulted in an Fc dimer and an endostatin dimer. In another embodiment, the protein oligomer or peptide oligomer comprises at least two N-terminal peptides of the endostatin domain of collagen 18 but can include also three, four, five or even more of said N-terminal peptides.

The term "N-terminal peptide(s) of the collagen 18 endostatin domain" as used herein means a peptide from the amino-terminus of the endostatin domain of collagen 18. The definitions, explanations and embodiments as regards the NC-1 monomer and oligomerization thereof apply mutatis mutandis to the N-terminal peptide(s) of the collagen 18 endostatin domain. The N-terminus of the endostatin domain of collagen 18 comprises amino acid residues 1 to 132 of SEQ ID NO: 18 or 19 (corresponding to the endostatin domain of collagen 18). Preferably, the N-terminal peptide(s) of the collagen 18 endostatin domain is a endostatin peptide (without change of the amino acid sequence, in comparison to wild-type) or an endostatin-derived peptide as defined elsewhere herein.

In one embodiment, the N-terminal peptide of the collagen endostatin domain is or comprises an amino acid sequence from about amino acid residue 1 to about amino acid residue 132 of SEQ ID NO: 18 or 19 (endostatin domain of collagen 18).

The corresponding amino acid sequence of the endostatin domain of the murine collagen 18 is shown in SEQ ID NO: 18, whereas the corresponding amino acid sequence of the endostatin domain of the human collagen 18 is shown in SEQ ID NO: 19; see also FIG. 2. The term "N-terminal peptide of the collagen 18 endostatin domain" as referred to in this application comprises peptides located between about amino acid residues 1 (H; Histidine) and 132 (E; glutamic acid) of SEQ ID NO: 19, preferably between about amino acid residues 1 (H; Histidine) and 115 (P; Proline) of SEQ ID NO: 19, preferably between about amino acid residues 1 (H; Histidine) and 92 (G; Glycine), more preferably between about amino acid residues 1 (H; Histidine) and 76 (D; Aspartic acid) of SEQ ID NO: 19, even more preferably between about amino acid residues 1 (H; Histidine) and 27 (R; Arginine) of SEQ ID NO: 19 or between amino acid residues 1 (H; Histidine) and 25 (G; Glycine) of SEQ ID NO: 19. Examples for further N-terminal peptides of the collagen 18 endostatin domain are shown in Tjin et al., loc. cit., or in U.S. Pat. No. 7,524,811 or EP1668129 B1, incorporated herewith by reference. Preferably, the endostatin-derived peptide or endostatin peptide is about 10 to about 40 amino acid residues in length, preferably about 15 to 35, preferably about 20 to 32, more preferably about 24, 25, 26, 27, 28, 29 or 30 amino acid residues. Further preferred N-terminal peptides of the collagen 18 endostatin domain are illustrated, in the following examples.

The N-terminal zinc-binding domain of endostatin or a synthetic peptide corresponding to the N-terminal zinc-binding domain of endostatin is shown, for instance, in the amino acid sequences of SEQ ID NOs. 9 and 10. It is encompassed by the present invention, that variants of the amino acid sequences of SEQ ID NOs. 9 and 10, e.g., shorter amino acid sequences of SEQ ID NOs. 9 and 10 can be used as well. For example, the present inventors have found that a peptide corresponding to positions 1 to 13 of SEQ ID NO: 9 or positions 1 to 12 of SEQ ID NO: 10 can be used as endostatin peptide in the protein or peptide oligomer. In addition, such a peptide can differ from the corresponding endostatin peptide or endostatin-derived peptide in one, two, three, four or even more amino acid residues, while at least maintaining (or even exceeding) the anti-fibrotic activity (as described elsewhere herein) of the corresponding endostatin peptide in the endostatin domain of NC-1. In light of this, it is important to maintain the Histidine amino acid residues corresponding to positions 1, 3 and/or 11 of SEQ ID NOs. 9 or 10 for the reasons set forth elsewhere herein. Moreover, replacement of zinc by other similar divalent cations (i.e., copper) may result in more potent N-terminal peptides of endostatin, endostatin and NC-1 domains or monomers when compared with zinc.

The C-terminal endostatin polypeptides or peptides described in WO 2011/050311 and Yamaguchi et al. (*Sci. Transl. Med.* 2012, 4, p. 136ra71), i.e. peptides or polypeptides consisting of 40 consecutive amino acid residues of amino acid residues 133-180 of SEQ ID NO: 2, 4 or 13 in WO 2011/050311, and SEQ ID NO: 21 of the present application are excluded from the scope of the present invention. It is of further note that no anti-fibrotic activity could be shown for the N-terminal endostatin peptides E1 (amino acid residues 1 to 45) and E2 (amino acid residues 71 to 115), in the publication by Yamaguchi et al., in contrast to the findings of the present inventions; see the following Examples. In light of this, the findings in the present application are even more surprising.

The "NC-1 monomer of collagen 18", "endostatin domain of collagen 18" or the "N-terminal peptide of the collagen 18 endostatin domain" as defined herein can comprise additional protein domains or subunits, for instance, the above-mentioned Fc domains of immunoglobulins, or protein tags, for example, His tags, c-myc tags, Flag tags or the like, which can be used, e.g., for purification and/or detection. As well known in the art, protein tags are peptide sequences genetically grafted onto a recombinant protein. These tags can in one aspect be removable by chemical agents or by enzymatic means, such as proteolysis or intein splicing. Such tags are attached to the NC-1 monomer, endostatin domain of collagen 18 or N-terminal peptide of the collagen 18 endostatin domain as referred to herein. Affinity tags are appended to proteins so that they can be purified from their crude biological source such as a cell lysate using an affinity technique well known in the art. These include, for example, chitin binding protein (CBP), maltose binding protein (MBP), Fc domains of immunoglobulins or glutathione-S-transferase (GST). The poly (His) tag is a widely-used protein tag; it binds to metal matrices. Solubilization tags are used, especially for recombinant proteins expressed in chaperone-deficient species such as *E. coli*, to assist in the proper folding in proteins and keep them from precipitating. These include, e.g., thioredoxin (TRX) and poly-(NANP). Some affinity tags have a dual role as a solubilization agent, such as MBP, and GST. Chromatography tags are used to alter chromatographic properties of the NC-1 monomer, endostatin domain of collagen 18 or N-terminal peptide of the collagen 18 endostatin domain to afford different resolution across a particular separation technique. Often, these consist of poly-anionic amino acids, such as the FLAG-tag. Epitope tags are short peptide sequences which are chosen because high-affinity antibodies can be reliably produced in many different species. These are usually derived from viral genes, which explain their high immunoreactivity. Epitope tags include, for instance, V5-tag, c-myc-tag, and HA-tag. These tags are useful, e.g., for western blotting and immunoprecipitation experiments, although they also find use in protein purification. Fluorescence tags are used to give visual readout on a protein. GFP and its variants are the most commonly used fluorescence tags. More advanced applications of GFP include using it as a folding reporter (fluorescent if folded, colorless if not). Protein tags find many other usages, such as specific enzymatic modification (such as biotin ligase tags) and chemical modification (Flash tag). The various tags can also be combined to produce multifunctional modifications of the NC-1 monomer, endostatin domain of collagen 18 or N-terminal peptide of the collagen 18 endostatin domain.

The NC-1 monomer of human collagen 18, endostatin domain of collagen 18 or N-terminal peptide of the collagen 18 endostatin domain as defined herein can also comprise radioisotopes, e.g. $^{124}$I, $^{125}$I, $^{131}$I, Cu-64, Cu-67, Y-86, Zr-89, Y-90, Re-188, Ga-68; or radionuclides binding to chelates such as DTPA; toxins, e.g. Diphtheria toxin, or apoptosis inducing agents; or chemicals, e.g. chemotherapeutics such as taxols, or gemcitabine, which may be useful in improving and/or detecting the anti-fibrotic, anti-angiogenic and/or anti-tumorigenic activity of the protein oligomer.

In other embodiments, the protein or peptide oligomer is pegylated. Pegylation is the process of covalent attachment of polyethylene glycol (PEG) polymer chains to another molecule, normally a drug or therapeutic protein such as the protein or peptide oligomer as defined herein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins.

Pegylation of compounds is well known in the art; see, e.g., Damodaran and Fee 2010, *European Pharmaceutical Review* 15, 18.

The term "Fc region" or "Fc domain" as used herein means the fragment crystallizable region which is the tail region of an antibody or immunoblobulin that interacts with cell surface receptors, i.e. Fc receptors, and some proteins of the complement system. This property allows antibodies to activate the immune system. In IgG, IgA and IgD antibody isotypes, the Fc domain is composed of two identical protein fragments, derived from the second and third constant domains of the antibody's two heavy chains; IgM and IgE Fc domains contain three heavy chain constant domains (CH domains 2-4) in each polypeptide chain. The Fc domains of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. Fusion of the Fc domain of immunoglobulins to proteins has been found to enhance the production and secretion of the fusion proteins in mammalian cells (Lo et al., 1998, *Protein Eng.* 11, 495, Capon et al., 1989, Nature 337, 525). In addition, linking of angiogenesis inhibitors to an immunoglobulin Fc domain have shown to increase the half life of said inhibitors (Capon et al. 1989, Nature 337, 525; Gordon et al., 2001, *J. Clin. Oncol.* 19, 843; Holash et al., 2002, *Proc. Natl. Acad. Sci. USA* 99, 11393). However, the Fc domain can not only be used for purification, solubilization and/or detection purposes but alters advantageously the biological properties of the protein or peptide oligomer, as set forth herein below and in the following examples. In one embodiment, the one or more Fc domains can be cleaved off by treatment with proteases, such as enterokinase or thrombin, if desired. Preferably, the Fc domain as referred to herein is from human IgG (Bergers and Javaherian *Science* 1999; Lee et al *Clin Canc Res* 2008). As evident to those skilled in the art, in principle, any IgG isoform can be used to generate the oligomer of the invention. Even sub-fragments or single chains of the Fc domain of IgG can be used in order to prolong the half life or oligomerization of the oligomer described herein. The amino acid sequences of a mouse and human Fc domain which can be used for the generation of an oligomer or a fusion protein referred to herein, e.g. an Fc-NC-1 or NC-1-Fc fusion protein, or a Fc-endostatin or endostatin-Fc fusion protein, are shown in SEQ ID NOs: 5 and 6, respectively. Analogously, an N-terminal endostatin peptide-Fc fusion protein or an Fc-N-terminal endostatin peptide can be used, in the protein oligomer or peptide oligomer. Put in other words: The Fc domain can be positioned N- or C-terminally, in the fusion protein of the invention.

The protein oligomer or peptide oligomer, in an aspect, can be manufactured by chemical synthesis or recombinant molecular biology techniques well known to the person skilled in the art; see, e.g., Sambrook et al., Molecular cloning: a laboratory manual/Sambrook, Joseph; Russell, David W.—3rd ed.—New York: Cold Spring Harbor Laboratory, 2001.

For example, the protein oligomer or peptide oligomer can be generated by a method, comprising (a) culturing a host cell comprising a nucleic acid sequence encoding the protein oligomer or peptide oligomer, preferably under serum-free conditions, (b) obtaining from the host cell of step (a) the protein oligomer or peptide oligomer, and, optionally, (c) storing the protein oligomer or peptide oligomer, preferably under serum-free conditions. It has been found by the present inventors, that oligomeric NC-1 such as the NC-1 trimer is susceptible to degradation if kept in serum or cell culture media for longer periods of time, even at 4° C. Therefore, it is advantageous to produce and keep the protein oligomer or peptide oligomer under serum-free conditions. Alternatively, a polynucleotide encoding an NC-1 monomer of collagen 18, endostatin domain of collagen 18 or an N-terminal peptide of the endostatin domain of collagen 18 can be expressed under suitable conditions, in an appropriate host cell. Assembly of the mentioned NC-1 monomer, endostatin domain of collagen 18 or N-terminal endostatin peptide to dimers or oligomers occurs within the cell. Subsequently, the dimer or oligomer can be isolated and/or purified by methods known in the art (see, e.g., Sambrook, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1994)). For example, the protein oligomer or peptide oligomer can be obtained by conventional purification techniques from, e.g., a host cell lysate including, but not limited to, affinity chromatography, ion exchange chromatography, size exclusion chromatography and/or preparative gel electrophoresis. Alternatively, the mentioned NC-1 monomer, endostatin domain of collagen 18 or N-terminal endostatin peptide can be assembled to dimers or oligomers in vitro, after isolation and/or purification of the NC-1 monomer, endostatin domain of collagen 18 or N-terminal endostatin peptide from the cell.

In one embodiment, the protein or peptide oligomer binds to Fibronectin. In addition, the oligomer can bind to VEGF, preferably VEGF-A, MMP-2, MMP-9 and/or integrin alpha 5 beta 1. Said binding of the protein or peptide oligomer of the invention to Fibronectin, VEGF, MMP-2, MMP-9 and/or integrin alpha 5 beta 1 can be determined by methods known in the art such as immunoprecipitation, ELISA assays or Biacore.

In a further embodiment of the protein oligomer or peptide oligomer, the NC-1 monomer of human collagen 18 comprises an oligomerization domain, a hinge region and/or an endostatin domain or fragments of said endostatin domain. In some embodiments, the NC-1 monomer of human collagen 18 comprises an oligomerization domain, a hinge region and a complete endostatin domain. In other specific embodiments, the NC-1 monomer of human collagen 18 comprises an oligomerization domain, a hinge region and a fragment of the endostatin domain. The fragment of the endostatin domain is preferably an N-terminal fragment of the endostatin domain, more preferably an N-terminal peptide of the endostatin domain or a peptide derived from the N-terminus of the endostatin domain of collagen 18. The fragment of the endostatin domain comprises preferably at least one N-terminal endostatin peptide as defined herein, in the NC-1 monomer. The fragments of said endostatin domain can comprise also two, three, four or even more N-terminal endostatin peptides as defined herein, in the NC-1 monomer.

In another preferred embodiment of the protein oligomer or peptide oligomer, the hinge region is interposed between the oligomerization domain and the endostatin domain or fragment(s) of said endostatin domain. Preferably, the hinge region is located between the oligomerization domain and the endostatin domain or fragment(s) thereof, in the NC-1 monomer as referred to herein. The domain arrangement within the NC-1 monomer of human collagen 18 is preferably oligomerization domain-hinge region-endostatin domain or fragment(s) of said endostatin domain, or endostatin domain or fragment(s) of said endostatin domain-hinge region-oligomerization domain.

Optionally, the hinge region within the NC-1 monomer of human collagen 18 may comprise one or more recombinant protease cleavage sites, in addition or alternatively to the endogenous MMP protease cleavage sites of the hinge region. Such a recombinant protease cleavage site can be, for instance, an enterokinase or thrombin cleavage (Bergers and Javaherian; Lee et al.; loc. cit.; Lo et al., 1998, Protein Engineering 11 (6), 1998, p. 495-500). Said publications further describe appropriate linker regions that can be used for introducing the mentioned cleavage site(s), such as, e.g., poly-Glycine linkers and the like. Cleavage by the respective protease allows for, e.g., the release of the endostatin domain(s) of the protein oligomer or peptide oligomer.

In alternative embodiments, the NC-1 monomer as referred to herein lacks the hinge region.

In another embodiment of the protein oligomer or peptide oligomer, the NC-1 monomer of collagen 18, the endostatin domain of collagen 18 or the N-terminal peptide of the collagen 18 endostatin domain further comprises an RGD motif and/or PHSRN (SEQ ID NO: 31) motif of Fibronectin, preferably in a fusion protein. Preferably, the NC-1 monomer of collagen 18, the endostatin domain of collagen 18 or the N-terminal peptide of the collagen 18 endostatin domain comprise an RGD motif and a PHSRN (SEQ ID NO: 31) motif of Fibronectin.

For instance, SEQ ID NOs. 11 and 12 provide amino acid sequences comprising the RGD motif and surrounding amino acid residues important for binding of Fibronectin to integrins. Briefly, Fibronectin is recognized by integrins alpha 5 beta 1 and alpha V beta 3. The primary sequence motif of fibronectin for integrin binding is a tripeptide, Arg-Gly-Asp (RGD), located on the loop connecting the force-bearing G- and F-strands of FN-III10. Further involved in integrin binding of Fibronectin is the Pro-His-Ser-Arg-Asn (PHSRN) (SEQ ID NO: 31) motif which resides in the ninth domain of type III fibronectin.

The corresponding amino acid sequences of murine and human Fibronectin (FN) are shown, e.g., in accession numbers NP_034363.1 and NP_997647.1, respectively. The domain structure of human FN can be derived, e.g., from the publication by Wijelath et al. 2006, Circ. Res. 99, 853-860. Preferably, the RGD motif of Fibronectin comprises or consists of SEQ ID NO. 11, 12 or 17.

Preferably, the endostatin peptide or endostatin-derived peptide is located at the N-terminal end of the fusion protein and the RGD motif and/or PHSRN (SEQ ID NO: 31) motif of Fibronectin is located at the C-terminal end.

Preferably, such a fusion protein comprises an amino acid sequence as shown in SEQ ID NO: 7 or 13.

In another preferred embodiment, the fusion protein further comprises an Fc domain or an artificial oligomerization domain as defined herein. Preferably, the fusion protein with an artificial oligomerization domain comprises an amino acid sequence as shown in SEQ ID NO: 15. Preferably, the fusion protein comprises an Fc domain and an artificial oligomerization domain as defined herein Based on previous experimental data in WO 2013/026913, the present inventors hypothesized that oligomeric NC-1 may elicit its effects via Fibroncectin (FN). In addition to this, it has been found in the following Examples that oligomeric NC-1 and oligomeric endostatin bind to, VEGF and the matrix metalloproteinases MMP-2/MMP-9 which are important players in remodeling of extracellular matrix, in development of fibrosis, cancer progression and metastasis. Moreover, they found in WO 2013/026913 that FN is significantly down-regulated in tumors that become resistant to oligomeric NC-1 (Fc-Endostatin) after prolonged exposure, i.e. four serial in-vivo passages. Therefore, they postulated that loss of FN might constitute a key mechanism of inherent and acquired resistance to oligomeric NC-1. To proof this concept, a minimal peptide sequence has been engineered that mimics the key effects of the endostatin (ED)-Fibronectin complex. To this end, the inventors first selected the most active motif in the entire ED-domain consisting of a 27 amino acid-NH2-terminal region (Tjin Tham Sjin et al. 2005, Cancer Res. 65, 3656-63). Data by the present inventors indicated that this region itself may be capable of binding to VEGF and that the Histidines (Zinc binding domain) in this peptide sequence may be critical for VEGF binding. This is conceivable, because a mutated peptide in which the Histidines were replaced by Alanine residues failed to compete with VEGF-ED-dimer (Fc-Endostatin) binding. On the other hand, Fibronectin contains two active motifs that are critical for its binding to ITGA5B1, i.e. a PHSRN (SEQ ID NO: 31)- and a RGD-dependent motif. In order to mimic the physiological complex of oligomeric NC-1 and FN that mediated integrin signaling and other properties of the NC-1-ED, the inventors fused these two critical motifs, i.e. the above-mentioned most active motif in the NC-1-ED domain and the integrin-binding motif of Fibronectin comprising "RGD" and surrounding amino acid residues important for binding, and generated chimeric (or hybrid) fusion proteins called "Superstatins". For each fusion protein, a mouse and a human equivalent was designed. Using the murine (C57BL6) LLC (Lewis lung carcinoma) lung cancer model, the inventors were able to show the efficacy of the murine Superstatin peptide to potently inhibit tumor growth. In addition, Superstatin significantly prolonged survival as compared to control. In contrast, the FN-Motif alone showed no significant improvement in prevention of tumor growth.

The corresponding amino acid sequence for the murine (m) Superstatin is shown in SEQ ID NO: 7, whereas the corresponding amino acid sequence for the human (h) Superstatin is shown in SEQ ID NO: 13. Superstatins are likely monomers. SEQ ID NO: 15 shows a variant of the human Superstatin amino acid sequence which is able to dimerize, due to the substitution of Glutamine at position 7 in SEQ ID NO: 13 by Cysteine. Additional constructs containing the PHSRN (SEQ ID NO: 31) instead of the RGD motif of FN, as well as constructs facilitating dimerization of the Superstatin via disulfide bounds or Fc regions will be prepared and evaluated with respect to anti-fibrotic activity.

In a further embodiment of the protein oligomer or peptide oligomer, the NC-1 monomer of human collagen 18, the endostatin domain of collagen 18 or the N-terminal peptide of the collagen 18 endostatin domain comprises a native or heterologous oligomerization domain.

Preferably, the native oligomerization domain is a non-triple helical trimerization domain of human collagen 18.

Preferably, the heterologous oligomerization domain is an oligomerization domain selected from the group consisting of an Fc domain and an artificial oligomerization domain.

The oligomerization domain as referred to herein can comprise a non-triple helical trimerization domain of human collagen 18 (, i.e. the association domain), an Fc domain or an artificial oligomerization domain. The oligomerization domain comprises in one aspect a native oligomerization domain, i.e. a non-triple helical trimerization domain of human collagen 18 which is responsible for trimerization of the three chains of the NC-1 domain. In another aspect, it comprises a heterologous oligomerization domain, e.g. an Fc domain from an antibody or immunoglobulin. The Fc domain confers a dimeric structure on the NC-1 monomer, endostatin domain or the N-terminal peptide of the endostatin domain as defined herein since the Fc domain is a dimer itself. In a third aspect, it comprises an artificial oligomerization domain, for example, point mutations to cysteins resulting in disulfide bridges between two monomers which replaces structurally and functionally the association domain as found in the natural human NC-1 referred to above, or is used in addition to said association domain or Fc domain. Other means and methods for dimerization or oligomerization have been described elsewhere herein and are known in the art including, e.g., coiled coils, leucine zipper, CovX body technology etc. and are comprised by the term "heterologous oligomerization domain" or "artificial oligomerization domain" as used herein. It is also encompassed by the scope of the invention, that the oligomerization domain of the protein oligomer comprises a non-triple helical trimerization domain of human collagen 18 and a Fc domain. Further, it can comprise an artificial oligomerization domain and a Fc domain. For instance, one of the dimeric constructs used in Example 11 comprised two endostatin domains of collagen 18. Each endostatin domain contained a single mutation at position 7 in which glutamine was replaced by cysteine. Each endostatin domain was linked to a Fc region of an immunoglobulin, with an intervening enterokinase cleavage site. In this construct, both Fc and endostatin were separately dimerized by their corresponding disulfide bonds. Enterokinase digestion of this recombinant protein resulted in an Fc dimer and an endostatin dimer.

Preferably, the Fc domain is from IgG or other immunoglobulin isoforms as well as other scaffold constructs providing oligomerization and longer half life described in the art; see, e.g., Lo et al., Protein Engineering 1998, 11, 495. A murine Fc domain is shown, for example, in SEQ ID NO: 5. More preferably, the Fc domain is from a human IgG, even more preferred from human IgG1. Particularly preferred, the human Fc domain comprises or consists of an amino acid sequence as shown in SEQ ID NO: 6 or SEQ ID NO: 24.

In another preferred embodiment, the Fc domain is a "knobs-into-holes" (KiH) engineered Fc domain. Knobs-into-holes is a well-validated heterodimerization technology for the third constant domain of an antibody. Basically, the concept relies on modifications of the interface between the two CH3 domains where most interactions occur. A bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges. During the process of optimizing the heterodimerization interface, various rational designs, including steric complementarity, KiH, disulfide bonds and salt bridges juxtaposing oppositely charged residues on either side of the CH3 domain, were evaluated and ultimately optimized using a phage display library. Correct heavy chain association with heterodimerization yields above 97% can be achieved by introducing six mutations: S354C, T366W in the "knob" heavy chain and Y349C, T366S, L368A, Y407V in the "hole" heavy chain (Klein et al., MAbs. 2012 Nov. 1; 4 (6): 653-663; Ridgway et., Protein Eng. 1996 July; 9 (7): 617-21). In addition, properties of antibodies with KiH mutations such as (thermal) stability, FcγR binding and effector functions (e.g., ADCC, FcRn binding) and pharmacokinetic (PK) behavior are not affected. The noncovalent interactions, along with disulfide bridges in the hinge region, drive assembly toward heterodimer formation and minimize combinatorial heterogeneity. The production of NC-1 using conventional approaches suffers from low protein yields. Further, also production of NC-1 fused to Fc is no trivial task because of the formation of a number of different aggregations. Such heterogeneity is unwanted in pharmaceutical compositions, as appreciated by those skilled in the art. The KiH technology can be used to produce NC-1 as a monomer and avoids the formation of such heterogeneous aggregations (such as a mixture of NC-1 dimers, trimers, tetramers, pentamers and the like). Suitable KiH-engineered Fc domains are depicted, e.g., in SEQ ID NOs. 25, 26, 28 and 30. For example, SEQ ID NO: 25 shows the amino acid sequence of the human IgG1 Fc with the "knob" mutations S354C/T366W, and SEQ ID NO: 26 depicts the amino acid sequence of the human IgG1 Fc with the "hole" mutations Y349C/T366S/L368A/Y407V.

SEQ ID NO: 27 shows the amino acid sequence of a fusion protein comprising human NC-1 fused via an enterokinase cleavage site and a linker to the human IgG1 Fc with "knob" mutations (S354C/T366W) (from N- to C-terminus). This fusion protein is able to heterodimerize with the human IgG1 Fc with "hole" mutations Y349C/T366S/L368A/Y407V (SEQ ID NO: 28). Such a heterodimer is illustrated in FIG. 14B. Cleavage of the heterodimer by enterokinase results in the generation of NC-1 monomer. The NC-1 monomer can then be used for the generation of NC-1 dimers or NC-1 trimers. Evidently, endostatin can be used, instead of NC-1, if monomeric endostatin shall be produced.

SEQ ID NO: 29 shows the amino acid sequence of a fusion protein comprising human IgG1 Fc with "knob" mutations (S354C/T366W) fused via a linker and an enterokinase site to human NC-1 (from N- to C-terminus). This fusion protein is able to heterodimerize with the human IgG1 Fc with "hole" mutations Y349C/T366S/L368A/Y407V (SEQ ID NO: 30). Such a heterodimer is illustrated in FIG. 14A. Cleavage of the heterodimer by enterokinase results in the generation of NC-1 monomer. Obviously, endostatin can be used, instead of NC-1, if monomeric endostatin shall be produced.

"Knobs-into-holes" (KiH)-engineered Fc domains are particularly useful for the production of NC-1 monomers or endostatin monomers, for the above-indicated reasons. Accordingly, it is preferred that KiH-engineered Fc domains of human immunoglobulins, more preferably KiH-engineered Fc domains of human IgG1 be used for the production of the protein oligomer, peptide oligomer or fusion protein of the invention.

In another embodiment, a NC-1 monomer of collagen 18 and a Fc region of an immunoglobulin is expressed together with a Fc region of an immunoglobulin in a cell to avoid uncontrolled aggregation of the NC-1. This approach results in the formation of a Fc-Fc dimer with one Fc connected to the NC-1 monomer. If a protease (such as thrombin or enterokinase) cleavable linker is interposed between the Fc and NC-1 monomer, the NC-1 monomer can be released from the heterodimer upon cleavage with the respective protease. A similar approach can be used for the generation of an endostatin monomer.

In a still further embodiment, it can be appropriate to omit or mutate the native N-terminal association region in the NC-1 domain so that NC-1 cannot oligomerize any longer via its natural association region. For example, a series of recombinant NC-1 domains can be produced in which the native association region is subsequently reduced by, e.g., 3, 5 or 10 amino acid residues. Then they are tested for their oligomerization properties in order to identify NC-1 variants that are no longer able to oligomerize via their native association region. For testing the oligomerization properties of said variants, Western blot analysis, immunoprecipitation, SDS-PAGE, chromatographic methods or other methods well known in the art can be utilized. The recombinant polypeptides generated by the above-indicated method can be used to produce protein oligomers or fusion proteins of the invention which can then further be tested for their biological activity as defined herein. In another embodiment, amino acid residues required for the association are identified by structural analyses (e.g. computational or 3D structural analysis like SAPIN) and then mutated accordingly by recombinant methods known in the art (see Sambrook and Russell, 2001, loc. cit.) so that the NC-1 cannot oligomerize any longer. In another embodiment, the native N-terminal association region in the NC-1 domain can be omitted completely. If a NC-1 domain without functional association region is fused to a Fc region, such a monomer can be used for the production of a NC-1 dimer wherein dimerization is mediated via the Fc region. The protein oligomer of the invention can comprise at least one, or two or more of NC-1 monomers of human collagen 18 with such alterations or deletions in the native N-terminal association region, as defined elsewhere herein.

The oligomerization domain of the NC-1 monomer, endostatin domain or the N-terminal peptide of the endostatin domain can be a Fc domain of an immunoglobulin, preferably a Fc domain from IgG1, or a KiH-engineered Fc domain from IgG1, as set forth above. The protein oligomer or peptide oligomer can also contain two, three or even more Fc domains. In one aspect, the Fc domain(s) may be cleaved off the protein oligomer or peptide oligomer, if desired. For instance, an artificial protease cleavage site such as an enterokinase or a thrombin cleavage site can be interposed between the NC-1 monomer or endostatin domain and the Fc domain(s) in the protein oligomer or peptide oligomer, for example, via a corresponding (poly) peptide linker (see, e.g., Bergers and Javaherian; Lee et al.; loc. cit.; Lo et al., 1998, Protein Engineering 11 (6), 1998, p. 495-500). Upon cleavage by the respective protease, the oligomer is released from the Fc domain(s).

The Fc domain(s) can also be used for purification and/or detection. In addition, the Fc domain alters the biological properties of the protein oligomer, such as half-life extension in circulation and improvement of biological activity, preferably improvement of the anti-fibrotic, anti-angiogenic activity and/or anti-tumor activity. For example, it has been found that an Fc-endostatin fusion protein is able to bind Fibronectin as a dimer, whereas endostatin monomer does not, as demonstrated in the following Examples. Moreover, Fc-endostatin shows a longer half life than endostatin.

In a further preferred embodiment of the protein oligomer or peptide oligomer, the artificial oligomerization domain comprises a single mutation at position 7 of the endostatin domain in which glutamine is replaced by cysteine. Preferably, the NC-1 monomer, the endostatin domain or N-terminal peptide of the endostatin domain as defined herein comprises in some aspects a single mutation of glutamine to cysteine at position 7 of the endostatin domain. For example, it has been found that a recombinantly introduced enterokinase cleavage site between the Fc domain and endostatin domain in a fusion protein results in the formation of a dimer upon enterokinase cleavage because of disulfide bond formation between adjacent C7 residues in the endostatin domains; see Kuo 2001, *JCB* 152, 1233 and the following Examples. As set forth above, NC-1 trimer and endostatin dimers have distinct properties, in comparison to the endostatin monomer. The above mutation at position 7

(glutamine to cysteine) can also be introduced in the N-terminal peptide of endostatin which has been shown to represent the anti-tumor domain of endostatin (Tjin et al. 2005, *Cancer Res* 65, 3656). The oligomerization of the N-terminal peptide of the endostatin domain can be achieved by either artificial dimerization as described above or simply by recombinant fusion to the Fc moiety without a mutation in position 7. An example for a fusion protein comprising said mutation at position 7 mediating dimerization is shown in SEQ ID NO: 15.

In another preferred embodiment of the protein oligomer or peptide oligomer, the recombinant protease cleavage site within the hinge region is an enterokinase or thrombin cleavage site.

The cleavage of the protein oligomer or peptide oligomer with the enterokinase or thrombin results in the release of the endostatin domains from the protein oligomer or peptide oligomer.

In a further preferred embodiment of the protein oligomer or peptide oligomer, the NC-1 monomer as defined herein contains only a protease cleavage site naturally occurring within the hinge region, i.e. it does not comprise a recombinant protease cleavage site. In this case, the hinge region can be cleaved, e.g. by MMPs, as set forth elsewhere herein, in order to release, e.g., the endostatin domain(s), from the NC-1 monomer. In another aspect, these naturally occurring protease cleavage sites in the hinge region of the NC-1 monomer can be mutated so that NC-1 monomer is no longer cleaved by said proteases. In this way, e.g., the half-life, anti-fibrotic, anti-angiogenic and/or anti-tumor activity of the protein oligomer may still be improved.

In another preferred embodiment of the protein oligomer or peptide oligomer, the oligomer is a dimer or a trimer. However, encompassed by the protein oligomer or peptide oligomer are also tetramers or pentamers or oligomers with even more NC-1 monomers, endostatin domains or N-terminal peptides of the endostatin domain, as defined herein.

A pharmaceutical composition comprising the protein oligomer or peptide oligomer as pharmaceutical active compound can be used for non-human or, preferably, human therapy of fibrosis or fibrosis-associated diseases, in a therapeutically effective dose. The pharmaceutical composition of the invention can be also used for therapy of a vascular endothelial growth factor (VEGF)-related disease or a matrix metalloproteinase (MMP)-related disease. The "subject" as referred to herein is preferably a human suffering from fibrosis or a fibrosis-associated disease, a vascular endothelial growth factor (VEGF)-related disease or a matrix metalloproteinase (MMP)-related disease.

Preferably, the fibrosis-associated disease is selected from the group consisting of: fibrosis of the skin, preferably scleroderma; keloid or keloid scar; hypertrophic scar; morphea; fibrosis as a result of graft-versus-host disease; subepithelial fibrosis; endomyocardial fibrosis; uterine fibrosis; myelofibrosis; retroperitoneal fibrosis; nephrogenic systemic fibrosis; scarring after surgery; asthma; cirrhosis/liver fibrosis; fibrosis as a result of aberrant wound healing; glomerulonephritis; multifocal fibrosclerosis; radiation-induced fibrosis (as an example for stimulation-induced fibrosis), preferably radiation-induced pneumonitis or radiation-induced lung fibrosis; chemotherapy-induced or drug-induced fibrosis, e.g., as a result of mTOR or EGFR kinase inhibition; usual or idiopathic pulmonary fibrosis (as an example for idiopathic fibrosis); fibrosis as the result of autoimmune diseases, e.g., Lupus, intra-tumoral- and cancer-associated fibrosis/fibrogenesis, organ fibrosis-followed chronic inflammation (e.g., via viral stimulus or transplantation); organ fibrosis as the endstage of chronic kidney diseases, long term dialysis, or diabetes mellitus.

Preferably, the vascular endothelial growth factor (VEGF)-related disease is selected from the group consisting of: benign pathophysiological conditions depending on deregulation of the VEGF levels such as wet macular degeneration, endometriosis, bronchial asthma and diabetes mellitus, enhanced VEGF-induced vascular permeability (e.g., enhanced permeability after irradiation of brain tissue, "radionecrosis"), alterations of vaso-tonus (e.g. hypertension), rheumatoid arthritis, as well as malignant VEGF-related diseases such as renal cell cancer and other VEGF-addicted tumors, VEGF-dependent development of ascites, VEGF-dependent suppression of immune system, e.g. recruitment and microenvironmental education of bone marrow-derived cells (BMDC), myeloid derived suppressor cells (MdSC), or immature dendritic cells.

Preferably, the matrix metalloproteinase (MMP)-related disease is selected from the group consisting of: benign and malignant diseases where MMP activation contributes to the pathophysiology, e.g., activation of MMPs during the process of local tumor invasion and cancer metastasis inherently evident in tumors with high local therapy failure rates such as glioblastoma, pancreatic cancer, lung cancer, as well as acquired enhanced MMP activation as the function of therapy induced selection pressures (e.g. tumor hypoxia and fibrosis post radiotherapy), overt immune reaction in autoimmune diseases and chronic inflammatory diseases.

In an aspect, the protein oligomer or peptide oligomer can be present in liquid or lyophilized form. In an aspect, the protein oligomer or peptide oligomer can be present together with glycerol, protein stabilizers (e.g., human serum albumin (HSA)) or non-protein stabilizers.

The protein oligomer or peptide oligomer is the active ingredient of the pharmaceutical composition or medicament (both terms are used interchangeably), and is in one aspect, administered in conventional dosage forms prepared by combining the drug with standard pharmaceutical carriers according to conventional procedures. These procedures may involve mixing, granulating, and compressing, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables. The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pennsylvania.

The diluent(s) is/are selected so as not to affect the biological activity, preferably, anti-fibrotic activity, anti-angiogenic activity, anti-invasive/anti-metastatic activity, reducing vascular permeability activity, anti-inflammatory and/or anti-tumorigenic activity of the pharmaceutical composition. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

The protein oligomer or peptide oligomer is preferably formulated as a pharmaceutical composition which can be administered by standard routes. Generally, the pharmaceutical composition may be administered by the topical, transdermal, intraperitoneal, intracranial/intrathecal, intravitreal, intracerebroventricular, intracerebral, intravaginal, intrauterine, oral, rectal or parenteral (e.g. intravenous, intraspinal, subcutaneous or intramuscular) route.

Preferably, the protein oligomer or peptide oligomer is administered intravenously, subcutaneously, intracranial/intrathecal, intravitreal, or intraperitoneally.

A therapeutically effective dose refers to an amount of the protein oligomer or peptide oligomer to be used in a pharmaceutical composition which prevents, ameliorates or treats the symptoms accompanying the disease referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Preferably, the protein oligomer or peptide oligomer is administered in a concentration from about 1 to 100 mg/kg. More preferably, the concentration is from about 5 to 75 mg/kg or from about 10-50 mg/kg, most preferably about 15 mg/kg. Even more preferred, the protein oligomer or peptide oligomer is administered at a concentration of 0.1-1 mg/kg/day.

The medicament or pharmaceutical composition referred to herein is administered at least once in order to treat or ameliorate or prevent the disease recited in this specification. However, the said medicament may be administered more than one time, e.g., two, three, four, five, six times or even more frequently.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

The pharmaceutical composition may in a further aspect of the invention comprise drugs in addition to the protein oligomer which are added to the medicament during its formulation. For example, it can be used together with angiostatin, in a combination regimen. Further, combinations with recently approved modulators of fibrosis such as VEGF/PDFG RTKi (e.g. Nindetanib), specific and non-specific inhibitors of TGF-beta-signaling (Perfinidone) and modulators of integrin signaling (cilengitide, or anti alphaV abituzumab) or inflammation (leukocyte infiltration, cytokine inhibitors, antibodies against subpopulations) are envisaged, in another aspect. Medicaments for the therapy of a vascular endothelial growth factor (VEGF)-related disease which can be used in addition to the protein oligomer or peptide oligomer include, for example, other modulators of vascular permeability (e.g. enhanced permeability after irradiation of brain tissue, "radionecrosis") and vaso-tonus (e.g. endothelin antagonists macitentan, AT1/ACE inhibitors), β2-sympathomimetics and corticoids in asthma, immunesuppressants in chronic inflammatory/auto-immune diseases, chemotherapy and radiotherapy for different VEGF dependent tumors and ascites, kinase inhibitors used e.g. in renal cell cancer (mTORi e.g., RAD001, multikinase inhibitors pazopanib/suitinib/axitinib, immune modulators e.g. checkpoint inhibitors anti PD-1/PD-11). Medicaments for the therapy of a matrix metalloproteinase-related disease which can be used in addition to the protein oligomer or peptide oligomer include, for example, locally invasive tumors with high loco-regional therapy failure rates treated with radio-(chemo)-therapy such as glioblastoma, pancreatic cancer, anti-inflammatory and immunosuppressive therapy (anti-TNF alpha antibodies/infliximab, mycophenolic acid, cyclophosphamide etc.), tumor invasion or pseudoprogression after cancer treatment e.g. anti-angiogenic therapy in recurrent glioma, treatments of metastatic diseases with high MMP-2/MMP-9 activity such as breast cancer (i.e. hormonal therapy tamoxifen, Trastuzumab in HER2+disease, chemotherapies).

Thus, in preferred embodiments of the protein oligomer or peptide oligomer, said oligomer further comprises angiostatin (U.S. Pat. No. 8,206,718). In specific embodiments, the angiostatin is an Fc-angiostatin or angiostatin-Fc fusion protein, preferably human fusion protein.

It is to be understood that the formulation of a pharmaceutical composition takes place under GMP standardized conditions or the like in order to ensure quality, pharmaceutical security, and effectiveness of the medicament.

As evident from the above, it is preferred that the protein oligomer, peptide oligomer and fusion protein is or is composed of human sequences.

The invention further pertains to a protein oligomer comprising (i) at least two NC-1 monomers of human collagen 18 or (ii) at least two endostatin domains of collagen 18 or (iii) at least two N-terminal peptides of the collagen 18 endostatin domain, for use for detecting and/or diagnosing fibrosis or a fibrosis-associated disease, a vascular endothelial growth factor (VEGF)-related disease or a matrix metalloproteinase-related disease.

The definitions and embodiments provided as regards the medical uses of the protein oligomer or peptide oligomer apply mutatis mutandis to the diagnostic application and uses of the invention.

The term "detecting" as utilized herein means to discover or ascertain the existence or presence of fibrosis or a fibrosis-associated disease, a vascular endothelial growth factor (VEGF)-related disease or a matrix metalloproteinase-related disease, in a subject.

The term "diagnosing" as referred to in this description means to recognize fibrosis or a fibrosis-associated disease, a vascular endothelial growth factor (VEGF)-related disease or a matrix metalloproteinase-related disease, in a subject by examination. Diagnosis as used herein is to be understood as medical diagnosis which refers to both the process of attempting to determine or identify a possible disease and diagnosis in this sense can also be termed (medical) diagnostic procedure, and to the opinion reached by this process also being termed (medical) diagnostic opinion.

Detecting and diagnosing of fibrosis or a fibrosis-associated disease, a vascular endothelial growth factor (VEGF)-related disease or a matrix metalloproteinase-related disease, in a subject can be carried out by methods known in the art such as computer tomography (e.g., high resolution computed tomography), ultrasound, blood analysis (e.g. blood gas analysis, acid-basic balance), analysis of biological markers such as proteinases (MMPs), growth factors and/or cytokines, histopathology (collagen deposition, inflammatory response markers), clinical tests (organ function, e.g. restrictive lung diseases test FEVI etc., organ dysfunction), cellular tests, invasive (surgical biopsy) and non-invasive tests, other invasive and non-invasive examinations such as MRI, PET/CT and the like, or a combination thereof (see, e.g., Raghu et al. 2011, Am. J. Respir. Crit. Care Med. 183, p. 788-824).

For example, the accuracy of diagnosis of idiopathic pulmonary fibrosis (IPF) increases with clinical, radiologic, and histopathologic correlation and can be accomplished with a multidisciplinary discussion among experienced clinical experts in the field.

For detecting and/or diagnosing fibrosis or a fibrosis-associated disease, a vascular endothelial growth factor (VEGF)-related disease or a matrix metalloproteinase-related disease, the NC-1 monomers of human collagen 18, the endostatin domain of collagen 18 or the N-terminal peptides of the collagen 18 endostatin domain can be labeled with radioisotopes, radionuclides binding to chelates such as DTPA, fluorescent proteins or other labels described elsewhere herein.

For example, the human Superstatin peptide (SEQ ID NO: 13) can be conjugated to the complexing agent 1,4,7, 10-tetraazacyclododecane-1,4,7,10-tetraacetic acid (also known as DOTA) providing the ability to conjugate the peptide with, e.g., radionuclides such as Gallium (68Ga) for non-invasive imaging (Positron emission tomography, PET). In-vivo PET-Imaging evaluating the potential of Superstatin-DOTA as agent for diagnosing a fibrosis-associated disease, a vascular endothelial growth factor (VEGF)-related disease or a matrix metalloproteinase-related disease, is envisioned.

Thus, preferably, the human Superstatin peptide (SEQ ID NO: 13) is conjugated to the complexing agent 1,4,7,10-tetraazacyclododecane-1,4,7,10-tetraacetic acid (also known as DOTA).

The invention also relates to fusion proteins comprising at least one NC-1 domain of collagen 18, at least one endostatin domain of collagen 18 or a (n) N-terminal peptide(s) of the collagen 18 endostatin domain for use in diagnosing, preventing, treating or ameliorating fibrosis or fibrosis-associated diseases, a vascular endothelial growth factor (VEGF)-related disease or a matrix metalloproteinase-related disease.

The definitions and embodiments provided as regards the medical uses of the protein oligomer or peptide oligomer apply mutatis mutandis to the therapeutic or diagnostic application and uses of the fusion protein of the invention.

Suitable and preferred protein oligomers, fusion proteins, NC-1 domains of collagen 18, endostatin domains of collagen 18 and N-terminal peptide(s) of the collagen 18 endostatin domain are defined elsewhere herein and shown in the Figures and the examples. Preferably, said fusion proteins comprise SEQ ID NO: 3, 4, 7, 9, 10, 13, 15, 18, 19, 20, 22, 27 or 29, or N-terminal peptide(s) of the collagen 18 endostatin domain described in Tjin et al., loc. cit., or in U.S.

Pat. No. 7,524,811. Preferred Fc sequences are depicted in SEQ ID NO. 6, 24, 25, 26, 28 or 30.

It is required that the fusion proteins of the invention are able to dimerize or oligomerize via an oligomerization domain as defined elsewhere herein. As set forth elsewhere herein, this dimerization or oligomerization is a prerequisite for the binding of the fusion protein to Fibronectin, VEGF, integrins, MMP-2 and MMP-9, and possibly further binding partners not yet unraveled so far. Preferably, the oligomerization domain is an Fc domain (preferably from or derived from IgG, more preferably human IgG, even more preferably human IgG1) and/or an artificial oligomerization domain, as specified elsewhere herein. Furthermore, the fusion protein has preferably anti-fibrotic activity, anti-inflammatory, anti-invasive/metastatic, reducing vascular permeability, anti-angiogenic activity and/or anti-tumorigenic activity. It is also preferred that the fusion protein comprises one or more RGD motifs and/or PHSRN (SEQ ID NO: 31) motifs of Fibronectin, as defined in this specification. It is further preferred that the fusion protein is human.

The invention further describes polynucleotides encoding the NC-1 monomer, endostatin domain of collagen 18 or N-terminal peptide(s) of the collagen 18 endostatin domain and pertains to polynucleotides encoding the fusion proteins of the invention.

The term "polynucleotide" or "nucleic acid" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequences encoding the NC-1 monomer, endostatin domain of collagen 18 or N-terminal peptide(s) of the collagen 18 endostatin domain or a fusion protein comprising said monomer or peptide, a polynucleotide may comprise additional sequences required for proper transcription and/or translation such as 5'- or 3'-UTR sequences. In light of the degeneracy of the genetic code, optimized codons may be used in the nucleic acid sequences encoding the NC-1 monomer, endostatin domain of collagen 18 or N-terminal peptides of the collagen 18 endostatin domain or a fusion protein comprising said monomer or peptide. Thereby, optimal expression in, e.g., a host cell can be achieved.

It will be understood that the present invention also encompasses variants of such specific amino acid sequences of the NC-1 monomer, endostatin domain of collagen 18 or N-terminal peptides of the collagen 18 endostatin domain or nucleic acid sequences encoding them as long as these variant sequences also allow for the formation of a protein or peptide oligomer. Said variants have preferably anti-fibrotic activity, and can have also anti-angiogenic and/or anti-tumor activity as defined elsewhere herein. In an aspect, a sequence variant as used herein differs from the specific amino acid sequence or a specific nucleic acid sequence as specified before by one or more amino acid or nucleotide substitutions, additions and/or deletions. In another aspect, the said variant sequence is at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identical to the specific nucleic acid sequence or amino acid sequence of the NC-1 monomer, endostatin domain of collagen 18 or N-terminal peptide(s) of the collagen 18 endostatin domain over the entire length or over at least a stretch of half of the length of the specific sequence.

Preferably, the said variant sequence is at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identical to the specific amino acid sequence of the human NC-1 monomer or domain as shown in SEQ ID NO: 4 or the mouse NC-1 monomer or domain as shown in SEQ ID NO: 3, over the entire length. It is also preferred that the said variant sequence is at least 50%, at least 60%, at least 70%, at least 80%, at least 85%, at least 90%, at least 91%, at least 92%, at least 93%, at least 94%, at least 95%, at least 96%, at least 97%, at least 98% or at least 99% identical to the sequences depicted in SEQ ID NO: 7, 9, 10, 13, 15, 18, 19, 20, 22, 27 or 29 over the entire length. The term "identical" as used herein refers to sequence identity characterized by determining the number of identical amino acids between sequences wherein the sequences are aligned so that the highest order match is obtained. It can be calculated using published techniques or methods codified in computer programs such as, for example, BLASTP or FASTA (Altschul 1990, *J Mol Biol* 215, 403). The percent identity values are, in one aspect, calculated over the entire amino acid sequence or over a sequence stretch of at least 50% of the query sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, *CABIOS* 5, 151) or the programs Gap and BestFit (Needleman 1970, *J Mol Biol* 48; 443; Smith 1981, *Adv Appl Math* 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

The invention further describes a vector comprising the polynucleotide encoding the NC-1 monomer, endostatin domain of collagen 18 or N-terminal peptide(s) of the collagen 18 endostatin domain or a fusion protein comprising said monomer, domain or peptide.

Preferably, the vector is an expression vector.

The term "vector" encompasses preferably phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, in an aspect, comprise DNA of sufficient length for either homologous or heterologous recombination as described in detail below. The vector encompassing the mentioned polynucleotide, in an aspect, further comprises selectable markers for propagation and/or selection in a host cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

Moreover, in an aspect, the above-indicated polynucleotide is operatively linked to expression control sequences allowing expression in prokaryotic or eukaryotic host cells or isolated fractions thereof in the said vector. Thus, in an aspect, the vector is an expression vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GALI-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotide or vector into a targeted cell population. Methods which are well known to those skilled in the art can be used to construct recombinant viral vectors; see, for example, the techniques described in Sambrook, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1994).

The invention further describes a host cell comprising the polynucleotide encoding the NC-1 monomer, endostatin domain of collagen 18 or N-terminal peptide(s) of the collagen 18 endostatin domain or a fusion protein comprising said monomer or peptide, or the vector containing such polynucleotide.

The term "host cell" as used herein as used herein encompasses prokaryotic and eukaryotic host cells. In an aspect the host cell is a bacterial cell. In one aspect, the said bacterial host cell is an *E. coli* host cell. Such a bacterial host cell may be used, e.g., for reproduction of the mentioned polynucleotide or vector.

A eukaryotic host cell, in an aspect, is a cell which comprises the polynucleotide encoding the NC-1 monomer, endostatin domain of collagen 18 or N-terminal peptide(s) of the collagen 18 endostatin domain, or a fusion protein comprising said monomer, domain or peptide, or the vector wherein said polynucleotide or vector are expressed in the host cell in order to generate the protein or peptide or oligomer thereof. The polynucleotide may be introduced into a host cell either transiently or stably. In an aspect, the eukaryotic host cell may be a cell of a eukaryotic host cell line which stably expresses the polynucleotide. In another aspect, the host cell is a eukaryotic host cell which has been transiently transfected with the polynucleotide or vector and which expresses the polynucleotide. In another aspect, the said cell is a cell which has been genetically engineered to produce the protein or peptide. How such cells can be genetically engineered by molecular biology techniques is well known to the skilled person.

The present invention also relates to a kit comprising the protein oligomer or fusion protein of the invention.

The term "kit" as used herein refers to a collection of the protein oligomer or fusion protein of the present invention which may or may not be packaged together. It is required that the fusion protein is able to oligomerize, as explained elsewhere herein. The kit can encompass further components for formulating the protein oligomer or fusion protein of the present invention as a pharmaceutical or diagnostic composition. The components of the kit may be comprised by separate vials (i.e. as a kit of separate parts) or provided in a single vial. Moreover, it is to be understood that the kit of the present invention is to be used for the therapy or diagnosis of the diseases referred to herein above. In one aspect, it is envisaged that all components are provided in a ready-to-use manner for practicing the therapeutic or diagnostic uses referred to herein. In a further aspect, the kit contains instructions for carrying out the said uses. The instructions can be provided by a user manual in paper- or electronic form.

The present invention further pertains to the use of the protein oligomer or fusion protein of the invention for generating and, preferably, improving a pharmaceutical composition mimicking NC1.

In addition, the present invention relates to the use of the protein oligomer or fusion protein of the invention for the development of NC1-mimetics or mimetics of oligomeric endostatin for the treatment or diagnosis of fibrosis-related diseases, VEGF-related diseases, or MMP-related diseases, as defined herein.

Finally, the present invention relates to the use of the protein oligomer or fusion protein of the invention for the development of NC1-mimetics or mimetics of oligomeric endostatin for the modulation of fibronectin function.

What is to be understood by mimetics has been explained elsewhere herein.

Fibronectin (FN) is a pleiotropic molecule with a number of activities and binding partners in matrix remodeling, immune response, invasion, and epithelial-to-mesenchymal transition. The more it is understood how the oligomer of the invention interacts with Fibronectin function, the more specific those functions can be targeted. For example, if the protein oligomer of the invention binds to the same heparin binding site of FN (heparin binding site II) as also VEGF does, it can be analyzed what is the implication if FN is being trapped for VEGF binding or what is the effect for binding to integrins or MMPs. FN does a number of effects that are differentially modulated by NC1. The more is known about these modulations, the better they can be targeted the way nature intended via NC-1.

Particularly preferred protein oligomers, peptide oligomers and fusion proteins for the medical and diagnostic uses of the invention are depicted in the Figures and examples. Sequences The sequences show:

SEQ ID NO: 1: murine Collagen 18
SEQ ID NO: 2: human Collagen 18

SEQ ID NO: 3: NC-1 domain of murine Collagen 18
SEQ ID NO: 4: NC-1 domain of human Collagen 18
SEQ ID NO: 5: murine Fc domain
SEQ ID NO: 6: human Fc domain
SEQ ID NO: 7: murine Superstatin
SEQ ID NO: 8: murine Fibronectin motif
SEQ ID NO: 9: murine N-terminal zinc-binding domain Endostatin
SEQ ID NO: 10: human N-terminal zinc-binding domain Endostatin
SEQ ID NO: 11: murine RGD motif
SEQ ID NO: 12: human RGD motif
SEQ ID NO: 13: human Superstatin
SEQ ID NO: 14: human Superstatin with His at positions 1 and 3 replaced by Ala
SEQ ID NO: 15: human Superstatin with Gln at position 7 replaced by Cys
SEQ ID NO: 16: human Superstatin with "RGD" motif replaced by "RAD" motif
SEQ ID NO: 17: murine integrin-binding motifs of Fibronectin
SEQ ID NO: 18: mEndostatin (murine)
SEQ ID NO: 19: hEndostatin (human)
SEQ ID NO: 20: mP1 peptide (murine; N-terminal)
SEQ ID NO: 21: E4 peptide of Endostatin (human; C-terminal)
SEQ ID NO: 22: hP1 peptide of Endostatin (human; N-terminal)
SEQ ID NO: 23: Enterokinase cleavage site
SEQ ID NO: 24: Fc sequence of wildtype human IgG1
SEQ ID NO: 25: Fc sequence "knob" human IgG1 Fc: S354C/T366W
SEQ ID NO: 26: Fc sequence "hole" human IgG1 Fc Y349C/T366S/L368A/Y407V
SEQ ID NO: 27: NC-1-enterokinase site-linker-human IgG1 Fc with "knob" mutations (S354C/T366W)
SEQ ID NO: 28: Human IgG1 Fc with "hole" mutations Y349C/T366S/L368A/Y407V
SEQ ID NO: 29: Human IgG1 Fc with "knob" mutations (S354C/T366W)-linker-enterokinase site-NC-1
SEQ ID NO: 30: Human IgG1 Fc with "hole" mutations Y349C/T366S/L368A/Y407V SEQ ID NOs: 1-17 are also depicted in WO 2013/026913, the disclosure content of which is incorporated herewith by reference. The amino acid sequence of human Fibronectin is shown in UniProt accession number PO2751. The amino acid sequence of the human matrix metalloproteinase-2 (MMP-2) is shown in UniProt accession number P08253. The amino acid sequence of the human matrix metallopro- teinase-9 (MMP-9) is shown in UniProt accession number P14780. The amino acid sequence of human vascular endothelial growth factor (VEGF-A) is shown in UniProt accession number P15692. The recognition and cleavage site of enterokinase and appropriate linker regions are described, e.g., in Lo et al., 1998, *Protein Engineering* 11 (6), 1998, p. 495-500.

FIGURES

The Figures show:

FIG. 1. The topology of collagen XVIII and Fc-endostatin as well as physiological size of endostatin molecules in different tissues. (A) The structures of collagen XVIII con- sists of a signal peptide, frizzled domain, triple helical repeats, NC1 domain. The ES motif is physiologically trimerized in the context of NC1. (B) Schematic of synthesis of two ES domain to IgG Fc domain. (C,D) The contents of endostatin were found in mouse brain, skeletal muscle, heart, kidney, testis and liver tissue extracts and serum by immunoblot. Images reproduced from Kuo, C. J., et al., *Oligomerization-dependent regulation of motility and morphogenesis by the collagen XVIII NCI endostatin domain.* J Cell Biol, 2001. 152 (6): p. 1233-46.; Sasaki, T., et al., *Structure, function and tissue forms of the C-terminal globular domain of collagen XVIII containing the angiogenesis inhibitor endostatin.* EMBO J, 1998. 17 (15): p. 4249-56.] In FIG. 1D, the sequence XXHLRPARP is SEQ ID NO: 32, PARPXSPPAH is SEQ ID NO: 33, and SPPAHSHRDF is SEQ ID NO: 34.

FIG. 2. The sequences of endostatin, N-terminal peptides (mP1) and (hP1) and C-terminal E4 (CE4) peptide.

Figure 3:
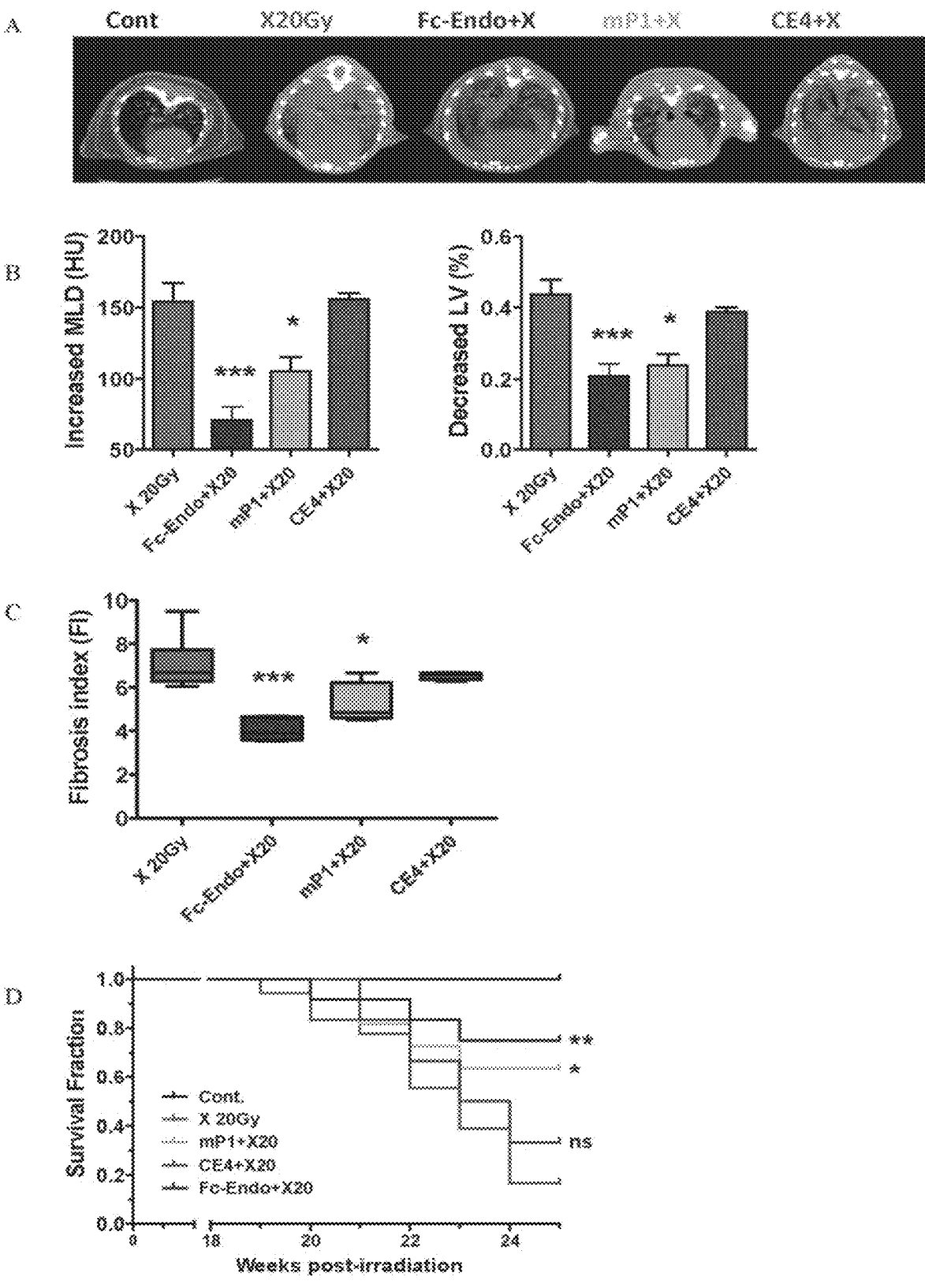

FIG. 3. Reduced radiation induced lung fibrosis development after Fc-Endo and mP1-treatment. (A) Micro-CT imaging of control and treatment groups at the end point of 24 weeks post irradiation. Massive fibrosis was found in mice that received sham photon irradiation (X-20Gy), with limited effective ventilation space left in the lung. Interstitial fibrosis was also significant in irradiated lung after CE4 treatment (CE4+X). Much clear lung parenchyma was found in irradiated lungs treated with mP1-Endo (mP1+X) and particularly Fc-Endo-treated mice (Fc-Endo+X). (B) Quantitative clinical CT measurement found a significantly reduced mean lung density (MLD) as well as total lung volume (LV) loss in Fc-Endo+X and mP1-Endo+X groups, respectively. (C) The fibrosis indices (FIs) of Fc-Endo+X and mP1-Endo+X treatment groups were significantly decreased compared to that of the IR-only group (X20Gy). There was no statistical difference between the CE4-Endo+X treatment and IR-only groups. (D) Great survival benefits were found for the Fc-Endo+X and mP1-Endo+X groups but not for the CE4+X treated group (*P<0.05, P<0.01, *P<0.001, ns=not statistically significant).

Figure 4:
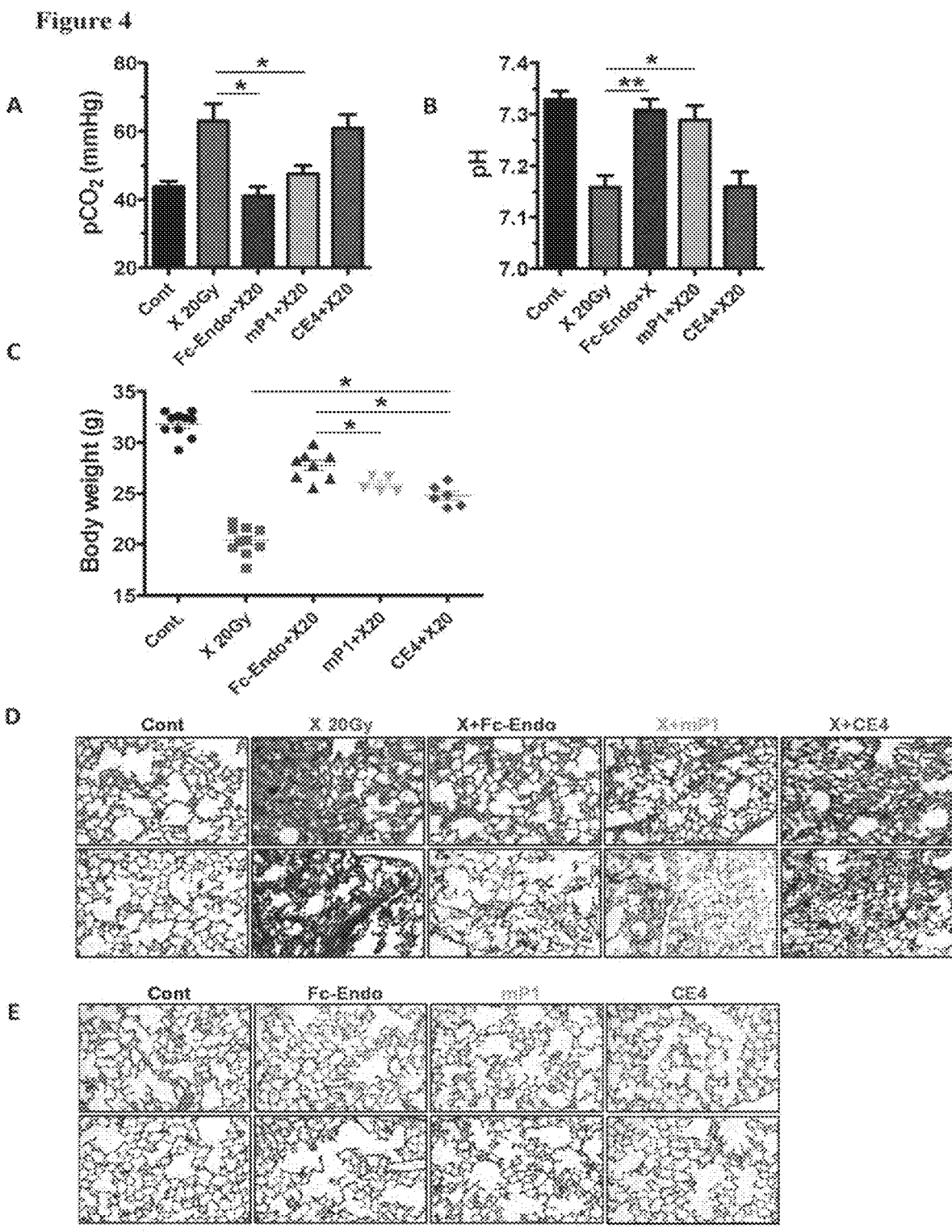

FIG. 4. Improved clinical parameter and pathohistological presentation after Fc-Endo and mP1-Endo treatment in irradiated lungs. (A, B) Blood gas analysis demonstrated an increased partial pressure of carbon dioxide ($pCO_2$) in the blood and decreased level of pH (acidosis) in IR-only (X-20Gy) group at the end point of 24 weeks after irradiation. $PCO_2$ and pH levels of mice treated with Fc-Endo+X or mP1-Endo+X were significantly ameliorated. (C) All treatment groups containing endostatin polypeptide fragments benefited in terms of weight gain. Among those, Fc-Endo was found to have the most significant improvement. (D) Histopathological examination confirmed significantly reduced inflammation and fibrosis in Fc-Endo+X and mP1-Endo+X treatment groups. (E) No histopathological difference was found among non-irradiated Fc-Endo, mP1-Endo and CE4-Endo treatment groups (*P<0.05, P<0.01, *P<0.001).

Figure 5:
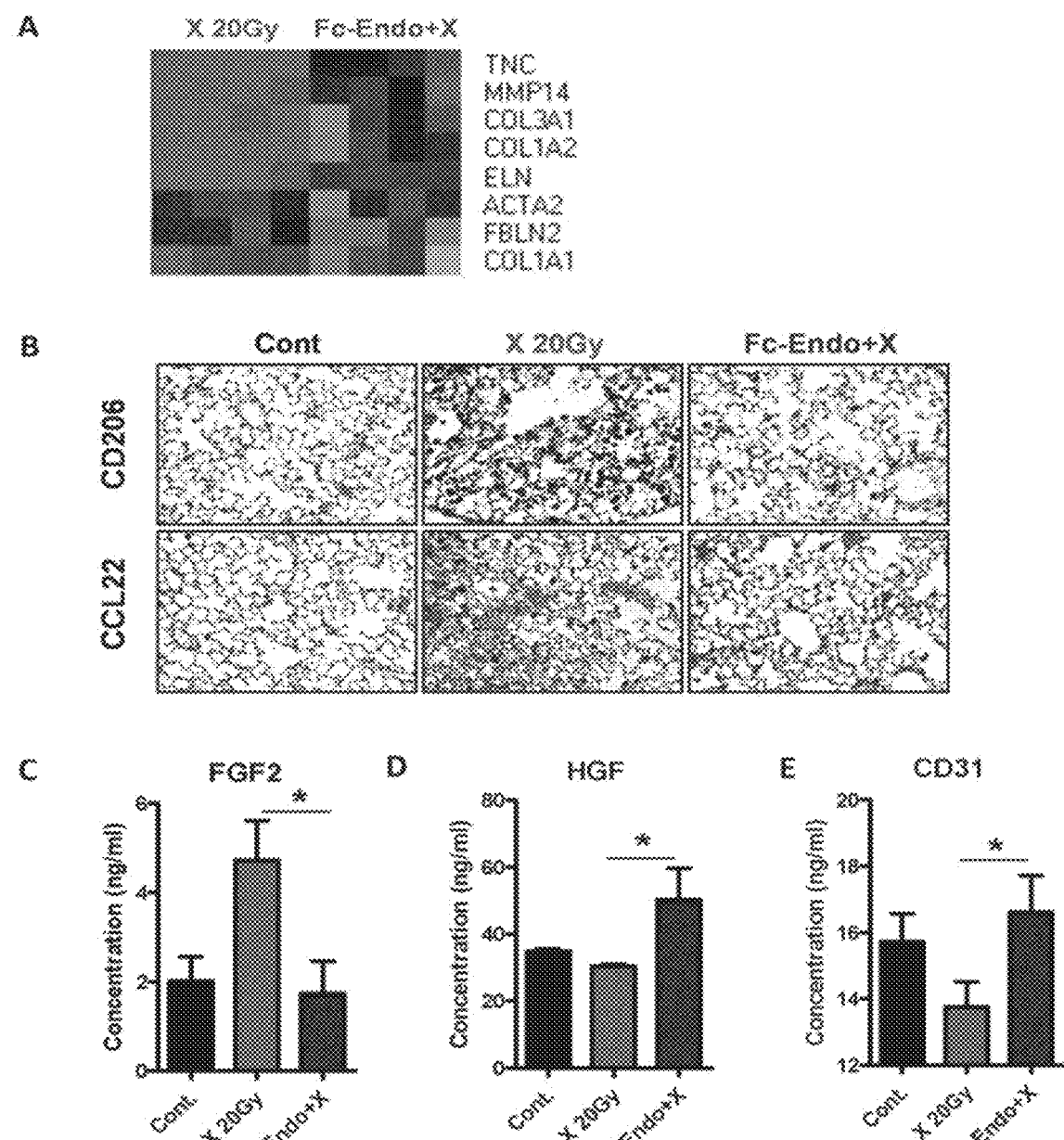

FIG. 5. M2 polarization, gene- and protein expression after Fc-Endo+X treatment. (A) The transcription signatures of ECM proteins were suppressed by Fc-Endo+X treatment. (B) Fc-Endo was also found to attenuate radiation induced pro-fibrotic M2 macrophage polarization. (C) Fc-Endo treatment reversed radiation induced FGF2- and loss of CD31 expression. In contrast, the expression of anti-fibrosis HGF was increased by Fc-Endo+X vs. X20Gy treatment. (*P<0.05, P<0.01, *P<0.001).

FIG. 6. Fc-Endo reduced fibrosis after high-LET carbon irradiation. (A) Micro-CT imaging at the end point of 24 weeks post irradiation. Massive fibrosis was found in mice irradiated with carbon-ion 12.5 Gy (C12.5), with limited effective ventilation space left in the lung. However, the lung architecture was well preserved in mice treated with Fc-Endo+C12.5. (B) Quantitative clinical CT measurement showed a significantly reduced mean lung density (MLD) as well as total lung volume (LV) loss in the Fc-Endo+C12.5-vs. C12.5-group. (C) The fibrosis indices (FIs) of Fc-Endo+C12.5 treatment group were significantly lower than the FIs of the C12.5 alone group. (D) Pathohistological examination confirmed significantly reduced inflammation and fibrosis after Fc-Endo+C12.5 vs. carbon irradiation alone (*P<0.05, P<0.01, *P<0.001).

Figure 7:
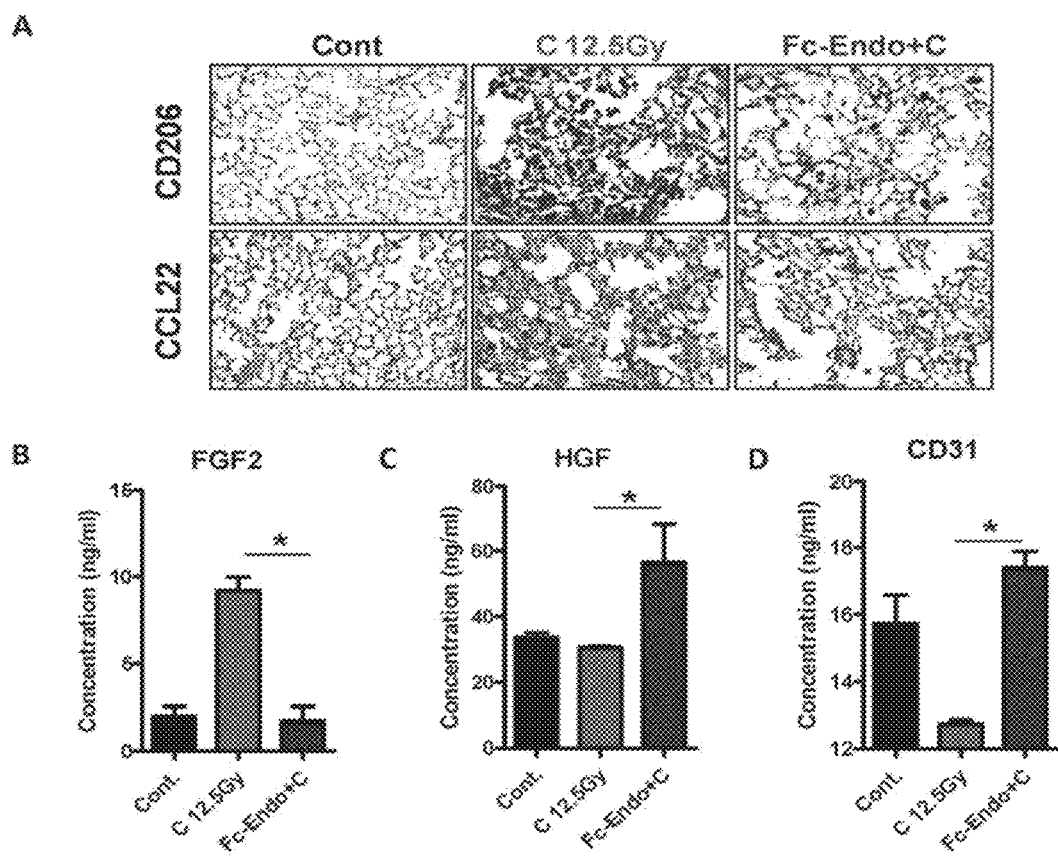

FIG. 7. Related evidence for inhibition of fibrosis by Fc-Endo treatment after carbon-ion irradiation. (A) Fc-Endo was also found to attenuate pro-fibrosis M2 macrophage infiltration. (B) The expression of pro-fibrosis FGF2 was decreased by Fc-Endo. (C) The expression of anti-fibrosis HGF was increased by Fc-Endo. (D) The loss of endothelial marker CD31 was reversed by Fc-Endo. (*P<0.05, P<0.01, *P<0.001).

Figure 8:
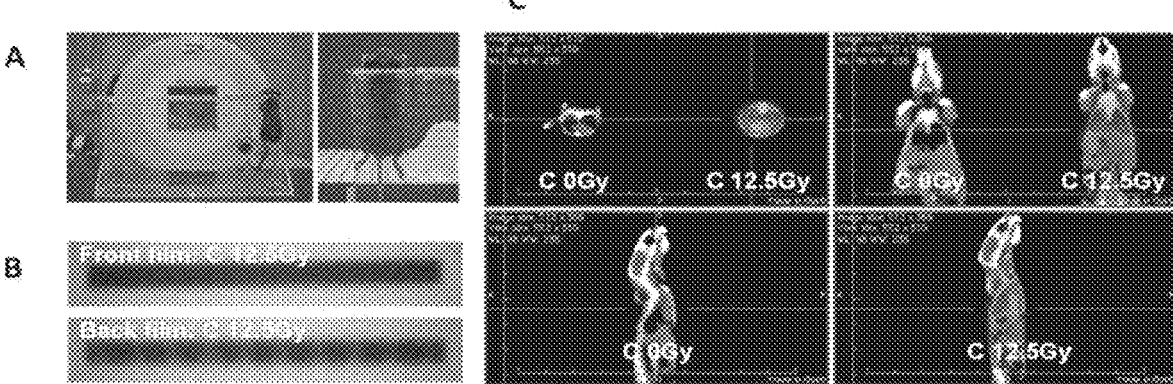

FIG. 8. A demonstration of precise mice thorax irradiation by carbon ions irradiation (Carbon ions 12.5Gy at the SOBP). (A) Mouse was fixed in a specially designed holder for thoracic irradiation. (B) The particle dosing in lung was homogenous as verified by the entrance and exit films (Kodak EDR2). (C) PET/CT beam verification immediately after irradiation confirmed a precise dose deposition in the lung area. The breath motion has been also taken into account.

Figure 9:
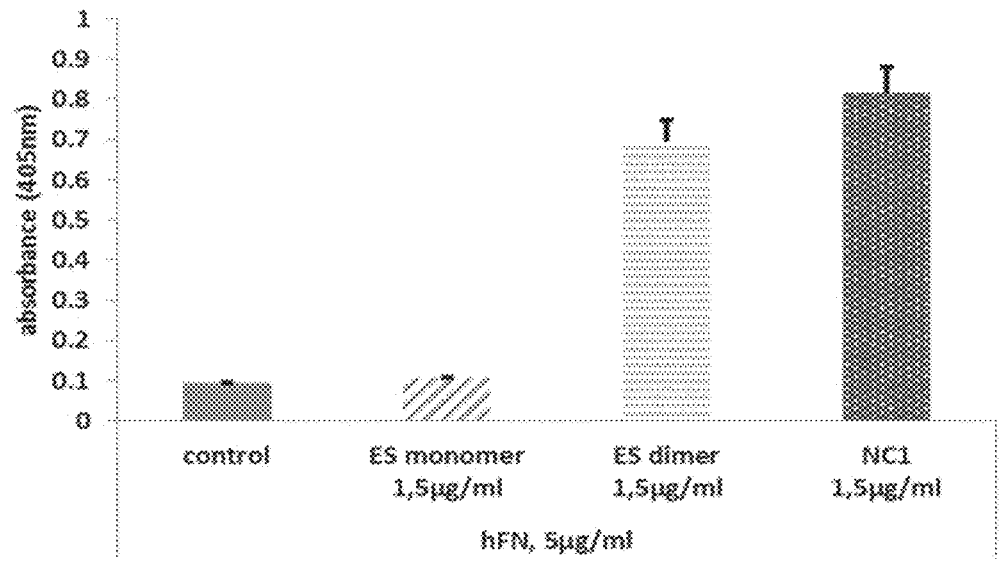

FIG. 9. Fibronectin binding of oligomeric endostatin. Exclusive binding of NCI and endostatin (ES) dimer but not monomer to fibronectin (FN). Elisa plate was coated with human fibronectin. After blocking with BSA, endostatin monomer, dimer and NCI were used as ligands at concentrations indicated. For detection of endostatin bound to fibronectin, anti-endostatin antibodies were employed.

Figure 10:
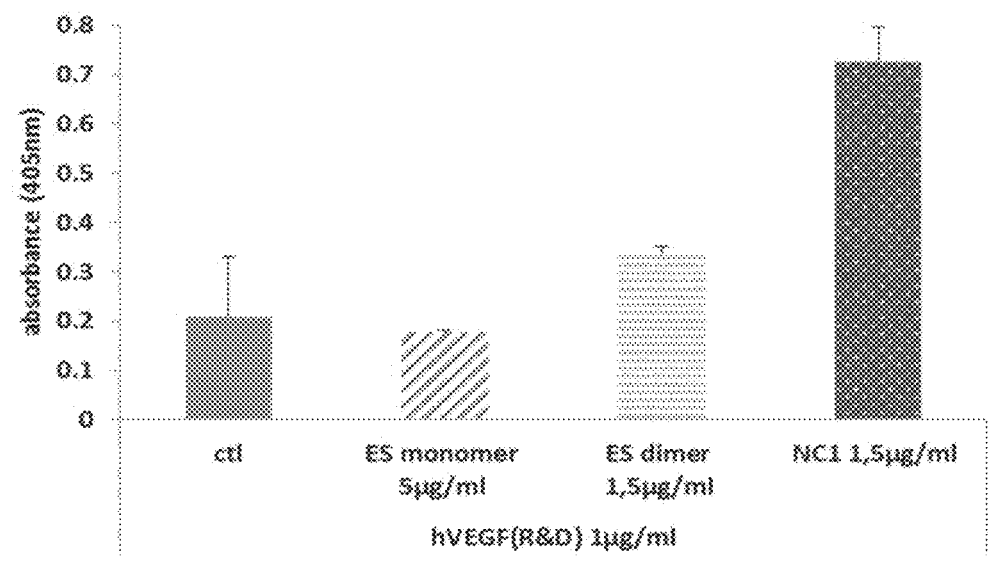

FIG. 10. VEGF binding of oligomeric endostatin. Exclusive binding of NCI and endostatin (ES) dimer but not endostatin monomer to the vascular endothelial growth factor (VEGF). Elisa plate was coated with human VEGF. After blocking with BSA, endostatin monomer, dimer and NCI were used as ligands at concentrations indicated. For detection of endostatin bound to VEGF, anti-endostatin antibodies were employed.

Figure 11:
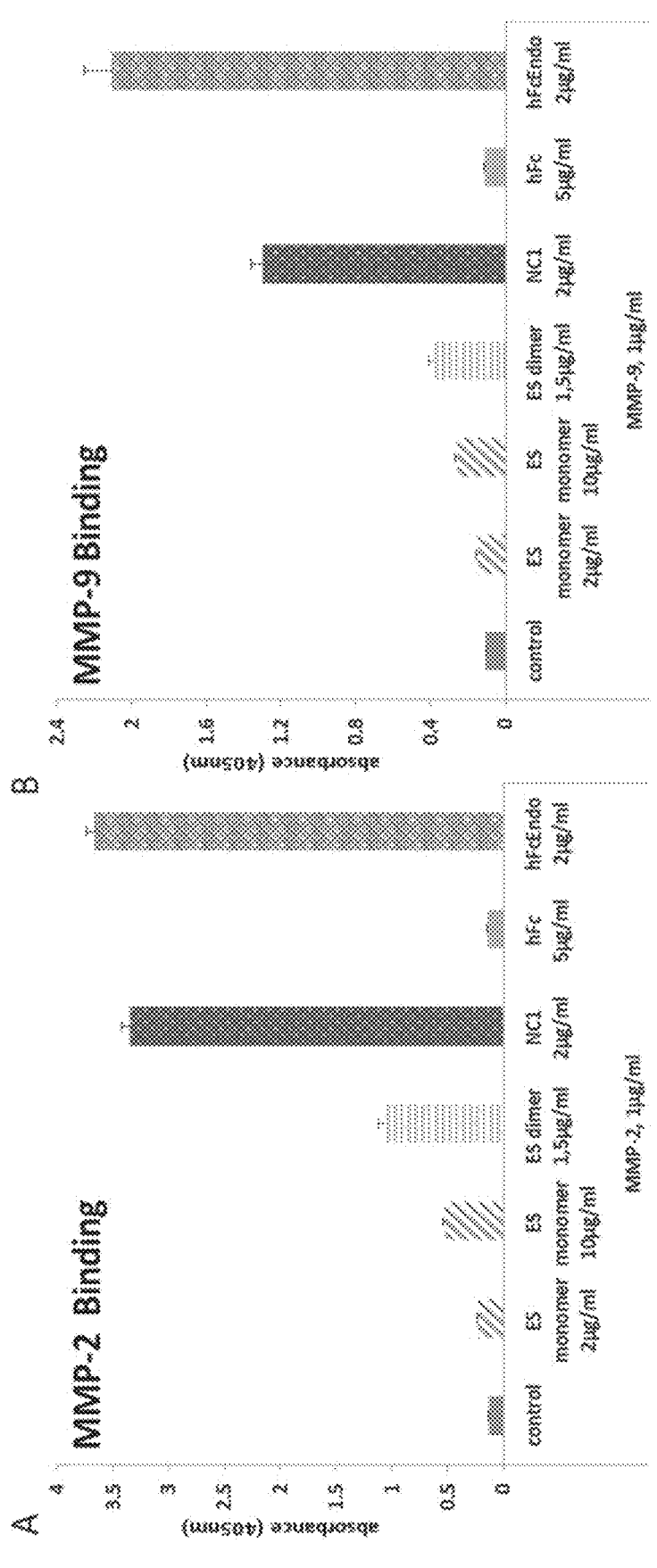

FIG. 11. MMP-2/9 binding of oligomeric endostatin. Binding of NCI, endostatin (ES) dimer and Fc-Endostatin (dimerization over Fc moiety) to MMP-2 (A) and MMP-9 (B), respectively. In contrast, endostatin monomer shows a weak binding to the MMPs. Elisa plate was coated with human MMP-2 or MMP-9, respectively. After blocking with BSA, endostatin (ES) monomer, endostatin (ES) dimer, Fc-endostatin (Fc-ES), Fc-control (Fc) and NCI were used as ligands at concentrations indicated. For detection of endostatin bound to MMPs, anti-endostatin antibodies were employed.

FIG. 12. Loss of dimeric endostatin binding to MMP-2 and fibronectin after enterokinase digestion of Fc-endostatin (humanFcE) into endostatin monomer and Fc-dimer. (A) SDS-polyacrylamide electrophoresis of hFcE digestion by enterokinase. Lane 1 (Protein Markers). Lane 2: hFcE. Lane 3; upper band is Fc-dimer and lower band is endostatin monomer following digestion with enterokinase. Samples in 2 and 3 are under non-reduced conditions. Lane 5: hFcE. Lane 6: upper band Fc and lower band endostatin monomer following digestion. Lanes 5&6 were performed in reduced conditions. (B) Elisa assay as described above detects binding of dimeric endostatin (FcE) to fibronectin and MMP-2, respectively. Note, enterokinase digestion leading to monomeric endostatin and dimeric Fc resulting in significantly reduced binding to both candidate target molecules.

FIG. 13. Schematic illustration of protein oligomers for use in the invention. (A) Protein oligomer comprising N-terminal homodimeric Fc fusion constructs. Wildtype human IgG1 Fc is fused to the N-terminus of NC-1 or endostatin via a protease-cleavable linker. (B) Protein oligomer comprising C-terminal homodimeric Fc fusion constructs. Wildtype human IgG1 Fc is fused to the C-terminus of NC-1 or endostatin via a protease-cleavable linker.

FIG. 14. "Knobs-into-holes" (KiH)-engineered NC-1-Fc or endostatin-Fc fusion constructs (A) Heterodimer comprising a human IgG1 Fc with "knob" mutations fused to the N-terminus of the NC-1 or endostatin via a protease-cleavable linker, and a human IgG1 Fc with "hole" mutations. (B) Heterodimer comprising a human IgG1 Fc with "knob" mutations fused to the C-terminus of the NC-1 or endostatin via a protease-cleavable linker, and a human IgG1 Fc with "hole" mutations.

The invention will now be illustrated by examples which shall, however, not be construed as limiting the scope of the invention.

EXAMPLES

Example 1: Endostatin

Fc-endostatin (Fc-Endo) is a fusion protein of endostatin to the Fc region of a human IgG. It shows significantly improved pharmacokinetics and biologic efficacy relative to endostatin [Lee, T. Y., et al., *Linking antibody Fc domain to endostatin significantly improves endostatin half-life and efficacy*. Clin Cancer Res, 2008. 14 (5): p. 1487-93]. Moreover, fusion of two endostatin monomeric molecules to IgG Fc domain in Fc-endostatin leads to a synthetic dimerization of the molecule (FIG. 1B). Interestingly, oligomerization of endostatin was previously shown to confer additional properties to the molecule [Sudhakar, A., et al., *Human tumstatin and human endostatin exhibit distinct antiangiogenic activities mediated by alpha v beta* 3 *and alpha* 5 *beta* 1 *integrins*. Proc Natl Acad Sci USA, 2003. 100 (8): p. 4766-71]. Of note, the natural non-collagenous region of collagen 18 (NC-1) consists of three endostatin monomers connected over a protease sensitive hinge- and trimerization regions, respectively (FIG. 1A). Hence, the monomeric endostatin could be considered the final proteolytic fragment of the original trimeric molecule. Indeed, larger fragments than the monomeric endostatin were physiologically found in different tissues and serum (FIG. 1C). In the same context, the present inventors have shown that oligomerization is a prerequisite for binding of Fc-endostatin and NC-1 to fibronectin (FN), whereas the endostatin monomer does not bind FN (WO 2013/026913). FN is recognized as a key player in the pathogenesis of fibrosis, leading to a wide spectrum of downstream and associated pro-fibrotic signaling cascades. For examples, FN is reported to bind integrin alpha 5 (ITGA5B) and $\alpha v \beta_3$ [Torres, P. H., G. L. Sousa, and P. G. Pascutti, *Structural analysis of the N-terminal fragment of the antiangiogenic protein endostatin: a molecular dynamics study*. Proteins, 2011. 79 (9): p. 2684-92], which are associated with fibrosis promotion. Hence, oligomerization of endostatin e.g. via Fc-endostatin may have implications for its pleiotropic functions.

Yamaguchi et al. reported that endostatin via its C-terminal domain (E4 peptide) has elicited anti-fibrosis effects [Yamaguchi, Y., et al., *A peptide derived from endostatin ameliorates organ fibrosis*. Sci Transl Med, 2012. 4 (136): p. 136ra71]. However, the zinc binding domain has been previously confined to the N terminus (endostatin mP1 peptide) and was critical to numerous functions of the molecule [Tjin, R. M., et al., *A 27-amino-acid synthetic peptide corresponding to the NH2-terminal zinc-binding domain of endostatin is responsible for its antitumor activity*. Cancer Research, 2005. 65 (9): p. 3656-3663]. In the following examples, the present inventors aim to better understand the impact of oligomerization (Fc-endostatin) as well as N-vs. C-terminal fragments of endostatin (N-terminal endostatin peptide mP1, SEQ ID NO: 20; C-terminal endostatin peptide E4 or CE4, SEQ ID NO: 21) on modulating radiation-induced lung fibrosis.

Example 2: Endostatin Administration

Mice were treated with mFc-endostatin (murine endostatin as depicted in SEQ ID NO: 18 fused to the Fc fragment of the murine immunoglobulin γ-2a chain, as described in Bergers et al., Science 284 (5415), p. 808-812, 1999) from 3 days prior to irradiation till the end of the trials, at a dose of 100 µg/mouse every 5 days delivered subcutaneously. In parallel, endostatin peptides groups were administrated either mP1 endostatin (N-terminus; SEQ ID NO: 20) or E4 (or CE4) peptide (C-terminus; SEQ ID NO: 21; see Yamaguchi, Y., et al., *A peptide derived from endostatin ameliorates organ fibrosis*. Sci Transl Med, 2012. 4 (136): p. 136ra71), at a dose of 100 µg/mouse/b.i., subcutaneously, in addition to irradiations. Control groups were treated with PBS, mFc-endostatin, mP1 endostatin or E4 peptide alone and received no irradiation.

Example 3: Photon Irradiation and High-LET Carbon Irradiation

Total thoracic irradiation was performed as described previously with modifications (Abdollahi, J. Exp. Med. 2005, http://www.ncbi.nlm.nih.gov/pubmed/15781583).

Whole thoracic irradiation was administrated to 8-week-old C57BL/6 mice (Taconis, Bomholtvej, Denmark). Mice were maintained under specific pathogen-free conditions, and experiments were performed in compliance with institutional guidelines as approved by the Animal Care and Use Committee of the German Cancer Research Center (DKFZ). Prior to thoracic irradiation, mice were anesthetized by an intraperitoneal application of 0.36 ml/kg Rompun 2% (Bayer HealthCare) and 0.54 ml/kg ketamine 10% (Pfizer).

Particle irradiations were performed at the Heidelberg Ion-Beam Therapy Center (HIT), Heidelberg, Germany. The irradiation setup is shown below (FIG. 8). Carbon ions (12C) were applied at the spread-out Bragg peak (SOBP, 252.400-270.550 MeV/u) with linear energy transfer (LET) =70-157 keV/µm (mean at 86 keV/µm).

Photon irradiation was done with an Artiste linear accelerator (Siemens, Germany) with 6 MV and at a dose rate of 3 Gy/min at DKFZ, Heidelberg, Germany.

All irradiation plans were adjusted by anatomical and radiological estimation, ensuring full coverage of the lung area and sparing neighboring tissue at the maximum. PET/CT (Biograph mCT, Siemens) imaging was applied also for beam verification immediately after carbon-ion irradiation.

Example 4: Fibrosis Index (FI) Calculation

A clinical PET/CT scanner (Biograph mCT, Siemens) was applied for quantitative CT imaging pre-irradiation (pre-IR) and every 4 weeks post-irradiation (post-IR). CT imaging was performed under isoflurace anesthesia (2% isoflurane, 2 l/min oxygen). The standard protocol for the CT portion was as follows: 80 kV with 80 mA, a pitch of 0.6 mm, slice thickness of 0.6 mm and acquisition time of 32 s. Images were reconstructed using the filter kernel H50s (Siemens) into a transaxial field of view of 138×138 mm2 as a 512×512 matrix, where three animals were included in one scan. X-ray exposure was approximately 4 mGy per scan in the total field of view, roughly less than 1 mGy per animal.

Images acquired from the clinical CT scanner were viewed and analyzed in OsiriX Imaging Software (OsiriX v.3.9.4 64-bit version, Pixmeo SARL, Switzerland) and MITK software (Medical and Biological Informatics, German Cancer Research Center). Because of the relatively low resolution of the images, the HU intensities of microvasculature were averaged with the surrounding air-contained tissues. The lung, together with all the microstructures, was thereby segmented using a three-dimensional (3D) regional growing algorithm with a lower threshold of −900 HU and an upper threshold of −100 HU. A lower threshold of −600 HU was used on animals with emphysema (−450 HU). Trachea and primary bronchi were manually resected upon segmentation. After mean HU value and volume size were calculated within the segmented area, a histogram of the same lung region binned in an interval of 10 HU was extracted in order to achieve a more reliable evaluation that was insensitive to the selection of threshold values. Micro-CT imaging was performed using both the micro-CT component of a prototype SPECT-CT-OT system and Inveon SPECT/PET/CT (Siemens, Germany) at the corresponding time points (pre-IR and every 4 weeks post-IR) for further validation of clinical CT results. For prototype SPECT-CT-OT system, CT acquisitions were performed at 40 kV tube voltage, 0.4 mA anode current, 1 second acquisition time per projection, 240 projections per 360-degree rotation. Images were reconstructed into a matrix of 512×512×1024 with an isotropic voxel size of 0.065 mm. For Inveon SPECT/PET/ CT, CT acquisition were applied as 80 kV tube voltage, 0.5 mA anode current, 1 second acquisition time per projection, 720 projections per 360-degree rotation, with an effective pixel size of 19.29 µm. The micro-CT data were viewed and analyzed with MITK software. Segmentation of the lung area was performed manually for 10 successive transaxial CT slices. HU values for each voxel in the selected volumes of interest were exported to calculate the mean HU value, and, afterwards, used to generate a histogram.

Lung density, represented by the mean HU value of the entire lung area in CT, was calculated from segmented lungs. Fibrosis index (FI) was proposed based on CT measurement of mean lung density (MLD) in Hounsfield unit (HU) and lung volume as:

$$\text{Fibrosis index } (FI) = \sqrt{\overline{\Delta HU}\uparrow \times \overline{\Delta V}\downarrow}$$

where $\overline{\Delta HU}$ is an average of increased HU value from segmented lungs; $\overline{\Delta V}$ is the decreased lung volume with reference to age-matched control.

Example 5: Attenuation of Photon Irradiation-Induced Lung Fibrosis by Endostatin Fc-Endostatin and mP1 Endostatin Inhibited Lung Fibrosis and Prolonged Survival Mice were treated with Fc-endostatin (Fc-Endo), N-terminus endostatin peptide (mP1) or C-terminus endostatin E4 peptide (CE4) (see FIG. 2) combined with photon 20 Gy whole thoracic irradiation (see Example 3). Micro-CT imaging revealed diffuse ground glass opacities and architectural distortion in 20 Gy-irradiated tissue, indicating a massive interstitial fibrosis generation. Severe fibrotic lung parenchyma was seen also in the CE4 combined irradiation group. In contrast, remarkably reduced fibrosis were observed in Fc-Endo and mP1 treatment groups (FIG. 3).

Quantitative clinical CT follow-up was completed at the end point of 24 weeks after irradiation (FIG. 3B). Compared to the ionizing radiation (IR)-only condition, significantly reduced mean lung density (MLD) was found in the Fc-Endo+X and mP1+X treatment groups (P<0.001, P<0.05, respectively). In line with this, total lung volume (LV) was preserved in those groups, whereas significant loss of LV occurred in IR-only mice (P<0.001, P<0.05, respectively, for Fc-Endo+X and mP1+X relative to IR-only). No significant difference was observed in the CE4+X treated group in terms of MLD or decreased LV compared to IR-only mice (P>0.05). No statistical difference was found in Fc-Endo, mP1 or CE4 treated groups, in comparison to control groups in the same parameters (MLD and LV, data not shown).

Based on the inventors' radiation induced lung fibrosis (RILF), the fibrosis index (FI) was considered the most reliable and robust indicator for quantitative assessment of lung fibrosis (see Example 4). Remarkably attenuated FI levels were observed in the Fc-Endo+X (around 3.03, 43% decrease) and mP1+X (around 1.86, 26% decrease) treatment groups (P<0.001, P<0.05, respectively). However, there was no statistically significant difference between the CE4+X-administered and IR-only groups (P=0.43) (FIG. 3C).

The reduced radiation induced FI values correlated with a survival benefit in the Fc-Endo and mP1 treatment groups; e.g., the survival rate at the end of the observation period (25 weeks post IR) was 80% for Fc-Endo+X and 60% for mP1+X arm, respectively, versus only 10% in IR-only mice (P<0.01 and P<0.05, respectively). The inventors did not observe a statistically significant difference between CE4+X and IR-only groups (FIG. 3D).

Example 6: Fc-Endostatin and mP1 Endostatin Improved Pulmonary Function

As an accompanying symptom of lung fibrosis, the deterioration in pulmonary function was studied in all groups (FIG. 4A, B). The IR-only group had significantly higher $pCO_2$ and lower pH compared to the control group (P<0.05, P<0.001, respectively), indicating a chronic respiratory acidosis because of serious impairment in ventilation. In contrast, these measurements did not differ significantly between Fc-Endo- or mP1+X treated groups and the control group (P>0.05, P>0.05, respectively), revealing a favorable respiratory function in those groups.

In comparison to the IR-only group (X 20 Gy), the most well-protected lung function in terms of $pCO_2$ and pH was achieved with Fc-Endo+X treatment (P<0.05, P<0.001, respectively). The next best outcome was provided by mP1+X, for which $pCO_2$ and pH were also significantly different from IR-only (X20Gy) conditions (P<0.05, P<0.05, respectively).

No significant benefits ($pCO_2$ and pH) were found in mice treated with CE4+X compared to IR-only mice (P>0.05, P>0.05, respectively). Weight loss at the end point was evaluated (FIG. 4C). All endostatin treatment groups were observed with less weight loss compared to IR-only mice (all P<0.05). In particular, Fc-Endo+X-treated mice had an advantage over mP1-Endo-X and CE4-Endo+X-treated mice in terms of weight (both P<0.05 relative to Fc-Endo).

Histopathological analysis suggested clear improvements in inflammatory cell infiltration, septal thickness and alveolar architecture in mice that received Fc-Endo+X or mP1-Endo+X, compared to IR-only mice. The Fc-Endo+X and mP1-Endo+X treatment groups also showed markedly less collagen deposition and scarring in trichrome stainings (FIG. 4D). There was no difference in non-irradiated lung treated with Fc-Endo, mP1-Endo or CE4-Endo (FIG. 4E).

Example 7: Effects of Fc-Endostatin on M2 Polarization, Gene- and Protein Regulation Aberrant ECM remodeling is a characteristic feature of pulmonary fibrosis. The inventors found that a variety of key ECM proteins including tenascin C, collagen I and III, elastin, fibrillin, α-actin and MMPs were suppressed or 'switched off' by Fc-Endo+X at the transcriptional level (FIG. 5A). In concert with this, immunohistochemistry results suggested a reduction of M2 macrophage influx in Fc-Endostatin+X vs. 20Gy irradiated lung (FIG. 5B).

Radiation induced pulmonary fibrosis (X20Gy) was associated with reduced CD31 and enhanced basic fibroblast growth factor (bFGF or FGF2) protein levels. Addition of Fc-Endo to radiotherapy reversed this phenotype to the levels detected in the sham treated control (FIG. 5). Intriguingly, hepatocyte growth factor (HGF), which has been recently associated with anti-fibrotic properties [Crestani, B., et al., *Hepatocyte growth factor and lung fibrosis*. Proc Am Thorac Soc, 2012. 9 (3): p. 158-63; Phin, S., et al., *Imbalance in the pro-hepatocyte growth factor activation system in bleomycin-induced lung fibrosis in mice*. Am J Respir Cell Mol Biol, 2010. 42 (3): p. 286-93] was expressed at a much higher level after Fc-Endo+X, compared to IR-alone (X-20Gy) (P<0.05) (FIG. 5D)).

Example 8: Inhibition of Carbon-Ion-Induced Pulmonary Fibrosis by Fc-Endostatin Fc-Endostatin Inhibited Lung Fibrosis Induced by Carbon Ions Given that Fc-endostatin was more effective than other endostatin peptide fragments at inhibiting photon-induced lung fibrosis, the inventors next studied the efficacy of Fc-endostatin to modulate fibrosis induced by high-LET carbon irradiation.

Micro-CT imaging showed diffuse fibrotic lungs, after carbon-ion 12.5 Gy irradiation (C12.5). In contrast, remarkably reduced fibrosis was seen in the Fc-Endo+C12.5 treatment group (FIG. 6A).

Quantitative clinical CT follow-up at the endpoint of 24 weeks was performed (FIG. 6B). Lung density (MLD) in the Fc-Endo+C12.5 group was significantly lower than that in the carbon alone (C12.5) group (P<0.01). In line with this, total LV was also preserved in Fc-Endo+C12.5-treated mice, whereas there was significant loss in total LV for carbon alone (C12.5) mice (P<0.01).

FI was considered the most important indicator in lung fibrosis assessment (see Example 4). The FI of the Fc-Endo+C12.5 group was notably lower than that of the carbon irradiated (C12.5) group (P<0.001) (FIG. 6C).

Histopathological analysis suggested clear improvements in inflammation, septal thickness and the alveolar architecture for mice receiving Fc-Endo+C12.5, compared to carbon irradited (C12.5) mice. Likewise, less collagen deposition and scarring was found in trichrome stainings for Fc-Endo+C12.5-treated mice (FIG. 6D).

Example 9: Immunological and Molecular Confirmation of Fibrosis Inhibition after High LET Irradiation by Fc-Endostatin Mice receiving Fc-endostatin treatment had a clear reduction of pro-fibrotic M2 macrophages (CD206 and CLL22 positive), in carbon irradiated lungs (FIG. 7A). In line with endostatin effects on photon irradiated lungs, a reversal of FGF2 induction and loss of CD31 protein levels was found after Fc-Endo+C12.5 vs. carbon radiation alone (FIG. 7B). Moreover, Fc-endostatin treatment resulted in elevated anti-fibrotic HGF protein levels in carbon irradiated lungs (P<0.05) (FIG. 7C).

Together, these data confirm the relevance of M2 polarization, reduced intact lung architecture consisting of blood gas barrier (CD31 positive microvessels) and growth factor/cytokine profile (FGF) in development of fibrosis independent of radiation quality. Fc-endostatin efficiently reversed this phenotype in both carbon- and photon-irradiation models.

Example 10: Possible Mechanisms of Fc-Endostatin in Inhibiting Fibrosis

The inventors found that Fc-endostatin (Fc-Endo) and N-terminus endostatin (mP1 endostatin) peptide were effective inhibitors of lung fibrosis induced by photon or carbon-ion irradiation. Fc-endostatin was superior to mP1 in terms of survivals, radiological, physiological, histological examinations, M2 macrophage polarization and Th2-biased immunity, ECM composition, cellularity alternations, etc. This could be the consequence of improved pharmacokinetics of Fc-endostatin with longer half-life (exposure) as reported for the anti-cancer activity of this compound [Lee, T. Y., et al., *Linking Antibody Fc Domain to Endostatin Significantly Improves Endostatin Half-life and Efficacy*. Clinical Cancer Research, 2008. 14 (5): p. 1487-1493]. Alternatively, different mechanism of action might govern the anti-fibrotic effect of Fc-endostatin. Considering that endostatin is a proteolytic fragment of collagen 18 non-collagenous domain 1 (NC-1) which is physiologically a trimer, dimerization of endostatin via Fc-conjugation might represent a more physiologic correlate of this endogenous protein. Interestingly, endostatin plasma levels were found to be enhanced in patients with pulmonary fibrosis. The inventors have previously shown that Fc-endostatin as a synthetic dimer can bind to fibronectin (FN), whereas endostatin monomer does not (see WO 2013026913). FN is thought to have a central role in initiation and perturbation of fibrosis development [To, W. S. and K. S. Midwood, *Plasma and cellular fibronectin: distinct and independent functions during tissue repair*. Fibrogenesis Tissue Repair, 2011. 4: p. 21]. Therefore, it is tempting to speculate that Fc-endostatin binding to FN, leads to a wide spectrum of downstream anti-fibrotic signal cascades.

Matrix formation requires FN, integrins and molecule adhesion to the cytoskeleton [Schwarzbauer, J. E. and D. W. DeSimone, *Fibronectins, their fibrillogenesis, and in vivo functions*. Cold Spring Harb Perspect Biol, 2011. 3 (7)]. Integrin-mediated connective tissue production is the essential pathway in fibrogenesis. Most integrins bind to FN through the RGD loop in $FNIII_{10}$ and the neighboring PHSRN (SEQ ID NO: 31) sequence in $FNIII_9$. It is well accepted that the binding of pro-fibrotic integrins (e.g., $\alpha_5\beta_1$, $\alpha_v B_1$, $\alpha_v \beta_3$) to FN is a key step in the progression of FN-matrix assembly [Takahashi, S., et al., *The RGD motif in fibronectin is essential for development but dispensable for fibril assembly*. J Cell Biol, 2007. 178 (1): p. 167-78; Leiss, M., et al., *The role of integrin binding sites in fibronectin matrix assembly in vivo*. Curr Opin Cell Biol, 2008. 20 (5): p. 502-7].

The present inventors found a strong activation of αIIb integrin by Fc-endostatin. In particular, Kindlin-3, the key molecule to activating integrin αIIb was also found to be highly up-regulated transcriptionally (data not shown). Integrin αIIb binds to FN at the $FNIII_{9-10}$, which are the same sites for those pro-fibrotic integrins [Leiss, M., et al., *The role of integrin binding sites in fibronectin matrix assembly in vivo*. Curr Opin Cell Biol, 2008. 20 (5): p. 502-7., Chada, D., T. Mather, and M. U. Nollert, The synergy site of fibronectin is required for strong interaction with the platelet integrin alphaIIbbeta3. Ann Biomed Eng, 2006. 34 (10): p. 1542-52]. Hence, in addition to FN binding, endostatin induced integrin αIIb upregulation may competitively inhibit binding of fibronectin to common pro-fibrotic integrins. Further affinity assays are ongoing to understand potential mechanisms behind endostatin-integrin-FN interactions. The inventors also found enhanced expression of HGF after Fc-endostatin and mP1. HGF has been recently identified to elicit putative anti-fibrotic effects [Crestani, B., et al., *Hepatocyte growth factor and lung fibrosis*. Proc Am Thorac Soc, 2012. 9 (3): p. 158-63; Phin, S., et al., *Imbalance in the pro-hepatocyte growth factor activation system in bleomycin-induced lung fibrosis in mice*. Am J Respir Cell Mol Biol, 2010. 42 (3): p. 286-93].

The most striking data the inventors could provide so far is that the N-terminal zinc binding region of endostatin known to be chiefly involved in its anti-angiogenic effects [Tjin, R. M., et al., *A 27-amino-acid synthetic peptide corresponding to the NH2-terminal zinc-binding domain of endostatin is responsible for its antitumor activity*. Cancer Research, 2005. 65 (9): p. 3656-3663] is also relevant for the anti-fibrotic effect elicited by this endogenous protein. This is in clear contrast to recently published data postulating an anti-fibrotic effect of the C-terminal domain of endostatin [Yamaguchi, Y., et al., *A peptide derived from endostatin ameliorates organ fibrosis*. Sci Transl Med, 2012. 4 (136): p. 136ra71]. In the radiation induced lung fibrosis model used by the present inventors, the C-terminal peptide was not effective to improve most investigated parameter of fibrosis development. Together, the data of the present inventors indicate an important role for the N-terminus sequence as well as dimerization of endostatin underlying its anti-fibrotic effect in the RILF model.

Example 11: Binding Properties of Oligomeric Endostatin

The present inventors have previously shown that the anti-fibrotic effect of endostatin could most conceivably not be confined to its C-terminal fragment as proposed by Yamaguchi et al., 2012, loc. cit. A closer look at the endostatin C-terminus, the E4 peptide containing area, shows no obvious structural feature linking this fragment with potential protein interaction partners that could provide a mechanistic explanation for the postulated anti-fibrotic effect of the molecule. Another explanation for the lack of E4 activity might be that in contrast to their acute murine fibrosis models, the present inventors utilized a radiation induced lung fibrosis model, where fibrosis development follows a slow (over 24 weeks after irradiation) and chronic kinetic more closely resembling the pathophysiology in humans.

The present inventors further showed that the N-terminal zinc binding fragment elicit moderate anti-fibrotic activity. However, the most efficient attenuation of lung fibrosis was found when a synthetic endostatin dimer (Fc-endostatin) was utilized. Fc-endostatin (FcE) consists of two Fc chains (connected by disulfide bonds), extended to two molecules of endostatin each linked to a single Fc chain. Therefore, the two adjacent endostatin molecules become a dimer as a result of the Fc dimer.

The present inventors previously have shown that the physiologic molecule circulating in the human blood is endostatin precursor NCI fragment of collagen 18 which is an oligomeric endostatin molecule with three endostatin domains (endostatin trimer). Moreover, the present inventors showed that mixing Fc-endostatin with platelets lysate, fibronectin (FN) was immune-precipitated without need for additional antibody to facilitate their interactions. The data of the present inventors later made it clear that binding of FN is unique to oligomeric endostatin (dimer or trimeric NC1) and is not shared by endostatin monomer which is considered so far as the key anti-angiogenic molecule derived from collagen 18 (FIG. 9). Of note, fibronectin is a central molecule in development of tissue fibrosis. Hence hypothesis by the present inventors is that the beneficial anti-fibrotic effect of the oligomeric endostatin is at least in part mediated by its property to bind FN, and this distinguishes the NC1 or endostatin oligomers from monomers or fragments thereof (N-terminal, middle or C-terminal fragments).

In the present inventors' view, endostatin is an end-degradation product of NC1. They present here new data further demonstrating that the binding properties of endostatin dimer and NC1 trimer are quite distinct from endostatin monomer in terms of relevant protein interaction partners. In other words, oligomerization properties of endostatin play an important role in its binding to key players of tissue remodeling with high impact for exploration of its anti-fibrotic and anti-cancer effects.

A novel finding of the present inventors is the binding of oligomeric endostatin to the vascular endothelial growth factor (VEGF), a pivotal molecule in a number of so called VEGF-related diseases encompassing a broad range of pathophysiologic conditions from wet-macular degeneration to cancer and fibrosis. Indeed, Nindetanib which was recently approved for treatment of pulmonary fibrosis is a potent inhibitor of PDGF and VEGF signaling. In contrast to endostatin dimer and NC1, VEGF does not bind to endostatin monomer (FIG. 10).

Crystallography of endostatin had previously demonstrated that this protein was a dimer each binding an atom of zinc (Ding, Y. H., K. Javaherian, K. M. Lo, et al. 1998. Zinc-dependent dimers observed in crystals of human endostatin. Proc. Natl. Acad. Sci. U.S.A. 95, 10443-10448). Interestingly, the N-terminal zinc binding domain of endostatin resembles that of MMPs (matrix metalloproteinases); important players in remodeling of extracellular matrix, in development of fibrosis, cancer progression and metastasis. Here, the present inventors demonstrate that indeed endostatin dimer and NCI trimer bind to MMP-2 and MMP-9; a property not shared by endostatin monomer (FIG. 11). This finding opens a new avenue for pursuing biological properties of oligomeric endostatin, either by synthetic design, e.g., dimerization via Fc or other alternatives to generate and improve a drug mimicking the endostatin precursor molecule NC1.

Based on the studies of the present inventors of crystal structure of endostatin dimer, they recognized that amino acids glutamine at position 7 from N-terminus is closely adjacent to the same amino acid in the second chain. They replaced Q (Gln) by C (Cys) in this position predicting that an artificial endostatin dimer would result, covalently attached by a disulfide bond. Their prediction turned out to be correct. The new artificial dimer was expressed in Fc-endostatin vector as before. However, both Fc and endostatin were separately dimerized by their corresponding disulfide bonds. Enterokinase digestion of this recombinant protein resulted in an Fc dimer and an endostatin dimer which were purified on an S-200 Sephadex. The term "endostatin dimer" (ES dimer) employed in all binding assays presented in this Example 11 refers to this purified molecule.

Another convincing evidence in support of their hypothesis that binding properties presented here are observed with oligomeric endostatin only, is shown in FIG. 12. An enterokinase binding site is engineered between Fc and endostatin in Fc-endostatin. Digestion of this molecule with enterokinase (EK) resulted in Fc dimer and two endostatin monomers. Without any additional modifications, mixture of Fc and endostatin displayed distinct properties from intact Fc-endostatin.

Together, the present inventors show here additional data unraveling novel bindings partners for oligomeric but not monomeric endostatin with pivotal roles in development of organ fibrosis. The unique property of oligomeric endostatin to target these molecules provides a plausible explanation for the superior anti-fibrotic activity of NC1 or NC1-like oligomeric endostatins (e.g. Fc-ES) over the monomeric end degradation product or even peptide fragments thereof (mP1 or E4) tested by the present inventors in the murine lung fibrosis model. The novel findings by the present inventors opens a new avenue for pursuing the development of NC1 or NC1-mimetics consisting of oligomeric endostatin (at least a dimer) for the treatment of not only fibrosis-related diseases, but also VEGF-related diseases, MMP-dependent diseases, and the modulation of fibronectin function.

The reagents which have been used in Example 11 are listed, in the following:

Corning, 96 well EIA/RIA High Bind, polystyrene, flat bottom, clear, non-sterile #3590

BSA (Sigma Aldrich #A7030 IgG free)

recombinant hMMP-2 (R&D #902-MP-010)>1 µg/ml in PBS recombinant hMMP-9 (R&D #911-MP-010)>1 µg/ml in PBS R7012 a.p. (anti-endostatin antibody)

ABTS (Rockland #ABTS-100)

Peroxidase Conjugated Affini Pure Goat anti-rabbit IgG (H+L) (Jackson Immuno Research #111-035-003 2.0 ml)

hFN (R&D #1918FN-02M)

Recombinant Human VEGF165 (R&D Systems a biotechne brand #293-VE-010/CF)

Proteingel:

Page Ruler Plus Prestained Protein Ladder (Thermo Scientific #26619)

SDS page 4-20%:

Mini-Protean TGX Precast Protein Gels (BioRad #4561094)

Enterokinase, Light Chain, Porcine (GenScript #Z01003

---

The invention claimed is:

1. A method for treating or ameliorating a matrix metalloproteinase (MMP)-related disease, wherein said MMP-related disease comprises tissue remodeling in a benign or malignant disease where MMP activation contributes to the pathophysiology, in a patient in need thereof, the method comprising administering to the patient a therapeutically effective dose of a protein oligomer comprising (i) at least two NC-1 monomers of collagen 18 or (ii) at least two endostatin domains of collagen 18 or (iii) at least two N-terminal peptides of the collagen 18 endostatin domain, thereby, treating or ameliorating said matrix metalloproteinase (MMP)-related disease in the patient, wherein the NC-1 monomer of human collagen 18 comprises a heterologous oligomerization domain comprising an Fc domain from knobs-into-holes (KiH)-engineered human IgG, a hinge region and/or an endostatin domain or fragments of said endostatin domain and, optionally, a recombinant protease cleavage site within the hinge region.

2. The method of claim 1, wherein the Fc domain is from knobs-into-holes (KiH)-engineered human IgG1.

3. The method of claim 2, wherein the Fc domain comprises the amino acid sequence of SEQ ID Nos. 25, 26, 28 and/or 30.

4. The method of claim 1, wherein said heterologous oligomerization domain further comprises an artificial oligomerization domain.

5. The method of claim 1, wherein said protein oligomer further comprises a native oligomerization domain.

6. The method of claim 1, wherein the endostatin domain of collagen 18 is selected from an amino acid sequence of SEQ ID NO: 18 or SEQ ID NO: 19 or the N-terminal peptide of the collagen 18 endostatin domain is selected from an amino acid sequence from amino acid residue 1 to 132 of SEQ ID NO: 18 or SEQ ID NO: 19.

7. The method of claim 1, wherein said protein oligomer further comprises an RGD motif and/or PHSRN motif of Fibronectin of SEQ ID NO: 31, in the NC-1 monomer of collagen 18, the endostatin domain of collagen 18 or the N-terminal peptide of the collagen 18 endostatin domain.

8. The method of claim 1, wherein said protein oligomer binds to Fibronectin, VEGF, MMP-2 and/or MMP-9.

9. The method of claim 1, wherein said protein oligomer further comprises angiostatin, thrombospondin, anti-PD-1/PD-L1 antibodies or another therapy employed for the MMP-related disease.

10. The method of claim 1, wherein the protein oligomer is administered at a concentration of 0.1-1 mg/kg/day.

11. The method of claim 1, wherein the protein oligomer is administered intravenously, intracranial/intrathecal, intravitreal, subcutaneously or intraperitoneally.

12. The method of claim 1, wherein the protein oligomer has one or more biological activities selected from anti-fibrotic activity, anti-angiogenic activity, anti-invasive/anti-metastatic activity, reducing vascular permeability activity, anti-inflammatory, and/or anti-tumorigenic activity.

13. The method of claim 4, wherein the artificial oligomerization domain contains a single mutation at position 7 of the endostatin domain of collagen 18 in which glutamine is replaced by cysteine.

14. The method of claim 5, wherein the native oligomerization domain is a non-triple helical trimerization domain of collagen 18.

15. The method of claim 1, wherein said MMP activation comprises activation of MMPs during the process of local tumor invasion and cancer metastasis evident in tumors with high local therapy failure rates and acquired enhanced MMP activation as the function of therapy induced selection pressures.

16. The method of claim 15, wherein the tumors with high local therapy failure rates are selected from the group consisting of glioblastoma, pancreatic cancer, and lung cancer.

17. The method of claim 15, wherein the therapy induced selection pressures are selected from the group consisting of tumor hypoxia and fibrosis post radiotherapy.

\* \* \* \* \*

SEQUENCE LISTING

```
Sequence total quantity: 34
SEQ ID NO: 1              moltype = AA  length = 1527
FEATURE                  Location/Qualifiers
source                   1..1527
                         mol_type = protein
                         organism = Mus sp.
SEQUENCE: 1
MAPDPSRRLC LLLLLLLSCR LVPASADGNS LSPLNPLVWL WPPKTSDSLE GPVSKPQNSS   60
PVQSTENPTT HVVPQDGLTE QQTTPASSEL PPEEEEEEDQ KAGQGGSPAT PAVPIPLVAP  120
AASPDMKEEN VAGVGAKILN VAQGIRSFVQ LWDEDSTIGH SAGTEVPDSS IPTVLPSPAE  180
LSSAPQGSKT TLWLSSAIPS SPDAQTTEAG TLAVPTQLPP FQSNLQAPLG RPSAPPDFPE  240
NVAEEVGLLQ LLGDPLPEKI SQIDDPHVGP AYIFGPDSNS GQVAQYHFPK LFFRDFSLLF  300
HVRPATEAAG VLFAITDAAQ VVVSLGVKLS EVRDGQQNIS LLYTEPGASQ TQTGASFRLP  360
AFVGQWTHFA LSVDGGSVAL YVDCEEFQRV PFARASQGLK LERGAGLFVG QAGTADPDKF  420
QGMISELKVR KTPRVSPVHC LDEEDDDEDR ASGDFGSGFE ESSKSHKEDT SLLPGLPQPP  480
PVTSPPLAGG STTEDPRTEE TEEDAAVDSI GAETLPGTGS SGAWDEAIQN PGRGLIKGGM  540
KGQKGEPGAQ GPPGPAGPQG PAGPVVQSPN SQPVPGAQGP PGPQGPPGKD GTPGRDGEPG  600
DPGEDGRPGD TGPQGFPGTP GDVGPKGEKG DPGIGPRGPP GPPGPPGPSF RQDKLTFIDM  660
EGSGFSGDIE SLRGPRGFPG PPGPPGVPGL PGEPGRFGIN GSYAPGPAGL PGVPGKEGPP  720
GFPGPPGPPG PPGKEGPPGV AGQKGSVGDV GIPGPKGSKG DLGPIGMPGK SGLAGSPGPV  780
GPPGPPGPPG PPGPGFAAGF DDMEGSGIPL WTTARSSDGL QGPPGSPGLK GDPGVAGLPG  840
AKGEVGADGA QGIPGPPGRE GAAGSPGPKG EKGMPGEKGN PGKDGVGRPG LPGPPGPPGP  900
VIYVSSEDKA IVSTPGPEGK PGYAGFPGPA GPKGDLGSKG EQGLPGPKGE KGEPGTIFSP  960
DGRALGHPQK GAKGEPGFRG PPGPYGRPGH KGEIGFPGRP GRPGTNGLKG EKGEPGDASL 1020
GFSMRGLPGP PGPPGPPGPP GMPIYDSNAF VESGRPGLPG QQGVQGPSGP KGDKGEVGPP 1080
GPPGQFPIDL FHLEAEMKGD KGDRGDAGQK GERGEPGAPG GGFFSSSVPG PPGPPGYPGI 1140
PGPKGESIRG PPGPPGPQGP PGIGYEGRQG PPGPPGPPGP PSFPGPHRQT VSVPGPPGPP 1200
GPPGPPGAMG ASAGQVRIWA TYQTMLDKIR EVPEGWLIFV AEREELYVRV RNGFRKVLLE 1260
ARTALPRGTG NEVAALQPPL VQLHEGSPYT RREYSYSTAR PWRADDILAN PPRLPDRQPY 1320
PGVPHHHSSY VHLPPARPTL SLAHTHQDFQ PVLHLVALNT PLSGGMRGIR GADFQCFQQA 1380
RAVGLSGTFR AFLSSRLQDL YSIVRRADRG SVPIVNLKDE VLSPSWDSLF SGSQGQLQPG 1440
ARIFSFDGRD VLRHPAWPQK SVWHGSDPSG RRLMESYCET WRTETTGATG QASSLLSGRL 1500
LEQKAASCHN SYIVLCIENS FMTSFSK                                     1527

SEQ ID NO: 2              moltype = AA  length = 1516
FEATURE                  Location/Qualifiers
source                   1..1516
```

```
                          mol_type = protein
                          organism = Homo sapiens
SEQUENCE: 2
MAPYPCGCHI LLLLFCCLAA ARANLLNLNW LWFNNEDTSH AATTIPEPQG PLPVQPTADT    60
TTHVTPRNGS TEPATAPGSP EPPSELLEDG QDTPTSAESP DAPEENIAGV GAEILNVAKG   120
IRSFVQLWND TVPTESLARA ETLVLETPVG PLALAGPSST PQENGTTLWP SRGIPSSPGA   180
HTTEAGTLPA PTPSPPSLGR PWAPLTGPSV PPPSSERISE EVGLLQLLGD PPPQQVTQTD   240
DPDVGLAYVF GPDANSGQVA RYHFPSLFFR DFSLLFHIRP ATEGPGVLFA ITDSAQAMVL   300
LGVKLSGVQD GHQDISLLYT EPGAGQTHTA ASFRLPAFVG QWTHLALSVA GGFVALYVDC   360
EEFQRMPLAR SSRGLELEPG AGLFVAQAGG ADPDKFQGVI AELKVRRDPQ VSPMHCLDEE   420
GDDSDGASGD SGSGLGDARE LLREETGAAL KPRLPAPPPV TTPPLAGGSS TEDSRSEEVE   480
EQTTVASLGA QTLPGSDSVS TWDGSVRTPG GRVKEGGLKG QKGEPGVPGP PGRAGPPGSP   540
CLPGPPGLPC PVSPLGPAGP ALQTVPGPQG PPGPPGRDGT PGRDGEPGDP GEDGKPGDTG   600
PQGFPGTPGD VGPKGDKGDP GVGERGPPGP QGPPGPPGPS FRHDKLTFID MEGSGFGGDL   660
EALRGPRGFP GPPGPPGVPG LPGEPGRFGV NSSDVPGPAG LPGVPGREGP PGFPGLPGPP   720
GPPGREGPPG RTGQKGSLGE AGAPGHKGSK GAPGPAGARG ESGLAGAPGP AGPPGPPGPP   780
GPPGPGLPAG FDDMEGSGGP FWSTARSADG PQGPPGLPGL KGDPGVPGLP GAKGEVGADG   840
VPGFPGLPGR EGIAGPQGPK GDRGSRGEKG DPGKDGVGQP GLPGPPGPPG PVVYVSEQDG   900
SVLSVPGPEG RPGFAGFPGP AGPKGNLGSK GERGSPGPKG EKGEPGSIFS PDGGALGPAQ   960
KGAKGEPGFR GPPGPYGRPG YKGEIGFPGR PGRPGMNGLK GEKGEPGDAS LGFGMRGMPG  1020
PPGPPGPPGP PGTPVYDSNV FAESSRPGPP GLPGNQGPPG PKGAKGEVGP PGPPGQPPFD  1080
FLQLEAEMKG EKGDRGDAGQ KGERGEPGGG GFFGSSLPGP PGPPGPRGYP GIPGPKGESI  1140
RGQPGPGPGPQ GPPGIGYEGR QGPPGPPGPP GPPSFPGPHR QTISVPGPPG PPGPPGPPGT  1200
MGASSGVRLW ATRQAMLGQV HEVPEGWLIF VAEQEELYVR VQNGFRKVQL EARTPLPRGT  1260
DNEVAALQPP VVQLHDSNPY PRREHPHPTA RPWRADDILA SPPRLPEPQP YPGAPHHSSY  1320
VHLRPARPTS PPAHSHRDFQ PVLHLVALNS PLSGGMRGIR GADFQCFQQA RAVGLAGTFR  1380
AFLSSRLQDL YSIVRRADRA AVPIVNLKDE LLFPSWEALF SGSEGPLKPG ARIFSFDGKD  1440
VLRHPTWPQK SVWHGSDPNG RRLTESYCET WRTEAPSATG QASSLLGGRL LGQSAASCHH  1500
AYIVLCIENS FMTASK                                                  1516

SEQ ID NO: 3             moltype = AA   length = 315
FEATURE                  Location/Qualifiers
source                   1..315
                         mol_type = protein
                         organism = Mus sp.
SEQUENCE: 3
AGQVRIWATY QTMLDKIREV PEGWLIFVAE REELYVRVRN GFRKVLLEAR TALPRGTGNE    60
VAALQPPLVQ LHEGSPYTRR EYSYSTARPW RADDILANPP RLPDRQPYPG VPHHHSSYVH   120
LPPARPTLSL AHTHQDFQPV LHLVALNTPL SGGMRGIRGA DFQCFQQARA VGLSGTFRAF   180
LSSRLQDLYS IVRRADRGSV PIVNLKDEVL SPSWDSLFSG SQGQLQPGAR IFSFDGRDVL   240
RHPAWPQKSV WHGSDPSGRR LMESYCETWR TETTGATGQA SSLLSGRLLE QKAASCHNSY   300
IVLCIENSFM TSFSK                                                    315

SEQ ID NO: 4             moltype = AA   length = 312
FEATURE                  Location/Qualifiers
source                   1..312
                         mol_type = protein
                         organism = Homo sapiens
SEQUENCE: 4
SGVRLWATRQ AMLGQVHEVP EGWLIFVAEQ EELYVRVQNG FRKVQLEART PLPRGTDNEV    60
AALQPPVVQL HDSNPYPRRE HPHPTARPWR ADDILASPPR LPEPQPYPGA PHHSSYVHLR   120
PARPTSPPAH SHRDFQPVLH LVALNSPLSG GMRGIRGADF QCFQQARAVG LAGTFRAFLS   180
SRLQDLYSIV RRADRAAVPI VNLKDELLFP SWEALFSGSE GPLKPGARIF SFDGKDVLRH   240
PTWPQKSVWH GSDPNGRRLT ESYCETWRTE APSATGQASS LLGGRLLGQS AASCHHAYIV   300
LCIENSFMTA SK                                                       312

SEQ ID NO: 5             moltype = AA   length = 233
FEATURE                  Location/Qualifiers
source                   1..233
                         mol_type = protein
                         organism = Mus sp.
SEQUENCE: 5
EPRGPTIKPC PPCKCPAPNL LGGPSVFIFP PKIKDVLMIS LSPIVTCVVV DVSEDDPDVQ    60
ISWFVNNVEV HTAQTQTHRE DYNSTLRVVS ALPIQHQDWM SGKEFKCKVN NKDLPAPIER   120
TISKPKGSVR APQVYVLPPP EEEMTKKQVT LTCMVTDFMP EDIYVEWTNN GKTELNYKNT   180
EPVLDSDGSY FMYSKLRVEK KNWVERNSYS CSVVHEGLHN HHTTKSFSRT PGK           233

SEQ ID NO: 6             moltype = AA   length = 232
FEATURE                  Location/Qualifiers
source                   1..232
                         mol_type = protein
                         organism = Homo sapiens
SEQUENCE: 6
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 7             moltype = AA   length = 28
```

-continued

```
FEATURE                    Location/Qualifiers
source                     1..28
                           mol_type = protein
                           organism = Mus sp.
SEQUENCE: 7
HTHQDFQPVL HLVLYAVTGR GDSPASSK                                        28

SEQ ID NO: 8               moltype = AA  length = 15
FEATURE                    Location/Qualifiers
source                     1..15
                           mol_type = protein
                           organism = Mus sp.
SEQUENCE: 8
LYAVTGRGDS PASSK                                                      15

SEQ ID NO: 9               moltype = AA  length = 26
FEATURE                    Location/Qualifiers
source                     1..26
                           mol_type = protein
                           organism = Mus sp.
SEQUENCE: 9
HTHQDFQPVL HLVALNTPLS GGMRGI                                          26

SEQ ID NO: 10              moltype = AA  length = 25
FEATURE                    Location/Qualifiers
source                     1..25
                           mol_type = protein
                           organism = Homo sapiens
SEQUENCE: 10
HSHRDFQPVL HLVALNSPLS GGMRG                                           25

SEQ ID NO: 11              moltype = AA  length = 15
FEATURE                    Location/Qualifiers
source                     1..15
                           mol_type = protein
                           organism = Mus sp.
SEQUENCE: 11
LYAVTGRGDS PASSK                                                      15

SEQ ID NO: 12              moltype = AA  length = 15
FEATURE                    Location/Qualifiers
source                     1..15
                           mol_type = protein
                           organism = Homo sapiens
SEQUENCE: 12
VYAVTGRGDS PASSK                                                      15

SEQ ID NO: 13              moltype = AA  length = 27
FEATURE                    Location/Qualifiers
source                     1..27
                           mol_type = protein
                           organism = Homo sapiens
SEQUENCE: 13
HSHRDFQPVL HLVYAVTGRG DSPASSK                                         27

SEQ ID NO: 14              moltype = AA  length = 27
FEATURE                    Location/Qualifiers
source                     1..27
                           mol_type = protein
                           organism = Homo sapiens
SEQUENCE: 14
ASARDFQPVL HLVYAVTGRG DSPASSK                                         27

SEQ ID NO: 15              moltype = AA  length = 27
FEATURE                    Location/Qualifiers
source                     1..27
                           mol_type = protein
                           organism = Homo sapiens
SEQUENCE: 15
HSHRDFCPVL HLVYAVTGRG DSPASSK                                         27

SEQ ID NO: 16              moltype = AA  length = 27
FEATURE                    Location/Qualifiers
source                     1..27
                           mol_type = protein
                           organism = Homo sapiens
SEQUENCE: 16
HSHRDFQPVL HLVYAVTGRA DSPASSK                                         27
```

-continued

```
SEQ ID NO: 17             moltype = AA   length = 25
FEATURE                   Location/Qualifiers
source                    1..25
                          mol_type = protein
                          organism = Mus sp.
SEQUENCE: 17
IKPGADYTIT LYAVTGRGDS PASSK                                        25

SEQ ID NO: 18             moltype = AA   length = 184
FEATURE                   Location/Qualifiers
source                    1..184
                          mol_type = protein
                          organism = Mus sp.
SEQUENCE: 18
HTHQDFQPVL HLVALNTPLS GGMRGIRGAD FQCFQQARAV GLSGTFRAFL SSRLQDLYSI  60
VRRADRGSVP IVNLKDEVLS PSWDSLFSGS QGQLQPGARI FSFDGRDVLR HPAWPQKSVW  120
HGSDPSGRRL MESYCETWRT ETTGATGQAS SLLSGRLLEQ KAASCHNSYI VLCIENSFMT  180
SFSK                                                              184

SEQ ID NO: 19             moltype = AA   length = 180
FEATURE                   Location/Qualifiers
source                    1..180
                          mol_type = protein
                          organism = Homo sapiens
SEQUENCE: 19
HSHRDFQPVL HLVALNAPLS GGMRGIRGAD FQCFQQARAV GLAGTFRAFL SSRLQDLYSI  60
VRRADRAAVP IVNLKDELLF PSWEALFSGS EGPLKPGARI FSFDGKDVLR HPTWPQKSVW  120
HGSDPNGRRL TESYCETWRT EAPSATGQAS SLLGGRLLGQ SAASCHHAYI VLCIENSFMT  180

SEQ ID NO: 20             moltype = AA   length = 27
FEATURE                   Location/Qualifiers
source                    1..27
                          mol_type = protein
                          organism = Mus sp.
SEQUENCE: 20
HTHQDFQPVL HLVALNTPLS GGMRGIR                                      27

SEQ ID NO: 21             moltype = AA   length = 48
FEATURE                   Location/Qualifiers
source                    1..48
                          mol_type = protein
                          organism = Homo sapiens
SEQUENCE: 21
SYCETWRTEA PSATGQASSL LGGRLLGQSA ASCHHAYIVL CIENSFMT              48

SEQ ID NO: 22             moltype = AA   length = 27
FEATURE                   Location/Qualifiers
source                    1..27
                          mol_type = protein
                          organism = Homo sapiens
SEQUENCE: 22
HSHRDFQPVL HLVALNAPLS GGMRGIR                                      27

SEQ ID NO: 23             moltype = AA   length = 5
FEATURE                   Location/Qualifiers
REGION                    1..5
                          note = Enterokinase cleavage site
source                    1..5
                          mol_type = protein
                          organism = synthetic construct
SEQUENCE: 23
DDDDK                                                              5

SEQ ID NO: 24             moltype = AA   length = 227
FEATURE                   Location/Qualifiers
source                    1..227
                          mol_type = protein
                          organism = Homo sapiens
SEQUENCE: 24
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 25             moltype = AA   length = 227
FEATURE                   Location/Qualifiers
source                    1..227
                          mol_type = protein
                          organism = Homo sapiens
```

```
SEQUENCE: 25
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK               227

SEQ ID NO: 26           moltype = AA  length = 227
FEATURE                 Location/Qualifiers
source                  1..227
                        mol_type = protein
                        organism = Homo sapiens
SEQUENCE: 26
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK               227

SEQ ID NO: 27           moltype = AA  length = 554
FEATURE                 Location/Qualifiers
source                  1..554
                        mol_type = protein
                        organism = Homo sapiens
SEQUENCE: 27
SGVRLWATRQ AMLGQVHEVP EGWLIFVAEQ EELYVRVQNG FRKVQLEART PLPRGTDNEV    60
AALQPPVVQL HDSNPYPRRE HPHPTARPWR ADDILASPPR LPEPQPYPGA PHHSSYVHLR   120
PARPTSPPAH SHRDFQPVLH LVALNSPLSG GMRGIRGADF QCFQQARAVG LAGTFRAFLS   180
SRLQDLYSIV RRADRAAVPI VNLKDELLFP SWEALFSGSE GPLKPGARIF SFDGKDVLRH   240
PTWPQKSVWH GSDPNGRRLT ESYCETWRTE APSATGQASS LLGGRLLGQS AASCHHAYIV   300
LCIENSFMTA SKDDDDDKGG GGSEPKSQDK THTCPPCPAP ELLGGPSVFL FPPKPKDTLM   360
ISRTPEVTCV VVDVSHEDPE VKFNWYVDGV EVHNAKTKPR EEQYNSTYRV VSVLTVLHQD   420
WLNGKEYKCK VSNKALPAPI EKTISKAKGQ PREPQVYTLP PCRDELTKNQ VSLWCLVKGF   480
YPSDIAVEWE SNGQPENNYK TTPPVLDSDG SFFLYSKLTV DKSRWQQGNV FSCSVMHEAL   540
HNHYTQKSLS LSPG                                                   554

SEQ ID NO: 28           moltype = AA  length = 232
FEATURE                 Location/Qualifiers
source                  1..232
                        mol_type = protein
                        organism = Homo sapiens
SEQUENCE: 28
EPKSQDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVCTLPPSR DELTKNQVSL SCAVKGFYPS DIAVEWESNG QPENNYKTTP   180
PVLDSDGSFF LVSKLTVDKS RWQQGNVFSC SVMHEALHNH YTQKSLSLSP GK          232

SEQ ID NO: 29           moltype = AA  length = 552
FEATURE                 Location/Qualifiers
source                  1..552
                        mol_type = protein
                        organism = Homo sapiens
SEQUENCE: 29
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPCRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGGGGG SPGSDDDDDK   240
SGVRLWATRQ AMLGQVHEVP EGWLIFVAEQ EELYVRVQNG FRKVQLEART PLPRGTDNEV   300
AALQPPVVQL HDSNPYPRRE HPHPTARPWR ADDILASPPR LPEPQPYPGA PHHSSYVHLR   360
PARPTSPPAH SHRDFQPVLH LVALNSPLSG GMRGIRGADF QCFQQARAVG LAGTFRAFLS   420
SRLQDLYSIV RRADRAAVPI VNLKDELLFP SWEALFSGSE GPLKPGARIF SFDGKDVLRH   480
PTWPQKSVWH GSDPNGRRLT ESYCETWRTE APSATGQASS LLGGRLLGQS AASCHHAYIV   540
LCIENSFMTA SK                                                     552

SEQ ID NO: 30           moltype = AA  length = 227
FEATURE                 Location/Qualifiers
source                  1..227
                        mol_type = protein
                        organism = Homo sapiens
SEQUENCE: 30
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK               227

SEQ ID NO: 31           moltype = AA  length = 5
FEATURE                 Location/Qualifiers
source                  1..5
                        mol_type = protein
                        organism = Homo sapiens
SEQUENCE: 31
```

-continued

```
PHSRN                                                              5

SEQ ID NO: 32        moltype = AA  length = 9
FEATURE              Location/Qualifiers
VARIANT              1..2
                     note = unsure - Xaa at positions 1 and 2 may be any
                      naturally-occurring amino acid
source               1..9
                     mol_type = protein
                     organism = Mus sp.
SEQUENCE: 32
XXHLRPARP                                                          9

SEQ ID NO: 33        moltype = AA  length = 10
FEATURE              Location/Qualifiers
VARIANT              5
                     note = unsure - Xaa at position 5 may be any
                      naturally-occurring amino acid
source               1..10
                     mol_type = protein
                     organism = Mus sp.
SEQUENCE: 33
PARPXSPPAH                                                         10

SEQ ID NO: 34        moltype = AA  length = 10
FEATURE              Location/Qualifiers
source               1..10
                     mol_type = protein
                     organism = Mus sp.
SEQUENCE: 34
SPPAHSHRDF                                                         10
```